United States Patent
Hagen et al.

(10) Patent No.: US 11,026,426 B2
(45) Date of Patent: Jun. 8, 2021

(54) OXADIAZOLE AND PHENOL DERIVATIVES AS ANTIBACTERIAL AND/OR HERBICIDAL AGENTS

(71) Applicant: NORTHERN ILLINOIS RESEARCH FOUNDATION, Dekalb, IL (US)

(72) Inventors: Timothy J. Hagen, Lisle, IL (US); Michael Thompson, Dekalb, IL (US); Jeremy R. Troxell, Dekalb, IL (US); Brian E. Hartnett, Dekalb, IL (US)

(73) Assignee: Northern Illinois Research Foundation, DeKalb, IL (US)

( * ) Notice: Subject to any disclaimer, the term of this patent is extended or adjusted under 35 U.S.C. 154(b) by 0 days.

(21) Appl. No.: 15/933,608

(22) Filed: Mar. 23, 2018

(65) Prior Publication Data
US 2018/0271098 A1 Sep. 27, 2018

Related U.S. Application Data

(60) Provisional application No. 62/518,947, filed on Jun. 13, 2017, provisional application No. 62/476,260, filed on Mar. 24, 2017.

(51) Int. Cl.
| | |
|---|---|
| A61K 31/4245 | (2006.01) |
| A01N 43/82 | (2006.01) |
| C07D 413/04 | (2006.01) |
| A01N 43/36 | (2006.01) |
| C07D 209/12 | (2006.01) |
| C07D 417/04 | (2006.01) |

(52) U.S. Cl.
CPC ............ *A01N 43/82* (2013.01); *A01N 43/36* (2013.01); *A61K 31/4245* (2013.01); *C07D 209/12* (2013.01); *C07D 413/04* (2013.01); *C07D 417/04* (2013.01)

(58) Field of Classification Search
CPC .................................................. A61K 31/4245
See application file for complete search history.

(56) References Cited

PUBLICATIONS

Rajeeva et al. (E-Journal of Chemistry, 2009, 6, 775-779).*
Bhardw et al. (E-Journal of Chemistry, 2009, 6, 1133-1138).*
Zhang et al. (Yaoxue Xuebao, 1984, 19, 737-41—abstract only).*
Bali et al., Synthesis, docking and pharmacological evaluation of novel indole based potential atypical antipsychotics, *European Journal of Medicinal Chemistry*, 2014, 74, 477-490.
Baugh et al., Increasing the structural coverage of tuberculosis drug targets, *Tuberculosis (Edinb)* 2015, 95, 142-148.
Bjorkelid, C., et al., Structural and functional studies of mycobacterial IspD enzymes, *Acta Crystallogr D Biol Crystallogr* 2011, 67, 403-414.
Eisenreich, W., et al. Biosynthesis of isoprenoids via the non-mevalonate pathway, *Cellular and Molecular Life Sciences CMLS* 2004, 61,1401-1426.
Eoh, H., et al. Characterization of the *Mycobacterium tuberculosis* 4-diphosphocytidyl-2-C-methyl-D-erythritol synthase: potential for drug development. *J Bacteriol* 2007, 189, 8922-8927.
Hansch et al., ρ-σ-π Analysis. A Method for the Correlation of Biological Activity and Chemical Structure, *Journal of the American Chemical Society* 1964, 86, 1616-1626.
Hedden, P. and S. G. Thomas. Gibberellin biosynthesis and its regulation. *Biochem J* 2012, 444, 11-25.
Hunter, W. N. The Non-mevalonate Pathway of Isoprenoid Precursor Biosynthesis. *Journal of Biological Chemistry* 2007, 282, 21573-21577.
Illarionova, V., et al. Nonmevalonate terpene biosynthesis enzymes as antiinfective drug targets: substrate synthesis and high-throughput screening methods. *J Org Chem* 2006, 71, 8824-8834.

(Continued)

*Primary Examiner* — Brian E McDowell
(74) *Attorney, Agent, or Firm* — Barnes & Thornburg LLP; Alice O. Martin

(57) ABSTRACT

Compounds of formula I

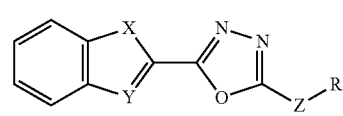

and II

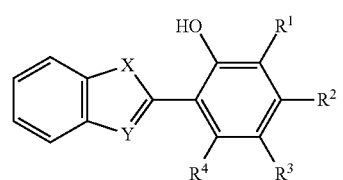

are described. In formulae I and II, X is —NH— or —S— and Y is —CH═ or —N═. In formula I, Z is $C_1$-$C_6$ alkylene, $C_2$-$C_6$ alkenylene, $C_6$-$C_{10}$ arylene, or $C_3$-$C_6$ cycloalkylene, or Z is absent. In formula I, R is hydrogen, halogen, —OH, —NO$_2$, $C_1$-$C_6$ alkyl, $C_2$-$C_6$ alkenyl, $C_6$-$C_{10}$aryl, —O($C_1$-$C_6$ alkyl), or —O($C_6$-$C_{10}$ aryl), wherein each hydrogen atom in $C_1$-$C_6$ alkyl, $C_2$-$C_6$ alkenyl, $C_6$-$C_{10}$ aryl, —O($C_1$-$C_6$ alkyl), and —O($C_6$-$C_{10}$ aryl) is independently optionally substituted by halogen, —OH, or —NO$_2$. In formula II, $R^1$, $R^2$, $R^3$, and $R^4$ are each independently hydrogen, halogen, —OH, —NO$_2$, $C_1$-$C_6$ alkyl, $C_2$-$C_6$ alkenyl, or $C_6$-$C_{10}$ aryl, wherein each hydrogen atom in $C_1$-$C_6$ alkyl, $C_2$-$C_6$ alkenyl, and $C_6$-$C_{10}$ aryl is independently optionally substituted by halogen, —OH, or —NO$_2$. Methods of inhibiting bacteria are also described.

1 Claim, 27 Drawing Sheets
(6 of 27 Drawing Sheet(s) Filed in Color)

(56) References Cited

PUBLICATIONS

Imlay, L. S., et al. Plasmodium IspD (2-C-Methyl-d-erythritol 4-Phosphate Cytidyltransferase), an Essential and Druggable Antimalarial Target. *ACS Infectious Diseases* 2015, 1, 157-167.
Jomaa, H., et al. Inhibitors of the Nonmevalonate Pathway of Isoprenoid Biosynthesis as Antimalarial Drugs. *Science* 1999, 285, 1573-1576.
Kikuchi et al., Effects of 1,5-Distributed Imidazoles on the Growth of Lettuce an Rice Seedlings, J. Fac. Agr. Kyushu Univ., 36(1-2): 83-91 (1991).
Kranz, J. K. and C. Schalk-Hihi. Chapter eleven—Protein Thermal Shifts to Identify Low Molecular Weight Fragments. *Methods in Enzymology*. C. K. Lawrence, Academic Press. 2011, 493, 277-298.
Kunfermann et al., Pseudilins: Halogenated, Allosteric Inhibitors of the Non-Mevalonate Pathway Enzyme IspD. *Angew. Chem. Int. Ed.* 2014, 53, 2235-2239.
Kuzuyama, T., et al. Formation of 4-(cytidine 5'-diphospho)-2-C-methyl-d-erythritol from 2-C-methyl-d-erythritol 4-phosphate by 2-C-methyl-d-erythritol 4-phosphate cytidylyltransferase, a new enzyme in the nonmevalonate pathway. *Tetrahedron Letters* 2000, 41, 703-706.
Kuzuyama, T., et al. Studies on the nonmevalonate pathway: conversion of 4-(cytidine 5'-diphospho)-2-C-methyl-d-erythritol to its 2-phospho derivative by 4-(cytidine 5'-diphospho)-2-C-methyl-d-erythritol kinase. *Tetrahedron Letters* 2000, 41, 2925-2928.
Lange, B. M., et al. Isoprenoid biosynthesis: The evolution of two ancient and distinct pathways across genomes. *Proceedings of the National Academy of Sciences* 2000, 97, 13172-13177.
Lavinder, J. J., et al. High-Throughput Thermal Scanning: A General, Rapid Dye-Binding Thermal Shift Screen for Protein Engineering. *Journal of the American Chemical Society* 2009, 131, 3794-3795.
Li et al., 1-(2-Hydroxy-3,5-dimethoxyphenyl)-Ethanone. *Acta Crystallographica Section E Structure Reports Online* 2012, E68, o116.
Lüttgen, H., et al. Biosynthesis of terpenoids: YchB protein of *Escherichia coli* phosphorylates the 2-hydroxy group of 4-diphosphocytidyl-2C-methyl-d-erythritol. *Proceedings of the National Academy of Sciences* 2000, 97, 1062-1067.
Martin et al., Silver(I)-Catalyzed Route to Pyrroles: Synthesis of Halogenated Pseudilins as Allosteric Inhibitors for Myosin ATPase and X-ray Crystal Structures of the Protein-Inhibitor Complexes. *Eur. J. Org. Chem.* 2014, 4487-4505.
Masini, T. and A. K. H. Hirsch. Development of Inhibitors of the 2C-Methyl-d-erythritol 4-Phosphate (MEP) Pathway Enzymes as Potential Anti-Infective Agents. *Journal of Medicinal Chemistry* 2014, 57, 9740-9763.
Miziorko, H. M. Enzymes of the mevalonate pathway of isoprenoid biosynthesis. *Arch Biochem Biophys*, 2011, 505, 131-143.
Niesen, F. H., et al. The use of differential scanning fluorimetry to detect ligand interactions that promote protein stability. *Nat. Protocols* 2007, 2, 2212-2221.
Rajeeva, B., et al. Synthesis and Antimicrobial Activity of Some New 2-Substituted Benzothiazole Derivatives. *E-Journal of Chemistry* 2009, 6, 775-779.
Richard, S. B., et al. Kinetic Analysis of *Escherichia coli* 2-C-Methyl-d-erythritol-4-phosphate Cytidyltransferase, Wild Type and Mutants, Reveals Roles of Active Site Amino Acids. *Biochemistry* 2004, 43, 12189-12197.
Robba et al., As-Triazino[4,5-a]indoles. I. Indole Derivatives. *Bulletin De La Societe Chimique De France Pt.2* 1977, 3, 333-36.
Rohmer, M. The discovery of a mevalonate-independent pathway for isoprenoid biosynthesis in bacteria, algae and higher plants. *Natural Product Reports* 1999, 16, 565-574.
Sawhney, S. N., and Asha Gupta. Synthesis of Some 2-(5-substituted 1,3,4-oxadiazol-2-yl)-, 2-(5-substituted 1,3,4-thiadiazol-2-yl)-, and 2-(3-mercapto-4-substituted-4H-1,2,4-triazol-5-yl)benzimidazoles as Potential Antiinflammatory Agents. *Indian Journal of Chemistry, Section B: Organic Chemistry Including Medicinal Chemistry* 1991, 30B, 407-12.
Topliss, J. G. A manual method for applying the Hansch approach to drug design. *Journal of Medicinal Chemistry* 1977, 20, 463-469.
Topliss, J. G. Utilization of operational schemes for analog synthesis in drug design. *Journal of Medicinal Chemistry* 1972, 15, 1006-1011.
Viegas, A., et al. Saturation-Transfer Difference (STD) NMR: A Simple and Fast Method for Ligand Screening and Characterization of Protein Binding. *Journal of Chemical Education* 2011, 88, 990-994.
Vranova, E., et al. Network analysis of the MVA and MEP pathways for isoprenoid synthesis. *Annu Rev Plant Biol* 2013, 64, 665-700.
Vranova, E., et al. Structure and dynamics of the isoprenoid pathway network. *Mol Plant* 2012, 5, 318-333.
Wiemer, A. J., et al. Isoprenoid metabolism as a therapeutic target in gram-negative pathogens. *Curr Top Med Chem* 2010, 10, 1858-1871.
World Health Organization—Malaria—Factsheet on the World Malaria Report 2013. http://www.who.int/malaria/media/world_malaria_report_2013/en/ (accessed May 4, 2015).
Yamada, N., et al. Synthesis and Bleaching Activity of 1,5-Disubstituted Imidazoles. *Bioscience, Biotechnology, and Biochemistry* 1992, 56, 1943-1948.
Zhao, L., et al. Methylerythritol Phosphate Pathway of Isoprenoid Biosynthesis. *Annual Review of Biochemistry*, 2013, 82, 497-530.

\* cited by examiner

Cholesterol

Ubiquinone

Gibberellins

Beta-carotene

HGN-207

HGN-208

HGN-209

HGN-211

HGN-212

HGN-213

HGN-239

HGN-240

HGN-241

HGN-242

HGN-249

HGN-250

HGN-251

HGN-252

HGN-253

HGN-254

HGN-287

HGN-288

HGN-340

HGN-421

HGN-422

E. coli IspD

P. falciparum IspD

OXADIAZOLE AND PHENOL DERIVATIVES AS ANTIBACTERIAL AND/OR HERBICIDAL AGENTS

CROSS REFERENCE TO RELATED APPLICATIONS

This application claims the benefit of priority under 35 U.S.C. § 119(e) to U.S. Provisional Patent Application Nos. 62/476,260, filed Mar. 24, 2017 and 62/518,947 filed Jun. 13, 2017. The disclosures set forth in the reference applications are incorporated herein by reference in their entireties.

The United States Government has rights in this invention pursuant to Contract No. NIH R15 AI 113653 between the United States Government and the Board of Trustees of Northern Illinois University.

BACKGROUND

Small molecule analogs of 2-(1H-indol-2-yl)-1,3,4-oxadiazole (also known as FOL-7082) were synthesized and found to have improved antibacterial activity by inhibiting the enzymes IspD and IspE in the MEP pathway.

Arguably one of the greatest medical developments is the discovery of antibiotics. Antibiotics have not only helped increase the average human lifespan and quality of life, but are also needed as defense against biological select agents and toxins (BSATs). Due to overuse and incorrect use of antibiotics, bacteria have developed resistance against most classes of antibiotics. Bacteria continue to mutate and develop resistant genes. Discovering unique classes and mechanisms of action is a necessity for fighting back.

With the establishment of antibiotics came the generation of antimicrobial resistance. Antibiotic resistance is a predominant threat within the health care system with estimated costs of greater than $20 billion in the United States alone. Antibiotic resistance may evolve through natural selection with random mutations that are capable of developing a resistance gene that enables the bacteria to tolerate antibiotic treatment. With each antibiotic treatment there is an increase in the resistant subpopulation, until the strain becomes primarily drug-resistant.

Due to this resistance, the necessity of new antibiotics in which to fight these resistant strains of bacterial infections is dire. Despite this fact, since the 1950s, new antibiotic approvals through the US Food and Drug Administration (FDA) have drastically reduced each decade, which has culminated in a "discovery void" since the 1990s.

Approaches to new antibiotic development include analogs of known compounds or use of known classes that address known targets, new compounds with new mechanisms of action within new classes that act on known targets, and compounds within new classes acting on novel targets, Antibacterial Targets Each antibiotic class has a core structure related to its mode of action, with family members in the class possessing modifications around the core. The different classes are commonly associated with their target such as cell wall biosynthesis, protein synthesis, DNA and RNA synthesis, folate synthesis, and disruption of cell membranes. Targeting and inhibiting these pathways halts a metabolic process that can lead to cell death.

1. Targeting Cell Wall Synthesis

One of the most common pathways for antibiotic development includes inhibiting the synthesis of bacterial cell walls and interfering with their structural integrity. This strategy has worked well, as most bacteria possess a peptidoglycan cell wall while eukaryotic cells do not. Peptidoglycans are polymers of disaccharides which are cross-linked by pentapeptide side chains. These polymers are maintained by a series of enzymes including transpeptidases, such as DD-transpeptidases, which are targets for a number of antibiotics.

2. Inhibition of Protein Synthesis

The synthesis of proteins within the ribosomes of bacteria, is a major antibiotics target. There are three phases in the translation process that may be targeted: initiation, elongation and termination. Ribosomes are made up of two subunits, a larger 50s and a smaller 30s, which associate at the initiation step of translation.

Antibiotics targeting initiation at the ribosome level include compounds such as macrolides, lincosamides, aminoglycosides, tetracyclines, chloramphenicol, streptogramins, and oxazolidinones.

3. Inhibition of DNA or RNA Synthesis

Another pathway taken to an antibiotic is impeding DNA replication and RNA transcription.

4. Inhibiting Folate Synthesis

Folate is a compound necessary for cell division, DNA and RNA synthesis and methylation of DNA. Humans are unable to synthesize folates de novo; however, bacteria have the ability to biosynthetically create DNA bases from para-aminobenzoic acid (PABA) and pteridine.

5. Cell Membrane Disruption

Another pathway used for antibiotic development, is disruption of cellular membranes. These membranes are composed of proteins and phospholipids, which allow selective permeability where bacteria take in nutrients and dispel out waste. Disturbing this balance between nutrient and waste, through compromising the integrity of the cell membrane, is a suitable approach for antibiotics, which can lead to cell death.

Target Pathways in Bacteria

1. Isoprenoid Biosynthesis

Isoprenoids are a class of compounds that represent one of the most diverse group of metabolites in both structure and function. Isoprenoids make up more than 50,000 recognized molecules and are the oldest known biomolecules, with hopanoids being recovered from 2.5 billion year old sediments. These molecules have a wide range of functions including the electron transport chain quinones, membrane components such as prenyl lipids and sterols found in archaebacteria and eubacteria, cellular targeting agents seen in prenylation of proteins, carotenoids that serve as side chains in chlorophyll, hormones such as plant gibberellins, which promote growth, and as plant defense molecules, including monoterpenes, sesquiterpenes, and diterpenes. These compounds are all synthetically derived from a 5-carbon subunit isopentenyl diphosphate (IPP) and dimethylallyl diphosphate (DMAPP) (FIG. 1). Examples of some common isoprenoids are shown in FIG. 2.

2. Mevalonic Acid (MVA) Pathway

Synthesis of IPP can occur via two different pathways. One pathway is the cytoplasmic mevalonic acid (MVA) pathway (FIG. 3). The MVA pathway, which is present in humans, utilizes the precursor acetyl-CoA in which the first step involves the condensation of two acetyl-CoA molecules through action of acetoacetyl-CoA thiolase to form acetoacetyl-CoA via a Claisen condensation reaction. This product is converted to 3-hydroxy-3-methylglutaryl-CoA by HMG synthase. In two reduction steps, with NADPH as a reducing equivalent, 3-hydroxy-3-methylglutaryl-CoA is converted to mevalonic acid (MVA) for which the pathway is named. These reductions are done by the enzyme 3-hydroxy-3-methylglutaryl-CoA reductase. Mevalonic acid is phosphorylated twice: once with MVA kinase and a second time with phospho-MVA kinase (MVK and PMK respectively). This produces mevalonate-5-diphosphate. An ATP-dependent decarboxylation of MVA 5-diphosphate by MVA diphosphate decarboxylase (MPD) produces the desired IPP subunit for isoprenoid synthesis.

3. 2-C-Methyl-D-Erythritol 4-Phosphate (MEP) Pathway

The second pathway that leads to IPP is utilized by many bacteria and some higher plant life and is called the MEP pathway after one of the intermediates (2-C-Methyl-D-erythritol 4-phosphate). This pathway (FIG. 4) was discovered and reported in 1999 using [$C_1$]glucose and [C]acetate isotopomers that seemed to be incorporated into hopanoids in ways not conducive to the traditional mevalonate pathway. In this pathway, the precursor is D-glyceraldehyde-3-phosphate. In the first step, a condensation between the C1 aldehyde group of D-glyceraldehyde-3-phosphate and (hydroxyethyl)thiamin (a derivative of pyruvate) is catalyzed by 1-deoxy-D-xylulose-5-phosphate synthase (DXS). This reaction releases $CO_2$ and is irreversible. The product, 1-deoxy-D-xylulose 5-phosphate undergoes an intramolecular rearrangement and reduction to produce 2-C-Methyl-D-erythritol 4-phosphate by action from DXP reductoisomerase (IspC). MEP is converted to 4-(cytidine 5'-diphospho)-2-C-methyl-D-erythritol (CDP-ME) by 2-C-methyl-D-erythritol-4-phosphate cytidylyltransferase (IspD) in a CTP-dependent reaction. Phosphorylation of a hydroxyl group at the C2 position of CDP-ME by 4-(cytidine 5'-diphospho)-2-C-methyl-D-erythritol kinase (IspE) results in 2-phospho-4-(cytidine 5'-diphospho)-2-C-methyl-D-erythritol (CDP-MEP). This is converted to 2-C-methyl-D-erythritol 2,4-cyclodiphosphate (MEcPP) by 2-C-methyl-D-erythritol-2,4-cyclodiphosphate synthase (IspF). MEcPP is reduced by 4-hydroxy-3-methylbut-2-enyldiphosphate synthase (IspG) to 4-hydroxy-3-methylbut-2-enyldiphosphate. Finally, this is converted to both IPP and DMAPP by IspH, which can isomerize through action of IPP A-isomerase. DMAPP is an active molecule for condensation reactions with IPP.

Certain plants utilize both the MVA and MEP pathways and these are often compartmentalized, where MEP pathway reactions take place in chloroplasts and MVA pathway reactions in the cytosol, but some common metabolites can be exchanged between compartments. MEP pathway enzymes may be targets of broad-spectrum antimicrobial and herbicidal agents or utilized by genetic modification of microorganisms to produce compounds of medical and agricultural importance.

4. MEP Pathway as a Drug Target

The development of two separate pathways for isoprenoid biosynthesis is quite advantageous to the development of new compounds to combat parasitic and microbial infections. The enzymes present in the MEP pathway are potential targets for metabolic inhibition of various pathogens, as there are no analogous enzymes present in humans. These enzymes in the MEP pathway are vital for many pathogens and their function cannot be compensated by other enzymes present within the cell. In humans, inhibition of isoprenoid synthesis has become a subject of research for treatment of hypercholesterolemia, osteoporosis, and certain cancers. Humans utilize the MVA pathway, which uses different enzymes than the MEP pathway. Isoprenoids are also required in bacteria as essential components of electron transport and cell wall biosynthesis. Gene knockout or enzyme inhibition with the antibiotic fosmidomycin has shown that MEP pathway enzymes are necessary for certain bacterial growth. As multi-drug resistance in bacteria becomes a problem, it is quite beneficial to develop inhibitors of these enzymes. One of the most notorious pathogens that utilize the MEP pathway is the malaria parasite. Malaria is prevalent in many developing countries and is one of the most severe public health problems. About half of the world's population (3.4 billion people) lives in high malaria risk areas. In 2012, there have been an estimated 207 million clinical cases of malaria infection, which resulted in around 627,000 deaths.

The malaria parasite has become resistant to typical antimalarial drugs, such as chloroquine, at a high rate and as such, new drugs are in urgent demand.

a) Targeting IspD

The third enzyme in the MEP pathway, IspD, catalyzes the conversion of MEP to CDP-ME by transferring the CMP from cytidine triphosphate (CTP) to the phosphate on the MEP, releasing pyrophosphate. Currently, there are 35 crystal structures of IspD from 13 different species possessing 31 different ligands deposited in the protein database (PDB). Most notably, a crystal structure of IspD bound to CTP and the reaction product CDP-ME, allows insight in the structure of the active site.

IspD is proposed to be active as a dimer with the subunits consisting of a seven strand β-sheet with an α/β structure around it and an arm-like loop that interacts with its neighboring monomer to form the observed homodimer. Within the face of the dimer interface, there is a highly conserved active site between species, specifically when comparing the sequences of *Escherichia coli*, *Burkholderia thailandensis*, *Mycobacterium tuberculosis*, and *Arabidopsis thaliana*. Despite the presence of any direct interactions with IspD residues, a divalent metal ion (most often $Mg^{2+}$) is necessary for the activity of the enzyme and is found coordinated to the α, β, and γ phosphates of CTP, likely stabilizing the reaction intermediate. Along with the $Mg^{2+}$, residues Lys-27 and Lys-213 aid in the coordination of the phosphates and are conserved across different species. The base binding pocket is also conserved within the active site involving hydrogen bonds being formed between the backbone amides from Ala-14 and Ala-15 with *B. thailandensis* having a cysteine instead of an Ala-14. The carbonyl oxygen of Gly-82 also creates hydrogen bonds and Asp-83 in *E. coli*, however, Asp-83 is not conserved between species. The hydroxyl groups of the ribose ring coordinate with Pro-13, Gly-16 and Ala-107 which are completely conserved between *E. coli*, *B. thailandensis* and *M. tuberculosis*, Pro-13 and Ala-107 are Val-13 and Ser-107 respectively for *A. thaliana*.

4-Diphosphocytidyl-2C-methyl-D-erythritol synthase, or IspD, is the third enzyme in the MEP pathway that is utilized to catalyze the formation of 4-diphosphocytidyl-2C-methyl-D-erythritol by transfer of a diphosphocytidyl unit from CTP to 2-C-methylerythritol 4-phosphate, or MEP (FIG. 7).

b) IspD (*Mycobacterium paratuburculosis*)

The structure of IspD is a homodimer with a globular domain consisting of α/β folds. IspD contains a highly conserved active site in each monomer among various species of bacteria and plants. Most residues of the active site belong to the main globular domain, but some are located in the β-arm. Each active site (2 active sites for the dimer) is found at the dimer interface, making it relatively exposed to solvent and as a result, competitive inhibitors to the natural substrate are difficult to make as the active site is found in a polar environment. (FIG. 8)

The catalytic activity of IspD requires the presence of divalent cations, of which $Mg^{2+}$ is optimal for many bacterial species such as *Mycobacterium tuberculosis* and *Escherichia coli*. $Mg^{2+}$ coordinates with the enzyme first. After $Mg^{2+}$, CTP binds, followed by MEP. The proposed role of the active site amino acids is shown in FIG. 9.

IspD, the third enzyme in the non-mevalonate pathway, catalyzes the creation of if 4-diphosphocytidyl-2-C-methylerythritol (CDP-ME) which is the substrate for IspE. This in turn creates CDP-MEP with ATP. Inhibiting these enzymes would disrupt the formation of isoprenoids needed for biological function.

c) Targeting IspE

The fourth enzyme in the MEP pathway (IspE) catalyzes the adenosine triphosphate (ATP) dependent phosphorylation of CDP-ME to CDP-MEP. This kinase is also an attractive target for inhibition to disrupt the biosynthesis of isoprenoids. To date, there are 17 crystal structures of six different species of IspE deposited in the PDB with 17 different ligands.

IspE is commonly reported as a homodimer, with each monomer comprising of 10 α-helices and 12 β-sheets. Monomers dimerize with salt bridges formed between Arg-21 of one monomer and Asp-80 on the other monomer, along with hydrogen bonds formed between the amide of Gly-87 and the carbonyl of Ala-22. The dimer results in a solvent-filled channel with active sites at each end of the channel. Each subunit has two domains; one domain provides a binding site for ATP, the second provides a binding site for the substrate CDP-ME.

Active sites are highly conserved between species, with 100% sequence homology in the CDP-ME binding site and a 75% sequence homology in the ATP binding site between *E. coli* and *B. thailandensis* IspE. The ATP binding subunit comprises of a purine binding pocket which involves hydrogen bonding to Asn-65 and Asn-110 on either side of the adenine base along with Leu-66 and Lys-96. The ribose ring and phosphates are solvent exposed with the phosphate portion forming hydrogen bonds with the amides in a glycine rich loop (Gly-103, Gly-105 and Gly-107) and Ser-108.

The second subunit, in which CDP-ME binds to, comprises of two aromatic side chains (Phe-185 and Tyr-25) in which the cytosine portion of the CDP-ME will coordinate in between along with hydrogen bonds with His-26. The ribose ring and phosphates are again solvent exposed with the α and β-phosphates of the CDP-ME directed to the γ-phosphate of the ATP. The oxygen linker between the α and β-phosphates of the CDP-ME is coordinated by a hydrogen bond with Ala-140. Hydrogen bonding with the hydroxyl on the methylerythritol involves Asp-141, Lys-10 and Asn-12.

d) ISPE (*Mycobacterium abscessus*)

4-diphosphocytidyl-2C-methyl-D-erythritol kinase, or IspE, is the fourth enzyme in the MEP pathway. It is a kinase that catalyzes the transfer of the γ-phosphoryl group of ATP to 4-diphosphocytidyl-2-C-methylerythritol via the 2-hydroxyl group (FIG. 10).

IspE belongs to the galactose/homoserine/mevalonate/phophomevalonate kinase superfamily (GHMP). IspE is a monomer in solution and contains a two-domain fold which contains an ATP and substrate binding domain and the active site is found in a deep pocket between the two domains, which is stabilized by water-mediated interactions after the substrate binds.

Fragment Hit Identification of FOL7082

An initial screening of a small molecule fragment library by the Seattle Structural Genomics Center for Infectious Disease was performed by Dr. Darren Begley using a saturation transfer difference NMR technique. This method utilizes the nuclear Overhauser effect (NOE) and it relies on the fact that a weak-binding ligand will exchange between a bound and free ligand state. A $^1$H-NMR experiment is performed on a free ligand in solution with the protein of interest without a saturation pulse (Off-resonance). A subsequent $^1$H-NMR experiment is done in which the solution is irradiated with a saturation pulse that is selective to the protein, typically at 0 ppm to −1 ppm (On-resonance). By irradiating the sample at a selective frequency, the protein or receptor will become saturated and the signal intensity will diminish. Saturation is transferred through the protein/receptor to the fragment if the fragment is within 5 Å of the protein in a binding event. The saturation-transfer difference is a measure of the difference between signal intensities of the ligand in the off-resonance state, $I_0$, and the signal intensities following the saturation pulse, $I_{SAT}$. If the fragment bound tightly, the $I_{SAT}$ will be close to zero and the difference between $I_0$ and $I_{SAT}$ is near $I_0$. If a part of the ligand did not bind to the protein and there was little saturation transferred, $I_{SAT}$ will approach $I_0$, and $I_0$-$I_{SAT}$ will approach 0. By subtracting the on-resonance spectrum from the off-resonance spectrum, a saturation transfer difference (STD) spectrum is generated.

The peak intensities for the ligand are directly proportional to the degree of binding to the protein/receptor. By using this data, a series of small molecule fragments were identified to bind to various enzymes in the MEP pathway.

In total, 1020 fragments were screened from the "Fragments of Life" compound library against the IspD from *Mycobacterium* paratuberculosis, IspE from *Mycobacterium abscessus*, and IspF from *Burkholderia pseudomallei*. Of the 1020 compounds, 102 were found to bind to MpIspD, 176 were found to bind to MaIspE, and 81 were found to bind to BpIspF. Of these, 37 bound both to MpIspD and MaIspE. (see Table 6, and FIG. 6)

One of the shortcomings of utilizing STD-NMR is that the exact binding mode of the fragments cannot be determined without further experiments and the strength of binding is unknown without further assay data. Of the 37 dual binding fragments, FOL7082 was further explored to increase binding efficiency using a Topliss tree approach (described herein).

SUMMARY

New insights are provided into the biophysical properties of IspD and IspE enzymes and methods to evaluate compounds with potential inhibitory activity. A high throughput thermal shift assay was designed to assess inhibitors for further studies. Enzymatic assays were developed to further study compounds for both IspD and IspE. Inhibitors of Ec IspD were discovered to be in high micromolar range from the MicroSource Spectrum collection which are more potent than low millimolar range. IspE from both *E. coli* and *B. thailandensis* were found to have several inhibitors from the oxadiazole series in the low micromolar range. No inhibitors against *B. thailandensis* IspE have been reported, making it an attractive target.

Analogs of 2-(1H-indol-2-yl)-1,3,4-oxadiazole (also known as FOL-7082) were synthesized and found to inhibit the EcIspD (*Escherichia coli*) and BtIspE (*Burkholderia thailondensis*) enzymes. Antibacterial activity of the analogs against 9 strains of bacteria was determined Some analogs have activity against *Pseudomonas aeruginosa* and other bacteria at about 150 micrograms/milliters (Kirby-Bauer assay).

From the variety of assays utilized to evaluate the compound library of analogs, the general trend observed is that a phenyl ring substitution on the 1,3,4-oxadiazole was beneficial, and when the phenyl was substituted at the 4 position, activity was strongly enhanced for IspD and IspE. Depending on the species of IspD targeted, an electron donating or electron withdrawing substituent enhanced activity greatly. Utilizing the 4-substituted phenyl compounds that had greatest activity in the indole series, a benzothiazole series was synthesized which resulted in a significant loss in activity, likely due to loss of the hydrogen bond donating indole N—H or the electron withdrawing effects of the heterocycle. When a benzothiazole series was made, activity was greatly enhanced as in addition to the hydrogen bond donor, a hydrogen bond acceptor was also added compared to the indole parent compound.

Compound HGN-340, not an oxadiazole, was also found to have antibacterial activity, possibly through inhibition of the IspD enzyme. HGN-340 showed significant inhibition of AtIspD, and analogs of this compound are predicted to be beneficial. Because this compound was made to be an analog by changing the brominated pyrolle to an indole ring of a reported allosteric inhibitor of AtIspD, an x-ray crystal structure is available with the pentabromopseudilin bound. A logical next step is to use computational methods to dock HGN-340, as well as analogs of HGN-340 and compare docking scores as a means of designing new analogs. These can then be synthesized and tested.

HGN-333 did show activity against IspD, IspE, and IspF in antibacterial assays and showed significant antibacterial activity.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 6A: FOL7185; FIG. 6B: FOL 7082; FIG. 6C: FOL 7380; FIG. 6D: is a schematic of a number of binding sites of IspD, E, F in *T. gondii* (control).

FIG. 15C, Alignment of *Arabidopsis thaliana* IspD (PDBID 4NAK, light blue) with pentabromopseudlin(red) x-ray crystal structure and *Arabidopsis thaliana* IspD (PDBID 1W77, green) with cytidine-5'-monophosphate (dark blue). This shows the proximity of the allosteric binding site of pentabromopseudilin to the active site in a monomer of IspD.

FIG. 36: Preparation of 2-([1,1'-biphenyl]-3-yl)-5-(1H-indol-2-yl)-1,3,4-oxadiazole (HGN-287)

FIG. 55A, EcIspD HGN-211; FIG. 55B, EcIspD HGN-212; FIG. 55C, EcIspD HGN-213; FIG. 55D, EcIspD HGN-214; FIG. 55E, EcIspD HGN-215; FIG. 55F, EcIspD HGN-221.

FIG. 56B, EcIspD HGN-212; FIG. 56C, EcIspD HGN-213; FIG. 56D, EcIspD HGN-214; FIG. 56E, EcIspD HGN-215; FIG. 56F, EcIspD HGN-221.

DETAILED DESCRIPTION

Figure 1A:
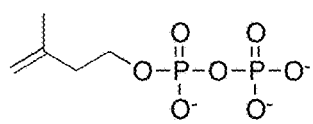
FIG. 1A-1B: Structures of Isopentenyl Diphosphate and Dimethylallyl Diphosphate-FIG. 1A Isopentenyl diphosphate and FIG. 1B dimethyallyl diphosphate, two products of the 2-C-methyl-D-erythritol 4-phosphate (MEP) pathway and the mevalonic acid (MVA) pathway.
Figure 1B:
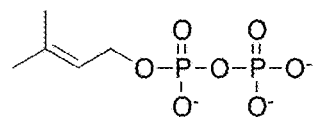
Figure 2A:
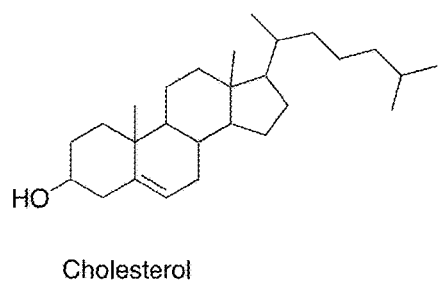
FIG. 2A-2D. Examples of Isoprenoid Compounds. Examples of Isoprenoid Compounds—Isoprenoids represent a large class of compounds derived from a common subunit. Some examples of common isoprenoids are FIG. 2A cholesterol (important component of cell membranes, FIG. 2B ubiquinone (involved in electron transport chain in mitochondria), FIG. 2C gibberellins (plant hormones that are involved in growth and development), and FIG. 2D beta-carotene (a precursor to vitamin A).
Figure 2B:
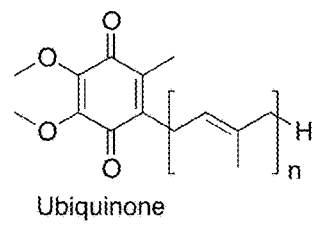
Figure 2C:
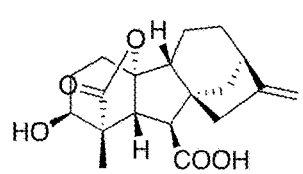
Figure 2D:
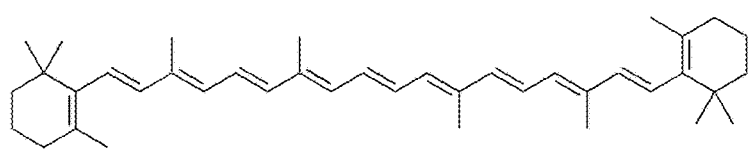
Figure 3:
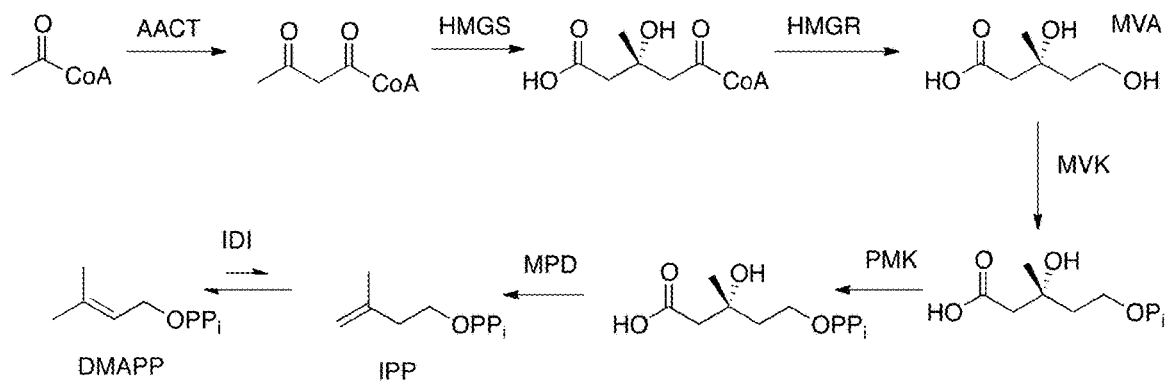
FIG. 3. MVA Pathway—The MVA pathway is utilized by mammals and other higher eukaryotes in synthesis of isoprenoid subunits IPP and DMAPP.
Figure 4:
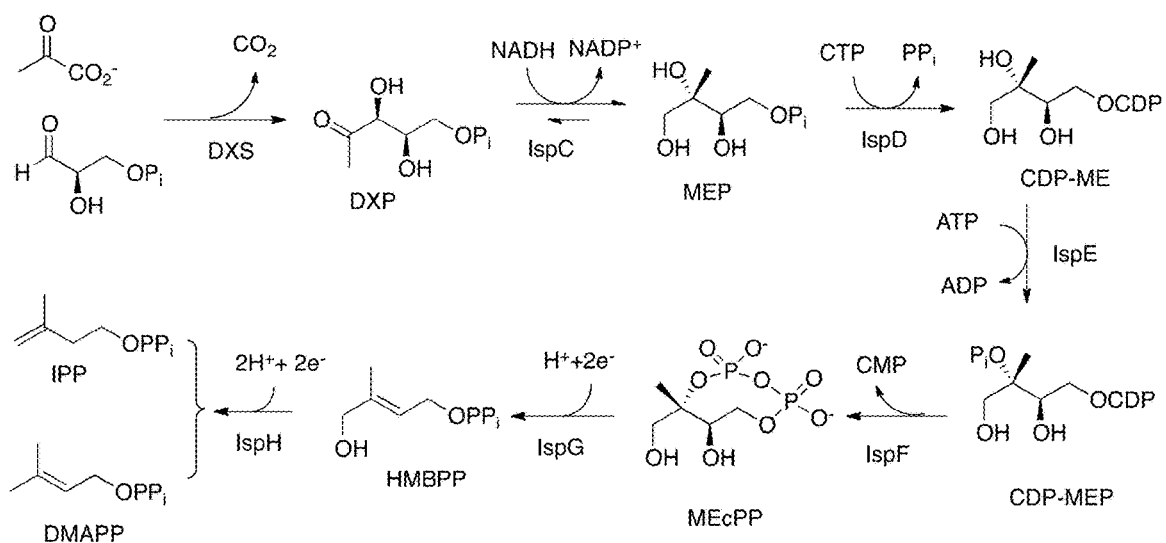
FIG. 4. MEP Pathway, an alternate pathway to the MVA pathway that is found in many bacteria, plants, and parasites such as malaria.
Figure 5:
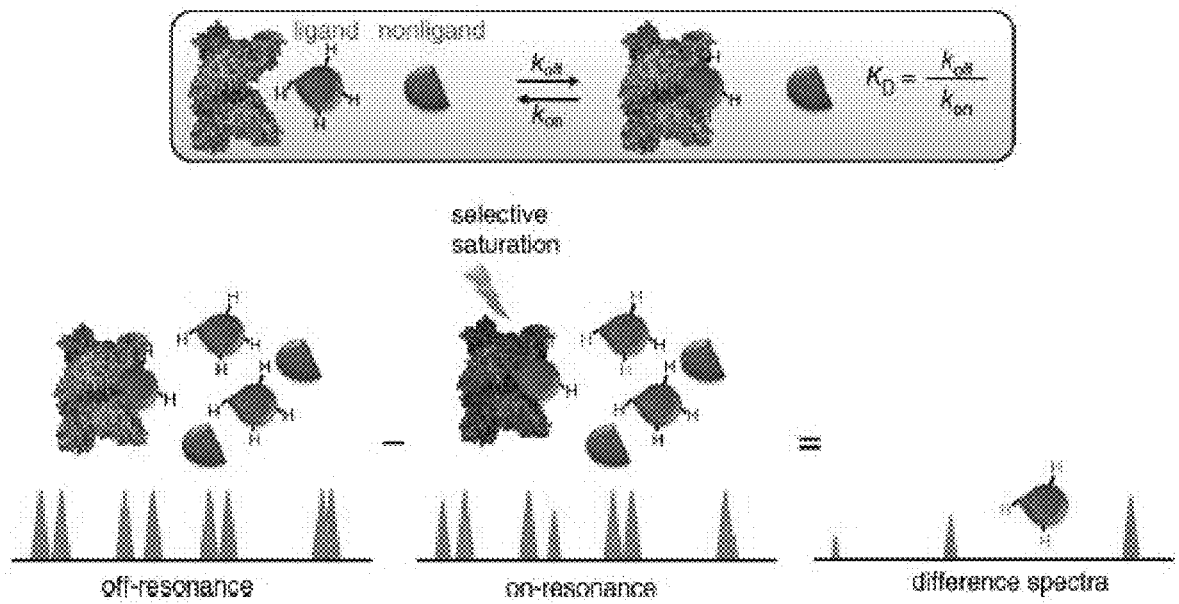
FIG. 5. Schematic of Saturation Transfer Difference NMR—Schematic of Saturation Transfer Difference NMR—A technique used to identify small molecules that bind to a protein through subtraction of the on-resonance spectra from the off-resonance spectra. The difference shows parts of the molecule that are involved in binding. Reprinted with permission from Viegas, A., et al. Saturation-Transfer Difference (STD) NMR: A Simple and Fast Method for Ligand Screening and Characterization of Protein Binding. *Journal of Chemical Education* 2011, 88, 990-994. Copyright 2011 American Chemical Society.
Figure 6D:
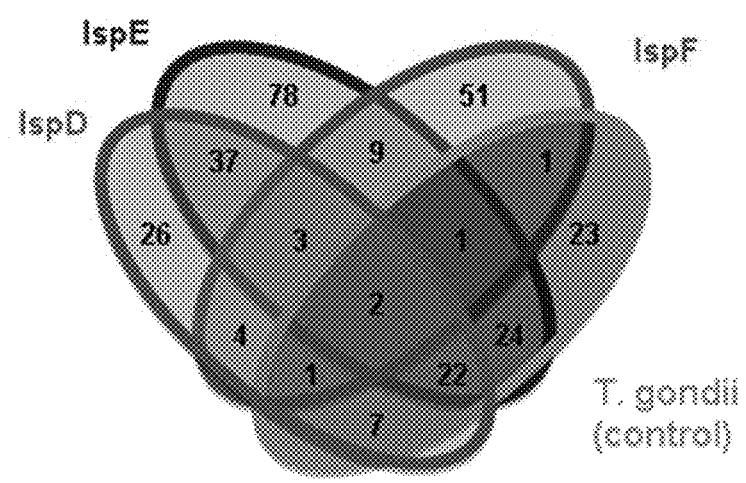
FIG. 6A-6D. STD-NMR Fragment Screening Results (SSGCID).
Figure 6A:
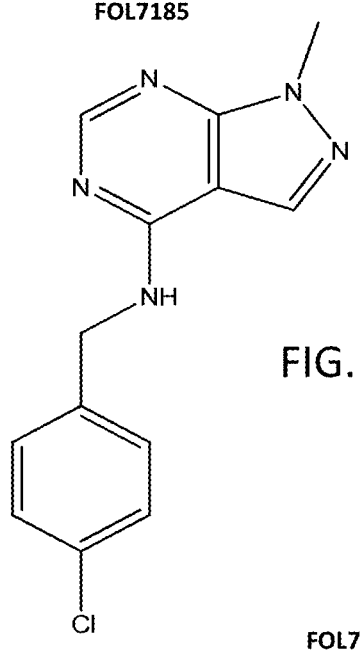
Figure 6B:
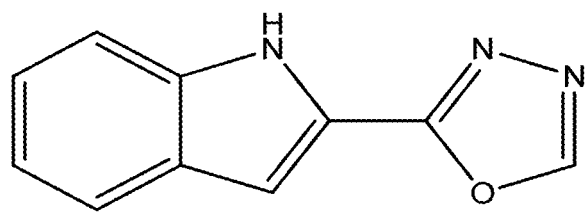
Figure 6C:
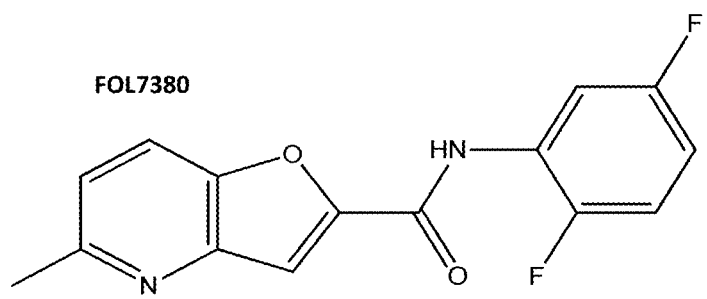
Figure 7:
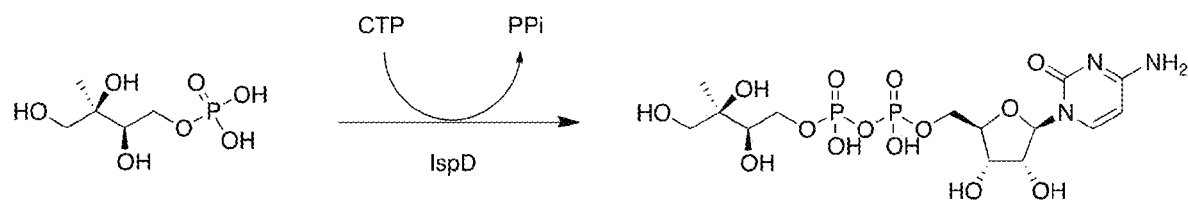
FIG. 7. IspD Reaction—IspD catalyzed transfer of CMP to MEP to form 4-diphosphocytidyl-2-C-methylerythritol.
Figure 8:
FIG. 8. X-Ray Crystal Structure of *Mycobacterium tuberculosis* IspD Homodimer with $Mg^{2+}$ (orange) and CTP (red) Bound; PDBID 2XWN.
Figure 9:
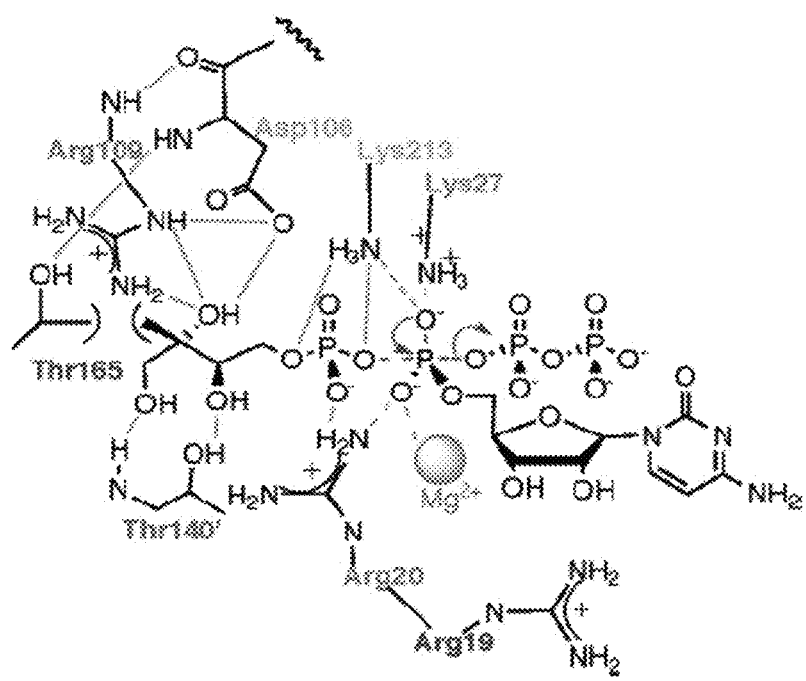
FIG. 9. Proposed Role of Amino Acids in Binding of MEP-cytidyltransferase Intermediate. Reprinted with permission from Richard, S. B., et al. Kinetic Analysis of *Escherichia coli* 2-C-Methyl-d-erythritol-4-phosphate Cytidyltransferase, Wild Type and Mutants, Reveals Roles of Active Site Amino Acids. *Biochemistry* 2004, 43, 12189-12197. Copyright 2004 American Chemical Society."
Figure 10:
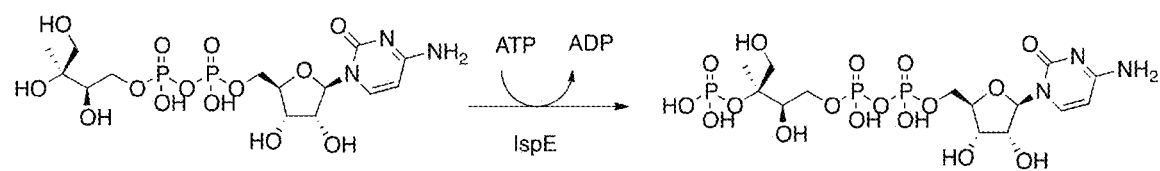
FIG. 10. IspE Reaction—IspE catalyzed transfer of phosphoryl group from ATP to 4-diphosphocytidyl-2-C-methylerythritol to form 4-diphosphocytidyl-2C-methyl-D-erythritol 2-phosphate.
Figure 11:
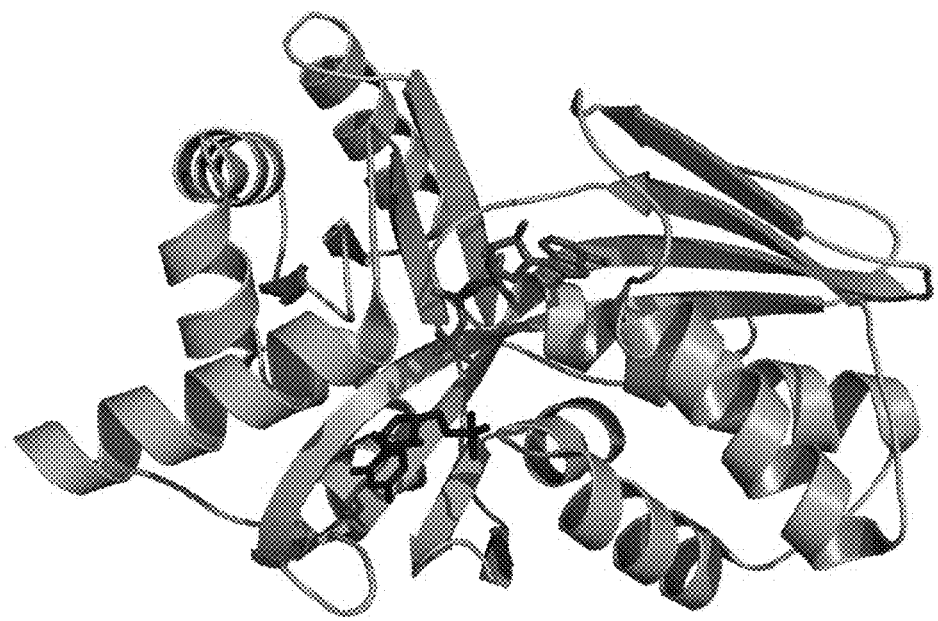
FIG. 11. X-Ray Crystal Structure of *Mycobacterium abscessus* IspE with ATP (red) and CMP (blue) Bound to Active Site; PDBID 4DXL.

The 2-C-methyl-D-erythritol-4-phosphate pathway, or MEP pathway, has recently gained attention as being a prime target for inhibition of many pathogenic species due to the lack of analogous enzymes in humans and many higher eukaryotes that use the mevalonic acid pathway. Either the MEP pathway or mevalonic acid pathway are utilized by all living organisms to generate the molecules isopentenyl diphosphate, IPP, and dimethylallyl diphosphate, DMAPP, which in turn can be used to create a wide variety of necessary cellular components called isoprenoids, such as cholesterol, some vitamins, pigments. The MEP pathway involves seven different enzymes, which are unique in the cellular machinery. Each is a potential target for inhibition by small molecules that could prove to be fatal to the organism.

In an NMR based screening of the Fragments of Life library, the fragment FOL7082 was one of thirty-seven compounds that bound to both IspD of *Mycobacterium paratuburculosis* and IspE of *Mycobacterium abscessus*. The fragment hit FOL7082 was optimized using a Topliss Tree approach to generate a small library of analogs that were tested in a variety of biological assays. Synthesis of this library was performed using a reaction scheme that allowed for a high number of analogs to be made from the same starting material with only variation of the carboxylic acid used. Further changes to FOL7082 were made by incorporating different heterocycles in place of the indole, such as benzothiazole and benzimidazole, to test if there was an increased activity against enzymatic targets IspD and IspE.

Overall, analogs of the original fragment hit, FOL7082 were synthesized that resulted in a greater than 20-fold increase in activity against enzyme target IspD. Analogs showed some antibacterial activity as well as herbicidal activity through inhibition of germination. The project was successful in taking a fragment hit with no measurable activity to a compound with 50 μM activity against IspD.

A goal was to discover novel hit compounds targeting IspD or IspE for *E. coli* and *B. thailandensis*. Currently, there are very few known inhibitors of either IspD or IspE with most possessing $IC_{50}$ values in the millimolar range.

The biophysical properties of IspD and IspE were investigated to aid discovery of novel inhibitors. Saturation transfer difference nuclear magnetic resonance (STD-NMR) fragment screening identified several fragments that bound to both IspD from *Mycobacterium* paratuberculosis and IspE from *Mycobacterium abscessus*. Analogs of these fragments aimed to target IspD and IspE. Thermal shift screening was used as a filter to identify a subset of compounds that bind to the IspD and IspE enzymes. High throughput thermal shift screening of the MicroSource Spectrum library against EcIspD revealed several potential hits, which were subsequently investigated using a plate-based enzyme inhibition assay.

Results from the enzyme inhibition assays revealed a small set of compounds capable of inhibiting IspD activity. Follow-up studies were performed using isothermal titration calorimetry and enzymatic inhibition assays. Results from these studies have confirmed compounds with high micromolar inhibition targeting IspD from *Escherichia coli*. The IspE enzyme from both *Escherichia coli* and *Burkholderia thailandensis* were characterized with biophysical methods. Additionally, a plate-based enzyme inhibition assay was optimized to evaluate potential IspE inhibitors, which led to the discovery of several novel inhibitors ($IC_{50}$ values in the micromolar range). The identified compounds appear promising for future development of even more potent IspD and IspE inhibitors.

The high throughput thermal stability assays of EcIspD were used to assess binding potencies of over 2,700 biologically active and structurally diverse compounds that are either known drugs, experimental bioactive agents, or pure natural products. The compounds that had a thermal shift, indicating some interaction, were evaluated further with an enzymatic assay to determine activity against EcIspD. Finally, the same techniques were used to study IspE from both *E. coli* and *B. thailandensis* with the focus of future inhibitor design.

To expand the development of novel chemical matter, beyond what was identified using NMR screening, compounds were evaluated for binding activity against IspD using a thermal shift assay a library of compounds. The MicroSource Spectrum collection contains about 2,500 compounds of known drugs and natural products. Initial thermal shift results showed stability shifts for 48 compounds, both positive and negative shifts with a range of +3.53° C. (thimerosal) to −13.53° C. (cadmium acetate). Compounds were evaluated further using the enzymatic activity assay, which revealed a few compounds with high micromolar activity: isoliquiritigenin ($IC_{50}$=279±12 µM), thimerosal ($IC_{50}$=381±12 µM), and carnosic acid ($IC_{50}$=794±100 µM). While these activities are not very potent, they are more potent than the known *E. coli* inhibitors which could be used for future development for more potent inhibitors.

Initial thermal stability studies provided insight on the melting points of *E. coli* and *B. thailandensis* IspD. A thermal shift assay is an efficient and cost effective way of evaluating a series of compounds as an initial filter to determine which were evaluated further for enzymatic activity. Current inhibitors of Ec IspD mimic the substrate, such as fosmidomycin. NMR fragment screening of the Fragments of Life library against IspD from *Mycobacterium* paratuberculosis and IspE from *Mycobacterium abscessus* showed 102 compounds bound IspD and 176 compounds bound IspE. Of these known binders, 37 compounds bound to both IspD and IspE. One of those fragments that bound to both IspD and IspE is the base of the oxadiazole series which was studied with the thermal shift assay against Ec IspD. A significant shift in the thermal stability was not shown. Another class of fragment hits for both enzymes was the pyrazolopyrimidines, which again showed no significant thermal stability shifts. Most of these compounds were evaluated further using an enzymatic activity assay. These compounds showed weak to no activity against EcIspD. Isothermal titration calorimetry revealed that the reactant CTP binds with weak affinity to EcIspD, which could indicate why compounds have such a weak affinity for IspD.

Similar to IspD, IspE was analyzed and characterized using the same techniques against the pyrazolopyrimidine series and oxadiazole series of compounds. Thermal shift results against *B. thailandensis* ranged from +5.5° C. (pyrazolopyrimidine with furan functional group) to −4.5° C. (pyrazolopyrimidine with dichlorobenzene). An enzymatic assay was developed and optimized to evaluate the IspE against *E. coli* and *B. thailandensis* further revealing several compounds in the low micromolar range. The pyrazolopyrimidine series only showed a few compounds in the high micromolar range, however the oxadiazole series proved more fruitful for a range of activity from high to low micromolar. The most potent compound for both species was HGN-333, an oxadiazole with a 2,4-chloro benzene with an $IC_{50}$ for *E. coli* and *B. thailandensis* of 3.0±0.3 and 28.0±6.5 04, respectively. This compound is an ideal candidate for further development of more active compounds.

Example A—Biochemical and Structural Characterization of Ispd and Evaluation of Inhibitors There is a great need for discovering new inhibitors of this enzyme due to the lack of potent inhibitors, specifically against *E. coli* and *B. thailandensis*. Binding activity along with enzymatic activity of compounds can be determined with a variety of methods but each has limitations, consequently, the use of multiple techniques often proves most useful. Thermal stability assays, isothermal titration calorimetry, and enzymatic activity assays were used to assess potential small molecule inhibitors. Thermal stability assays give insight of how compounds may influence protein stability due to ligand interactions. However, thermal stability assays do not provide information on the location of the binding site, nor does binding equate to inhibition of enzymatic activity. Isothermal titration calorimetry (ITC) can provide the thermodynamic parameters of the ligand-enzyme interaction, including K, $\Delta G°$, $\Delta H°$, $\Delta S°$, and the binding stoichiometry. However, as with most techniques, the ability to obtain weak binding affinity dissociation constants ($K_D$ values in mM range) with ITC it is limited by the small molecule solubility, as well as the amount of sample required per titration. Finally, enzymatic inhibition activity assays reveal the key property, the ability of a compound to inhibit the enzyme. Such assays can also be run in a high throughput fashion, however, limitations arise due to the expensive substrates and timely experiments. A series of compounds against IspD from *E. coli* and *B. thailandensis* were based off fragment hits from a STD-NMR screening performed by Dr. Darren Begley (SSGCID).

This technique studies the interactions between proteins and ligands with the Nuclear Overhauser Effect (NOE) by selectively saturating protons within the protein without the ligand which creates a reference spectrum. If a ligand binds to the protein, spin diffusions will cause the saturation to disperse to the ligand, which would reduce the signal. Subtracting the resulting spectrum from the reference spectrum provides a spectrum for the binding ligands showing which portion of the ligand are interacting with the protein.

Results

Circular dichroism thermal stability studies of IspD for both *E. coli* and *B. thailandensis* have shown IspD has melting temperatures suitable for thermal shift assays. Thermal shift assays were performed on potential inhibitors from the pyrazolopyrimidine and the oxadiazole series which were designed off the fragment hits from the STD-NMR screening. The thermal shift studies did not show any significant stabilization or destabilization caused by the compounds on IspD. There are several reasons why there was no observed stabilization changes to the IspD enzyme. These thermal shift assays were performed against a different species of IspD compared to the binding studies of the STD-NMR screening which was performed against *M. tuberculosis*. Another possibility is that the thermal shift assay compound concentration was 40 µM which could be too low of a concentration to show any stabilization or destabilization to the enzyme considering known inhibitors bind to the active site in the millimolar range. An enzymatic assay was optimized for Ec IspD to evaluate several of the compounds to determine if any have any inhibition activity, however there was no significant activity shown. ITC results of Bt IspD with CTP revealed weak binding to the cofactor. This weak binding could indicate why the known inhibitors have such a weak $IC_{50}$ values against IspD.

Example B: Discovery of Small Molecule Enzyme Inhibitors of *E. Coli* Ispd Via High-Throughput Screening Within drug discovery, there are two main strategies for discovering hit compounds: knowledge-based design and random screening. Knowledge-based design is based on information of the target, which could be a known inhibitor or substrate that can be mimicked, or perhaps a crystal structure of a compound/protein complex. Conversely, random screening does not require prior knowledge of the target, and requires screening libraries of compounds with a variety of structures and bioactivity.

The MicroSource Spectrum library was screened using the thermal stability assay to evaluate 2,560 compounds which consists of 1040 drugs that have made clinical trials stage in the US, 240 international drugs that were marketed in Europe and Asia, and the remaining compounds are either natural products or derivatives of the other. The compounds that showed a shift in the stability of IspD were evaluated further using the EnzChek® enzymatic activity assay.

Thermal Shift Results

The library based screening technique in conjunction with the thermal shift assay was implemented to evaluate compounds from Spectrum collection. Out of the 2,560 compounds there were 48 hit compounds that displayed a change in the observed melting temperature, ranging from +3.53° C. (thimerosal) to −13.53° C. (cadmium acetate). Thimerosal (+3.53° C.) and Zinc Pyrathione (−7.72° C.) were evaluated further based on the clarity of the unfolding profile. Specifically, each compound was broken down into core structures to determine which portion of the compound affected the thermal stability. To study thimerosal, thiosalicylic acid and ethyl mercuric chloride were evaluated. The results of the assay revealed that the ethyl mercuric chloride portion of thimerosal affected the stability of the enzyme. Zinc pyrathione was simplified to 2-mercaptopyridine-N-oxide to determine if the zinc was the driving force for the destabilization of Ec IspD. Thermal shift results revealed that 2-mercaptopyradine-N-oxide did not have an effect on the thermal stability. Therefore, similar to the thimerosal, it appears that the metal is the prime factor on the stability of the enzyme.

EnzChek® Assay Results

The 48 compounds, which altered the stability of Ec IspD, were evaluated further with an enzymatic assay to determine potential inhibitory activity. Dose response curves found three compounds with $IC_{50}$ values in the high micromolar range. Thimerosal, which was used as a preservative in vaccines, showed an $IC_{50}$ of 381±12 µM. Isoliquiritigenin, a natural chalcone, has an $IC_{50}$ of 279±12 µM. Carnosic acid, a preservative in food, showed an $IC_{50}$ of 794±100 µM. The EnzChek® assay has a phosphate sensitivity of 2-150 µM. To ensure there is no interference caused by assay components, three standards were performed on each plate: buffer only, without CTP and without MEP. These standards confirmed that there was no phosphate contamination.

DISCUSSION

The screening of compound libraries is an invaluable tool for hit discovery. This technique allows screening against a wide variety of chemical structures, beyond the knowledge-based compounds developed. The MicroSource Spectrum Collection was evaluated against Ec IspD using the thermal stability assay, and 48 changes in stabilization were observed. The range of thermal shifts were from +3.53 (thimerosal) to −13.53 (cadmium acetate). Thimerosal and zinc pyrathione were selected for additional studies due to their unfolding profiles. Each of these two compounds were dissected, which revealed that the metals in the compounds were the driving force for the thermal stability change.

An enzymatic assay was performed against the 48 compounds that showed a stability change to determine if any had any activity against Ec IspD. Three compounds displayed inhibition in the high micromolar range: thimerosal (381±12 µM), isoliquiritigenin (279±12 µM) and carnosic acid (794±100 µM). Thimerosal, which shows modest activity against the Ec IspD, is a well-known organomercurial preservative that has been subject to much controversy of its toxicity, components its use has been greatly reduced over the years and some countries have banned its use entirely. This compound may not be ideal for future work. Carnosic acid, a three ring abietane found in rosemary, has shown to have antimicrobial properties and is commonly found in oral care products such as mouthwash and toothpaste. This compound, which also has modest activity, is not an ideal candidate for further investigation due to the catechol moiety which tends to create prolific binding properties, reducing specificity. Isoliquiritigenin, a chalcone found in licorice, has shown to have a wide array of properties from anti-cancer to anti-inflammatory activities. This compound would be the most ideal candidate, out of the three examined, to investigate further as possible lead compound.

Example C: Biochemical and Structural Characterization of Ispe and Evaluation of Inhibitors Currently, IspE has several known inhibitors in the low to mid micromolar range against *E. coli*, however there are no known inhibitors against *B. thailandensis*, making it an attractive target for novel inhibitor discovery.

The two chemical series that were identified from the NMR fragment screening, the pyrazolopyrimidines and oxadiazoles, were evaluated further using the thermal shift assay. An enzymatic assay was developed and optimized to study these compounds for activity against both *E. coli* and *B. thailandensis*. ITC will determine dissociation constants of promising compounds.

DISCUSSION

The two series of compounds: pyrazolopyrimidines and oxadiazoles, were studied against IspE using a series of assays to determine binding and activity. Thermal shift assays were performed to determine a potential change of stability to IspE from *B. thailandensis*. All but one of the pyrazolopyrimidines showed little to no significant shifts, only HGN-0377 (furan) having a +4.0° C. shift. Oxadiazoles showed to have a larger range of stability shifts with the largest shift of +6.5° C. which was HGN-0813 (standard). These compounds were evaluated with enzymatic assays to determine activity against both *E. coli* and *B. thailandensis*. Similar to the thermal assay, the pyrazolopyrimidines had very little activity against both species from the enzymatic assay. The oxadiazoles had greater activity with HGN-333 (2,4-dichloro) having an $IC_{50}$ of 3.0 μM against Ec IspE and 28.0 μM against Bt IspE. To ensure that this compound was not interfering with the luciferase, the reaction was run without the IspE which showed no change in the signal compared to the control containing all reactants minus the enzyme and a compound. ITC experiments also verify binding of HGN-333 showing a $K_D$ of 2.2E+06±1.5E+06 and a −TΔS of −17.8 kcal/mol which suggests that the reaction is entropically driven which agrees with predictions of lipophilic pockets.

Results of Biological Assay Evaluation of Topliss Tree Compound Set

1. Thermal Shift Assay

Thermal shift assays are often used to determine the relative binding efficiency of low molecular weight compounds to an enzymatic target through measurement of changes in enzyme melting point temperatures without the ligand and with the ligand present. Differential scanning fluorimetry (DSF), utilizes a fluorescent dye that interacts with hydrophobic residues in a protein, producing a fluorescent signal that is monitored over a temperature range where the protein unfolding occurs. As the protein unfolds, hydrophobic residues that were buried in the protein's three dimensional structure become exposed allowing new interactions with the dye molecule. In theory, a ligand that binds the protein's native state will increase the protein stability resulting in a higher temperature needed to unfold or denature the protein, resulting in a higher melting temperature, $T_m$. Limitations of the thermal shift assay are that the $\Delta T_m$ values represent relative binding efficiency and the values do not indicate how the ligand is binding, or for instance if the compound inhibits enzyme activity. Also, solubility of ligands in the buffered solution are limiting on the concentrations that can be tested, as seen in all assays. Thermal shift assays are very useful as a screening method and a means of evaluation of ligands for highly soluble fragments.

Compounds synthesized were tested in a thermal shift assay against *Mycobacterium paratuberculosis* IspD (MpIspD) and *Escherichia coli* IspD (EcIspD) as well as *Mycobacterium tuberculosis* IspD (MpIspD) and *Lycopersicon esculentum* IspE (LeIspE) and the results are shown in FIG. 50 and Table 1.

Overall, the results from the thermal shift data show that all compounds are showing a relatively low change in melting point. HGN-207 showed a 0.8° C. positive shift for MpIspD and HGN-211, HGN-208, HGN-241, and HGN-221 all had equal shifts or higher. HGN-211 used had a trifluoromethyl substituent on the oxadiazole ring and a 0.3° C. increase in melting point over HGN-207. A higher shift was seen with HGN-208 in which the substituent on the oxadiazole ring was a phenyl and when the phenyl was extended out by one methylene unit in HGN-221, the thermal shift was 1.5° C., the highest obtained against MpIspD. In EcIspD, many thermal shifts were negative, which may mean that the compounds were destabilizing the enzyme or interacting more with the dye molecules. Due to the large number of negative values, this data does not show a clear correlation to MpIspD thermal shift data. Similar results were seen with LeIspE data shown in Table 1. The thermal shift data for MtIspD shows the hit molecule, HGN-207, at a 1.5° C. positive shift and HGN-239, HGN-252, HGN-214, and HGN-336 all have equal or higher shifts. The highest shift seen was HGN-214 with a 1.8° C. positive shift in which the substituent is a 4-(trifluoromethyl)phenyl. Benzothiazole and benzimidazole analogs of HGN-214 did not show positive shifts as high however.

IspE Expression and Purification of *E. coli* and *B. thailandensis*

The Ec IspE gene in parent vector pET14b (obtained from Dr. Karen Meyers lab). The Bt IspE gene was obtained from the SSGCID (ButhA. 00725.a. A1) within the parent vector AVA0421. Each parent vector introduces the same antibiotic resistance and restriction sites as the IspD. Also, similar to IspD expression, the vectors were transformed into BL21 (DE3) competent cells. Both DNA sequences were verified through University of Chicago CRC-DNA sequencing facility. The transformed cells were grown on LB agar plates with 100 μg/ml of amp for selection of the expression plasmid, and a single colony was chosen to inoculate a five mL of LB (100 μg/ml amp). This five mL sample was incubated overnight at 37° C. while shaking at 235 RPM. A 50 mL LB (100 μg/ml amp) subculture was inoculated with the overnight culture. This subculture was grown at 37° C. with shaking (235 RPM) until reaching an $OD_{600}$ in a range of 0.5-0.8. Once at mid-log, the cell culture is induced with IPTG to a final concentration of 1.0 mM. The temperature is dropped to 20° C. and the cells were grown for 16 hours while shaking at 235 RPM. After the 16 hours, the bacterial cells were pelleted using centrifugation at 8,000 RPM for 15 minutes and stored at −20° C.

Purification for both species of IspE was performed as described for IspD. Affinity chromatography was executed using a HisTrap HP nickel affinity IMAC column (GE Healthcare Life Sciences) with a BioLogic LP (Bio-Rad Life Sciences) fast protein liquid chromatography (FPLC) system. Size exclusion chromatography performed with a Superdex 75 HiLoad 26/60 size exclusion column (GE Healthcare Life Sciences). Buffer systems were identical for all enzymes as described herein.

Thermal Stability Assays

All thermal stability assays were completed identical to IspD using circular dichroism and differential scanning fluorimetry.

Enzyme Inhibition Determination with Kinase-Glo® Luminescent Assay Similar to the EnzChek® enzymatic assay, determination of activity is fundamental for evaluation of inhibitor. CDP-ME undergoes phosphorylation by IspE and ATP, leading to the product CDP-MEP. The Kinase-Glo® assay follows the consumption of the reactant ATP. The ATP in conjunction with oxygen and beetle luciferin are catalyzed by luciferase with the cofactor of magnesium to produce oxyluciferin, AMP, carbon dioxide, pyrophosphate, and creates a luminescence signal. This luminescence is directly related to the amount of ATP within the reaction, as the reaction progresses, the ATP is consumed and the amount of luminescence is decreased.

All Kinase-Glo® reactions were run using the following conditions (all conditions are described in final concentrations): 60 mM NaCl, 5 mM $MgCl_2$, 20 mM HEPES, 1 mM DTT, 5% DMSO (for compound suspension), 0.01% BSA, 200 µM CDP-ME, 40 µM ATP, and either Ec IspE and Bt IspE. All but the substrate CDP-ME are combined and incubated with the compounds for 10 minutes, before the addition of substrate and incubation (45 minutes, with shaking, room temperature). After incubation, the Kinase-Glo® reagent was added in equal final volume and allowed to develop for 10 minutes. Luminescence was recorded via a Synergy 2 plate reader.

Reactions involving the compounds and Kinase-Glo® reagent are performed to verify that the compounds are not interfering with luciferase enzyme in the reagent itself. The oxadiazole series are similar to known luciferase inhibitors, which tend to resemble the substrate, beetle luciferin. Most of the oxadiazole series, the beetle luciferin and the resembling known inhibitor (D-luciferin, 6-methyl ether) all have the core structure of benzothiazole. However, the difference is that instead of the oxadiazole, the inhibitor and substrate have a dihydrothiazole.

ITC Binding Studies

All ITC experiments were performed under the same conditions as described herein. Compounds were dissolved in DMSO and brought to concentration with the dialysis buffer, with a maximum DMSO concentration of 10% by volume which was matched between ligand and enzyme, and centrifuged at 10,000 RPM for 10 minutes. The dialysis buffer was used for all sample dilutions to ensure buffers matching between the titrant and titrate, thus minimizing the excess heat due to buffer mismatch. ITC experiments were performed with IspE in the cell and ligand in the syringe. The initial injection volume was 2 µL (omitted) followed by 27 10 µL injections, every 240 seconds. Samples were run at 25° C., at pH 7.4, with a stirring speed of 307 RPM. Dilution runs were performed to allow determination of background heats caused by solution mismatch and instrument noise. Dilution runs were performed with ligand (at the same concentration as in the experiment run) in the syringe titrated into the dialysis buffer in the cell. Data were fit using OriginPro 7 with the ITC add-on by the manufacturer.

Expression of IspE for Both *E. coli* and *B. thailandensis* Results

IspE enzymes were purified using a nickel affinity column with a 20-500 mM gradient elution using imidazole. Fractions associated with the UV absorbance peak in the chromatogram, verified with a NanoDrop 2000c spectrophotometer (Thermo Scientific), were combined and concentrated to 10 mL using a spin concentrator. The resulting concentrate was further purified using a size exclusion chromatography column (Superdex 75 HiLoad 26/60), and fractions related to the UV absorbance peak of IspD were collected, combined, and concentrated.

Melting Point Determination of IspE

Circular Dichroism was used to determine the thermal stability of Ec and Bt IspE. Wavelength scans were run before the thermal melt to get a baseline reading which confirmed the mainly alpha helical secondary structure of the proteins. Full scans were repeated post-thermal melt to characterize the protein's reversibility. Both species show loss of secondary structure which may suggest the thermal unfolding to be non-reversible under the conditions of the experiment. The thermal stability of each of the proteins was observed at a single wavelength over a temperature range of 25-100° C. The melting temperature ($T_m$) was determined to be approximately 50° C. for Ec IspE and 46° C. for Bt IspE, which will be used as reference temperatures for further thermal shift assays.

Thermal Shift Results

Thermal stability assay performed as described herein. The range of melting point shifts for pyrazolopyrimidines are from −1.5° C. to +4° C. The range for the oxadiazole series was much more diverse with a range of −0.5° C. to +6.5° C.

Kinase-Glo® Enzymatic Assay Results

Pyrazolopyrimidines and oxadiazoles were evaluated in an enzymatic assay against both *E. coli* and *B. thailandensis*. The oxadiazole series, which were screened, have a structure similar to the luciferin reactant in the Kinase-Glo® reagent. To verify that the compounds are not interacting with the luciferase, involved in the secondary reaction which converts the beetle luciferin to oxyluciferin, a separate reaction is run sans enzyme.

This assay is performed with all reagents without enzyme and compounds concentration was 250 µM. This verification is necessary to ensure the inhibition values of the compounds are accurate. The assay results revealed only a few compounds in the pyrazolopyrimidine series possessed inhibition activity with $IC5_0$ values in the high micromolar range. The oxadiazole series showed a greater range in activity from low to high micromolar with the greatest activity being from compound HGN-0333 at 3±0.3 µM for *E. coli* and 28±6.5 µM for *B. thailandensis*.

Binding Studies of Bt IspE with HGN-0333

ITC studies were performed to observe the dissociation constant along with thermodynamic properties of the oxadiazole compound HGN-0333 with Bt IspE. The experiment showed a binding stoichiometry of 0.903 which would indicate that for each monomer there is one molecule of HGN-0333. The $\Delta H°$ of HGN-0333 showed to have a value of −8.6 kcal/mol and an entropic contribution of −T$\Delta$S of −17.8. $K_{D\ app}$ of HGN-0333 was shown to be in the nanomolar range.

2. Lettuce Leaf Assay

The lettuce leaf assay is a qualitative assay used to determine the relative effectiveness of the test compounds at inhibition of germination of seeds and root development as well as causing bleaching of leaves. Isoprenoid synthesis is vital in plants as isoprene-product gibberellins are a class of growth hormones in plants responsible for stimulating cell elongation and division. In addition, some carotenoids are involved in photosynthesis as components of the electron transport chain. MEP pathway inhibitors have the potential to prevent synthesis of these necessary cellular components and growth hormones resulting in inhibition of germination and root development as well as causing chlorosis, or bleaching in the leaves. The lettuce leaf assay, explores the effects of compounds as potential MEP pathway inhibitors by evaluating the effect on bleaching, root development, and germination of lettuce seeds, which all rely on isoprenoid biosynthesis. This assay does not directly identify MEP pathway inhibitors but is used as a supplemental assay to enzymatic inhibition assays. The assay is a qualitative assay and the effects are given rankings from 0 (no effect) to 5 (complete inhibition or bleaching). In this assay, compounds are dissolved in a volatile organic solvent and applied to filter paper in a petri dish. The solvent is allowed to evaporate and lettuce seeds are applied followed by the addition of 5 mL of water to obtain the necessary concentrations. Seeds are allowed to grow and they are observed on day 3 and day 4 for evaluation. The results are shown in Table 2.

From the lettuce leaf assay it is shown that HGN-207 did show inhibition of germination slightly and a fair amount of chlorosis. At a concentration of 1.0 mM, HGN-242 and HGN-223 showed the greatest activity at inhibiting germination of the lettuce seeds. A 4 in this case represents 80% of the seeds did not show any growth. HGN-214, which had an electron withdrawing group at the 4 position on the phenyl ring showed good inhibition of germination at 1.0 mM but not to the extent as when there is an electron donating group seen in HGN-242 and HGN-223. Many compounds were tested at a maximum concentration of 0.3 mM due to solubility issues. In these cases, DMSO stock solutions were made and diluted to a maximum of 1% DMSO in water. Because of this lower concentration and low water solubility, the data may not be representative of the compounds ability to inhibit MEP pathway enzymes as they may not have been able to pass into the lettuce seeds.

3. ISPD Assay (FIG. 55A-55F and FIG. 56A-56F)

Compounds were tested against IspD from *Escherichia coli* and *Plasmodium falciparum*. The assay measured activity through monitoring phosphate levels released by IspD enzyme over time using conditions published previously. The assay utilized the EnzCheck phosphate assay kit to quantify phosphate released by IspD. Reactions were done in a 96-well plate with each well containing a final volume of 50 µL. Concentrations of reagents were as follows: 100 mM NaCl, 25 mM Tris at pH 7.0, 7.5 mM MgCl$_2$, 1 mM dithiothreitol, 1 U/mL purine nucleoside phosphorylase, and 0.1 U/mL yeast inorganic pyrophosphatase, 50 µM CTP, 500 µM MEP, 0.1% DMSO, and 0.2 mM 2-Amino-6-mercapto-7-methyl puring riboside. Reactions with EcIspD used 2 nM EcIspD and reactions with PfIspD used 50 nM PfIspD. Reactions involved pre-warming the enzyme and buffers to 37° C. with different inhibitor concentrations followed by the addition of the purified MEP substrate. Absorbance was measured at 360 nm over time and values were used to create regression analysis curves from three trials and values were converted to (µM MEP)(µM enzyme)$^{-1}$s$^{-1}$ using a standard phosphate curve. These values were then used to identify percent activity compared to enzyme activity without the inhibitor. Results are indicated.

Figure 51A:
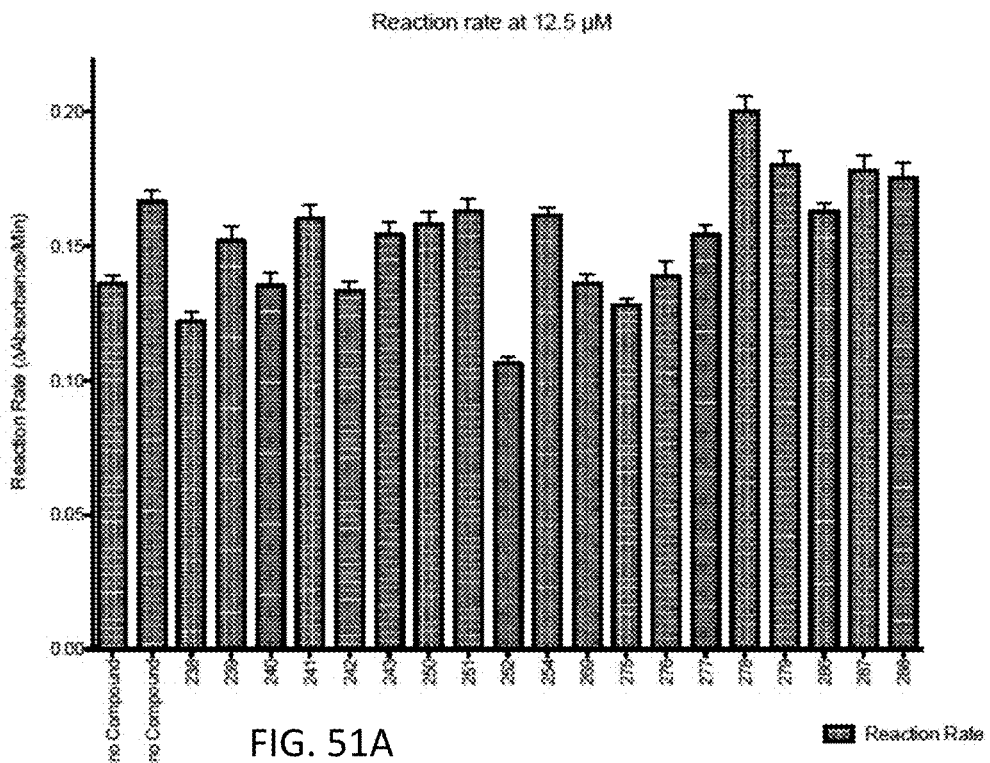
FIG. 51A-51B. Results from Washington University School of Medicine IspD Assay (Dr. Audrey Odom)—Results are shown as a inhibition curve where the x-axis represents compound concentration and the y-axis represents % activity of IspD enzyme. Data is also represented in a bar graph representing reaction rate of IspD at FIG. 51A, 12.5 and FIG. 51B, 100 μM compared to IspD without inhibitor.
Figure 51B:
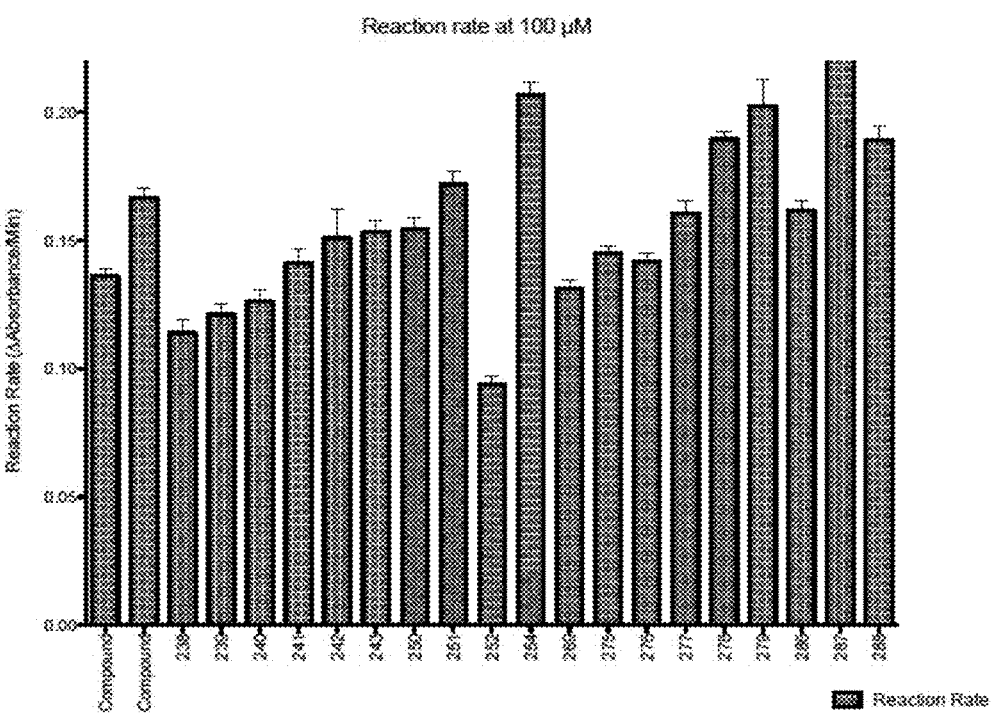

Results of the IspD assay show that most compounds tested were inactive up to 100 µM against *E. coli* IspD and *P. falciparum* IspD enzymes as indicated in the bar graph of FIG. 51. The only compound that showed significant activity was HGN-252 with a cyclopentyl substituent at both 12.5 and 100 µM concentrations. From the raw data, it appears that HGN-213 and HGN-214 from both *E. coli* IspD and *P. falciparum* IspD show some activity. The plot from *E. coli* IspD for HGN-214 had significant noise but there is a clear decrease in enzyme activity at higher concentrations. A significant decrease in activity was seen as well with HGN-213 and HGN-214 against *P. falciparum* IspD with IC$_{50}$ values approaching 100 µM. (FIG. 51A-51B)

4. Enzymatic Inhibition Assay from University of Hamburg

Figure 52:
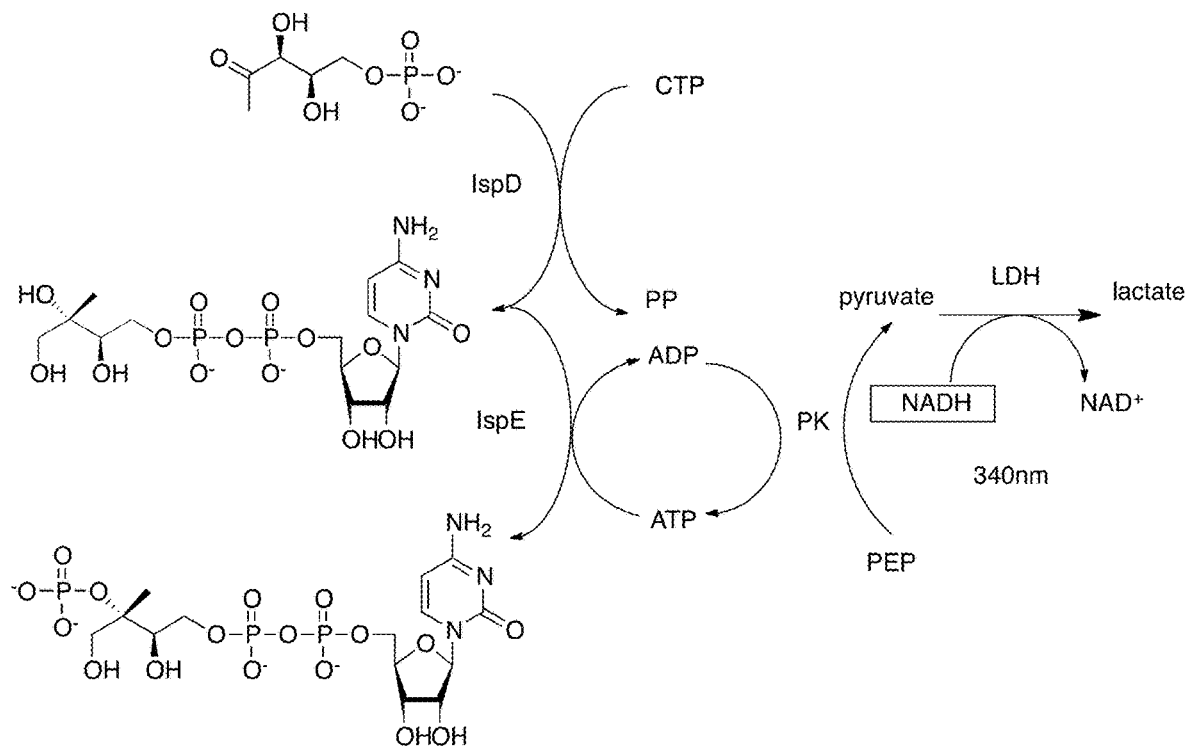
FIG. 52. Reaction Scheme for University of Hamburg Assay Against IspD-Reaction scheme involves coupled reactions that allow consumption of NADH to be monitored at 340 nm to assess reaction rate.
Figure 53:
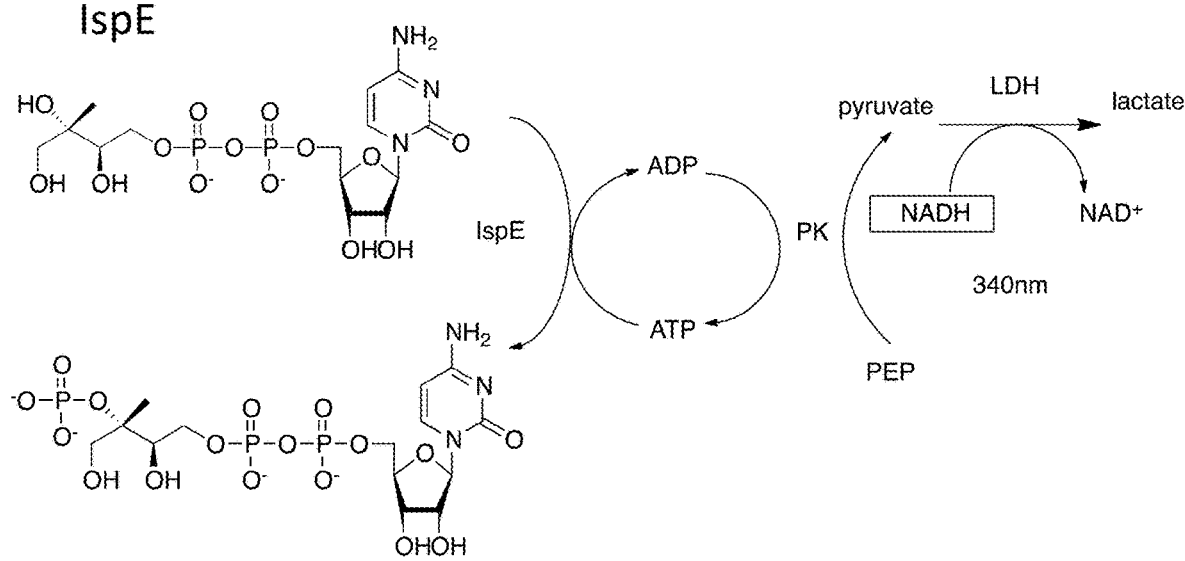
FIG. 53. Reaction Scheme for University of Hamburg Assay Against IspE-Reaction scheme involves coupled reactions that allowed consumption of NADH to be monitored at 340 nm to assess reaction rate.
Figure 54:
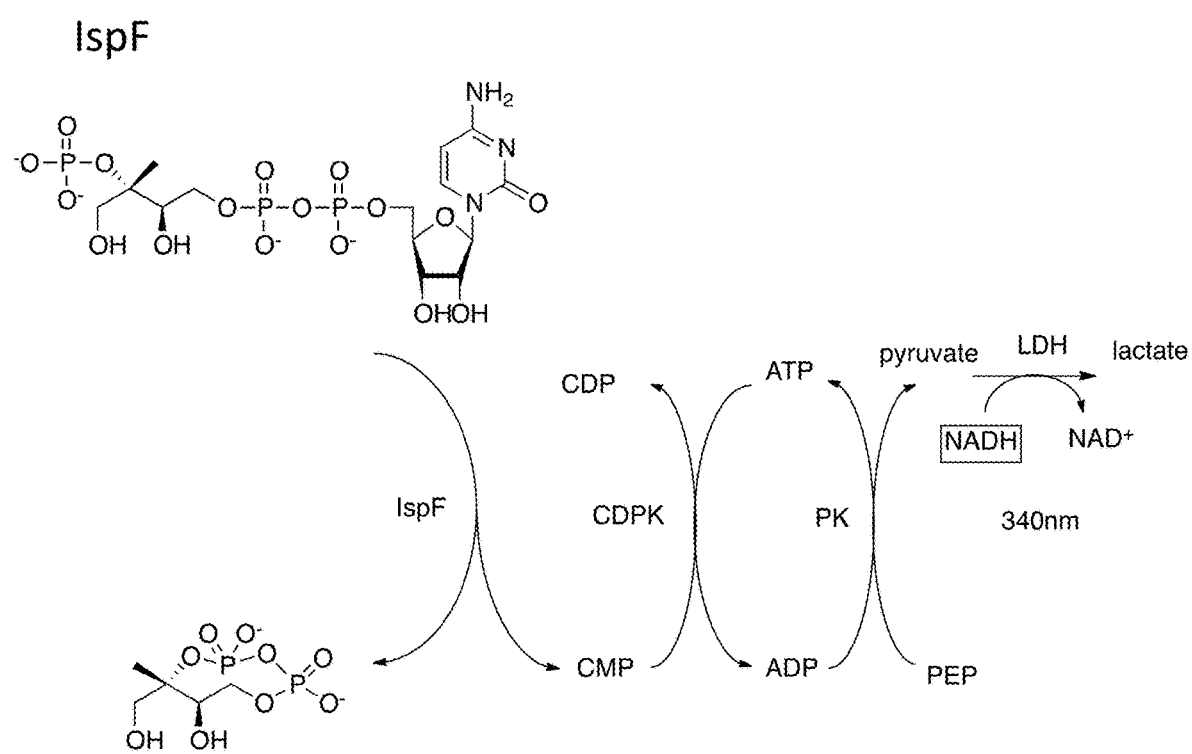
FIG. 54. Reaction Scheme for University of Hamburg Assay Against IspF-Reaction scheme involves coupled reactions that allowed consumption of NADH to be monitored at 340 nm to assess reaction rate.
Figure 55A:
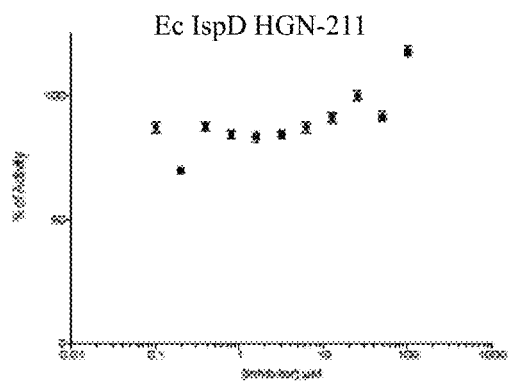
FIGS. 55A-55F. Results of an IspD assay on *E. coli*.
Figure 55B:
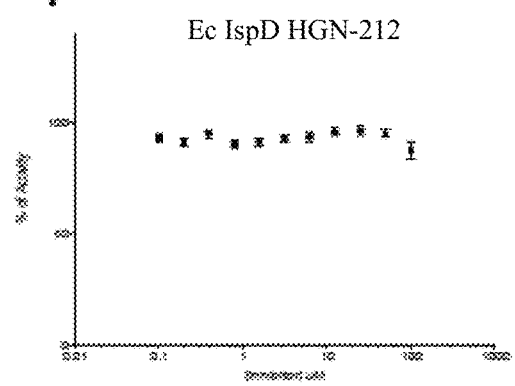
Figure 55C:
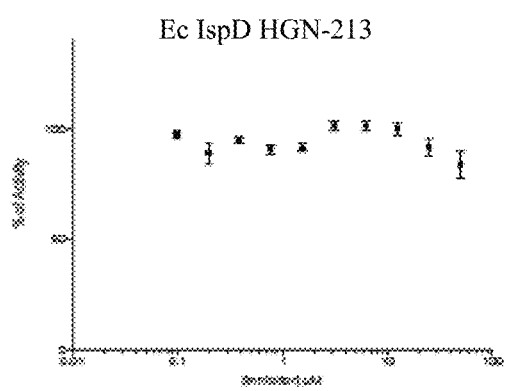
Figure 55D:
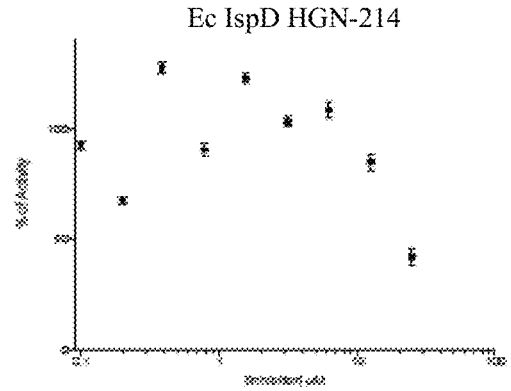
Figure 55E:
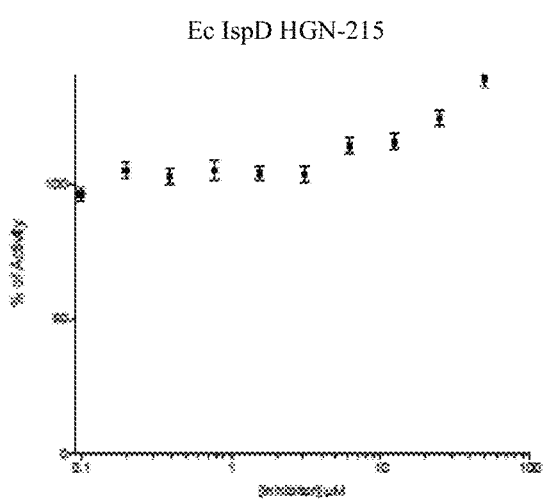
Figure 55F:
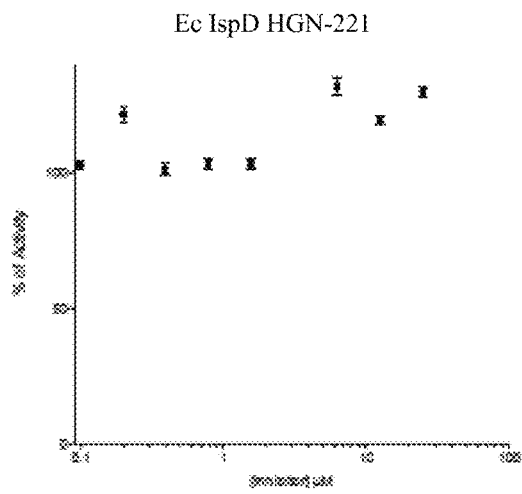
Figure 56A:
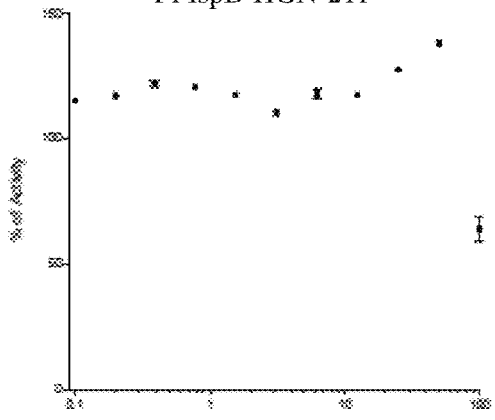
FIGS. 56A-56F. Results of an IspD assay on *P. falciparum*: EcIspD HGN-211.
Figure 56B:
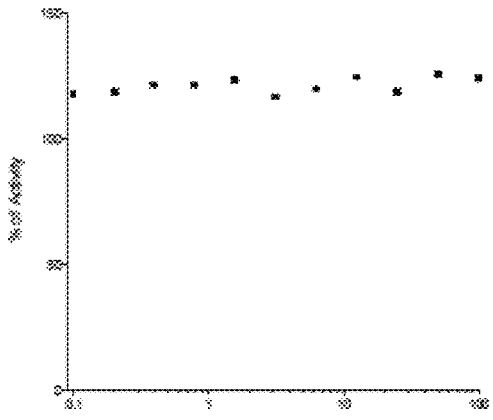
Figure 56C:
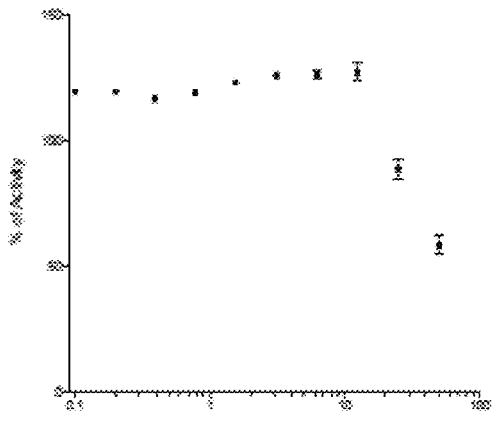
Figure 56D:
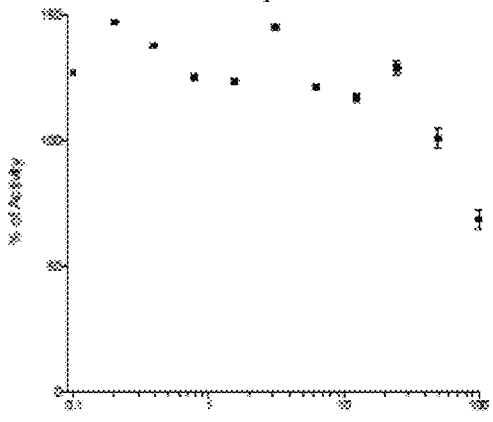
Figure 56E:
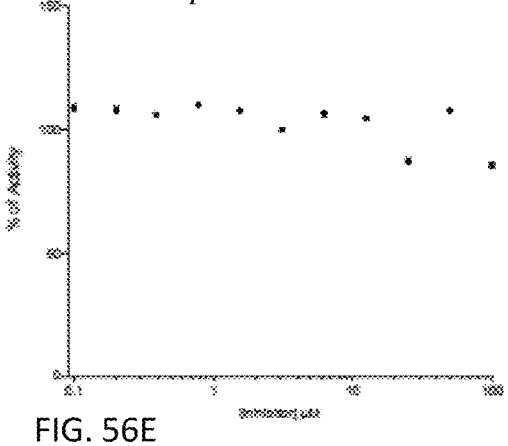
Figure 56F:
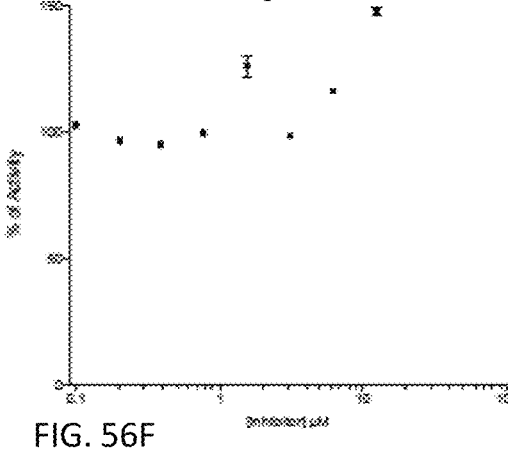

Compounds were subjected to a photometric enzymatic assay to test for inhibition of the plant enzymes *Arabidopsis thaliana* IspD and IspF, and IspE from *Lycopersicon esculentum*. The assay done was by using a coupled reaction scheme shown in FIGS. 52-54.

The procedure for AtIspD enzymatic inhibition assay, was performed by making an assay mixture of 100 mM Tris hydrochloride at pH 8.0 with 10 mM MgCl$_2$, 1 mM dithiothreitol, 2.5 mM potassium phosphoenol pyruvate, 2.1 mM CTP, 2 mM ATP, 1 mM of (2R,3S)-2,3-dihydroxy-4-oxopentyl phosphate, 460 µM NADH, 1.1% (v/v) DMSO, 0.4 U IspE, 1 U lactate dehydrogenase, 1 U pyruvate kinase and 2.4 mU IspD in 180 µL of solution. Solutions were incubated at 27° C. and monitored photometrically. By preparing the assay mixture with a large excess of IspE compared to IspD, any inhibition of IspE by the test inhibitor would be insignificant compared to IspD and therefore the rate of the reaction is determined by IspD activity.

The IspE assay conditions were very similar to the IspD assay in which the assay mixture was composed of 100 mM Tris hydrochloride at pH 8.0 with 10 mM MgCl$_2$, 1 mM dithiothreitol, 2.5 mM potassium phosphoenol pyruvate, 2 mM ATP, 1 mM of 4-Diphosphocytidyl-2-C-methylerythritol, 460 µM NADH, 1.1% (v/v) DMSO, 2.4 mU IspE, 1 U lactate dehydrogenase, 1 U pyruvate kinase in 180 µL of solution. Solutions were incubated at 27° C. and monitored photometrically.

The IspF assay mixture conditions were as follows: 100 mM Tris hydrochloride at pH 8.0 with 10 mM MgCl$_2$, 1 mM dithiothreitol, 2.5 mM potassium phosphoenol pyruvate, 2 mM ATP, 1 mM of 4-diphosphocytidyl-2C methylerythritol 2-phosphate, 460 µM NADH, 1.1% (v/v) DMSO, 0.5 U CMP kinase, 2.4 mU IspF, 1 U lactate dehydrogenase, 1 U pyruvate kinase in 180 µL of solution. Solutions were incubated at 27° C. and monitored photometrically.

Results of the assay against AtIspD, LeIspE, and AtIspF are summarized in Table 3.

Data from Table 3 was the most compelling data obtained for the compound library as it provided clear IC$_{50}$ values with associated error. In Table 3, the parent compound HGN-207 did not show any measurable activity against AtIspD, LeIspE, or AtIspF. No significant activity increase was seen until HGN-254 showed an IC$_{50}$ of 322 µM against AtIspD. Changing the cyclohexyl group to a phenyl increased activity against LeIspE to 165 µM and no significant change in activity for AtIspD. The most potent compounds for the indole series were those in which the phenyl ring was substituted at the 4 position with an electron donating group such as methyl or methoxy as seen with HGN-242 and HGN-223, both having low 200 µM IC$_{50}$ values against AtIspD and low 100 µM IC$_{50}$ values against LeIspE. Changing the indole ring of HGN-242 and HGN-223 to a benzothiazole ring in HGN-338 and HGN-336 showed a significant loss in activity. The compounds HGN-213 and HGN-214, which showed activity in Dr. Audrey Odom's assay, had relatively low activity in the University of Hamburg enzymatic inhibition assay. HGN-213 had an IC$_{50}$ value of 490 µM against AtIspD and the benzothiazole analog HGN-339 showed an increase in activity to 158 µM and changing the benzothiazole ring to a benzimidazole in HGN-421 showed an even better activity at an IC$_{50}$ 88 µM.

Of particular interest are compounds HGN-333 and HGN-340. HGN-333 showed activity against LeIspE at 31 µM and AtIspD at 151 µM as well as AtIspF at 291 µM. This compound has significant error associated with these values due to solubility issues of the compound. The pseudilin-like compound HGN-340 had the best activity against AtIspD at 50 µM.

5. Antibacterial Assay

The results from an antibacterial assay are from a primary screening of compounds against nine different strains of bacteria. The test organisms included both gram positive and gram negative bacteria. The gram-positive bacteria included *Bacillus cereus* (BC), *Micrococcus luteus* (ML), *Mycobacterium smegmatis* (MS), *Corynebacterium xerosis* (CX), and *Corynebacterium pseudodiphtheriae* (CP). Gram negative bacteria included *Burkholderia thailandensis* (BT), *Klebsiella pneumonia* (KP), *Escherichia coli* (EC), and *Pseudomonas aeruginosa* (PA). The primary screening was performed by streaking pure cultures of the test organisms onto separate agar plates and then isolating a single colony from each plate and inoculating it into a 5 mL liquid broth. This broth was incubated overnight at 37° C. Each test organism was spread on a plate to inoculate the entire surface and edges. Five compounds were tested on each plate by adding dry compound to the plate, after which 5 µL of 5% DMSO was added to the spots. Plates were then incubated at 37° C. overnight and checked for bacterial growth and zones of inhibition around the compounds. Test compounds were given scores from 0-3 depending on their ability to inhibit growth. The results are shown in Table 4.

SAR Evaluation of Topliss Tree Set

Using FOL7082 (HGN-207) as a hit molecule in the fragment based STD-NMR screening, a fragment growing technique, utilizing the Topliss tree approach, was used. Three assays evaluated compound activity against enzymes of a variety of species. The thermal shift assay measured how well compounds stabilized the enzyme. Both enzyme assays provided $IC_{50}$ values, with plant enzymes tested by one IspD from both *Escherichia coli* and *Plasmodium falciparum* at Washington University. Also, two assay tested compound activity in vivo, which were done utilizing nine strains of bacteria and in a lettuce leaf assay.

Evaluating the SAR of the compound library is difficult as there is no X-ray crystal structure of IspD or IspE in complex with FOL7082 (HGN-207) to evaluate important interactions between the compound and the enzyme. A Topliss tree approach was taken to make deliberate changes and determine which were beneficial based on the activity seen in assay results. One enzymatic assay produced the most substantial results because the $IC_{50}$ values for each compound were determined for IspD, IspE, and IspF, and provide a direct comparison between compounds. Beginning with the original hit, HGN-207, the $IC_{50}$ was determined to be higher than 1000 µM. By substituting on the oxadiazole ring at the 5 position with alkyl groups to increase the lipophilicity by substituting a methyl group in place of hydrogen and growing the fragment with ethyl, isopropyl, t-butyl. Unfortunately, the upper limit to this assay was 1000 µM of compound. Most of the substitutions, whether made to increase lipophilicity or affect the electronics of the molecule, were at or above the 1000 µM limit while the cyclohexyl substitution had an $IC_{50}$ of 322 µM against *A. thaliana* IspD. This suggests that a bulky lipophilic group is beneficial.

Moving from a cyclohexyl group to a phenyl, the activity against IspD was not significantly affected but now there is a significant increase in activity against IspE, going from an $IC_{50}$ greater than 1000 µM to 165 µM. The three dimensional structure of HGN-208 is very planar with little flexibility. By extending the phenyl ring out in HGN-221 and HGN-215, IspD activity was lost and activity against IspE was diminished. Going back to HGN-208, analogs were made by adding substituents to the phenyl ring at different positions. Adding a chlorine to the 3 position on the phenyl ring resulted in a loss of activity against IspD but no significant change against IspE. When a chlorine was moved to the 4 position on the phenyl ring, activity was gained back but against IspD, the activity was not as high as the unsubstituted ring. Activity against IspE was also lower in the 4-chloro substituted phenyl compared to unsubstituted HGN-208. When the chlorine is changed to a trifluoromethyl, IspD activity is lost, indicating that a strongly electron withdrawing group negatively affects the activity for IspD. Substituting these electron withdrawing groups with electron donating groups at the 4 position such as a methyl group with HGN-242 and methoxy group with HGN-223, activity was significantly enhanced for both IspD and IspE. IspD activity was in the low 200 µM range and IspE activity was in the low 100 µM range for both HGN-242 and HGN-223.

Using the four, 4-substituted compounds that showed the best activity against IspD and IspE, analogs were made to determine how changing the indole ring to a different heterocycle might affect the activity. A benzothiazole series was first explored. HGN-339, the benzothiazole analog of HGN-213, had an increase in IspD activity, but IspE activity was lost. For the other benzothiazole analogs, activity was significantly lower compared to the indole series. A benzimidazole series was also explored with analogs of HGN-213 and HGN-214. The benzimidazole series showed a significant increase in activity for mostly IspD. The activity increased from 490 to 88 µM in moving from HGN-213 to HGN-421, and >1000 to 251 µM moving from HGN-214 to HGN-422. In both, there was not a significant change in IspE activity.

Compounds HGN-333, HGN-334, and HGN-335, were all made because they showed antibacterial activity in published reports with no indication of mechanism of action, but with structural similarities to active compounds. They were explored for activity against MEP pathway enzymes. Of particular interest is HGN-333, which showed significant activity against all three enzymes in the University of Hamburg assays, however, due to solubility issues, there was some concern about the true activity. However, it is noteworthy, as it did show a significant effect on IspE.

HGN-340 does not fit in with the typical structure of any previously tested compounds, but the Witschel group reported pseudilin compounds that showed good activity against IspD by acting as an allosteric inhibitor of the enzyme. HGN-340 was made as an analog of the pseudilin compound reported. In the enzymatic assay herein, it had the best activity of all the compounds tested, with an $IC_{50}$ value of 50 µM.

Comparing the results from the two enzymatic assays, the data is consistent with compounds HGN-213 and HGN-214 being the most active of the compounds tested. It can be noted that of the alkyl substituted compounds, HGN-252 showed the best inhibitory activity at both 12.5 and 100 µM concentrations and when that is compared to results from University of Hamburg data, it shows an inconsistency as HGN-254 had better activity in the University of Hamburg assay over HGN-252. This may be a result of differences in sequence homology between *E. coli* and *A. thaliana* IspD enzymes.

In the thermal shift assay, the results are more challenging to explain in terms of activity of the compound. The thermal shift data was collected against *M. tuberculosis* IspD and *L.*

*esculentum* IspE enzymes. In the thermal shift assay against IspD, HGN-214 had the highest positive shift in melting point of 1.8° C., but HGN-214 was inactive against AtIspD in one assay. However, the other assay showed that HGN-214 had the best activity against *E. coli* IspD. Differences between species may result in the inconsistent activities, especially if the compounds are acting as allosteric inhibitors as there is a likely a higher variability in sequence between enzymes outside of the active site. The thermal shift assay results provide insight into the relative binding affinity of ligands and while many produced a shift in the melting point of IspD, these changes are quite small, most likely indicating compounds are weak binders. In the thermal shift assay for IspE, most compounds produced a negative thermal shift. In theory, if a molecule binds to the enzyme, it should stabilize it producing a positive thermal shift. The negative shifts for LeIspE indicate that many compounds may have destabilized the enzyme, acting as a denaturant to some extent. LeIspE was used in both the thermal shift and one assay so the results should be comparable, but oddly, the only compound that showed a positive thermal shift was found to be inactive against LeIspE, and HGN-250 had a significant negative thermal shift with −2.75° C., but was inactive in one assay could have a significant effect. However, HGN-422 had the largest negative shift at −3.25° C. and showed fairly decent activity as well with an $IC_{50}$ value of 267 µM. HGN-422 wasn't the most potent compound against LeIspE in one assay.

In vivo assays are of particular interest when looking for potential antibacterial or herbicidal agents. The antibacterial preliminary screening, showed interesting results for a few compounds that show consistency with the current SAR. Most compounds tested showed no inhibition of bacterial growth amongst the nine species tested. From the University of Hamburg assay, HGN-421 was of particular interest because it had an $IC_{50}$ against IspD of 88 µM. HGN-421 and HGN-422 both showed slight antibacterial activity against *Burkholderia thailandensis* and *Mycobacterium smegmatis*. HGN-333, was moderately effective against *Pseudomonas aeruginosa* while HGN-335 was slightly effective. HGN-340, which had an activity of 50 µM in the University of Hamburg assay, was moderately effective against *P. aeruginosa* as well. This shows there is some consistency between the enzymatic assay and the antibacterial assay, but likely due to poor solubility of compounds in water, many may not have been able to enter bacterial cells, resulting in lower activities in the antibacterial screening.

A second in vivo assay was used to evaluate efficacy of compounds at inhibiting germination and root development in lettuce seeds or causing bleaching of the leaves. Results from this assay revealed that the parent compound HGN-207 caused significant bleaching and inhibition of germination at 1.0 mM and 0.5 mM. HGN-209 resulted in some inhibition of root development and germination also at 1.0 mM and 0.5 mM. Further substitutions resulted in a loss of activity against root development but many caused some inhibition in root germination, such as HGN-250 that caused a significant decrease in germination at 1.0 mM and most others resulting in slight inhibition.

Materials and Methods

Design of Compound Library
1. Topliss Tree Approach

Typically, the drug design process is a lengthy task in developing analogs of an initial hit molecule to ultimately reach a highly potent drug. Often times, thousands of compounds may be generated to optimize interactions of the hit molecule with the target. In the 1960s and 70s, the Hansch methods were developed to provide a rational approach for quantitative structure-activity relationships (QSAR) in a compound library. These methods helped determine which properties have significant biological activity input. Some properties of various substituents involve the hydrophobicity constant of that substituent, π, relative to hydrogen, the Hammett substituent constant, which gives a measure of the electronic properties of the substituent (electron withdrawing or electron donating), denoted as σ, and Taft's steric factor, denoted as $E_S$. Using these factors, a mathematical derivation of the relationship with the level of activity of analogs could allow for development of analogs likely to display enhanced activity.

Figure 12:
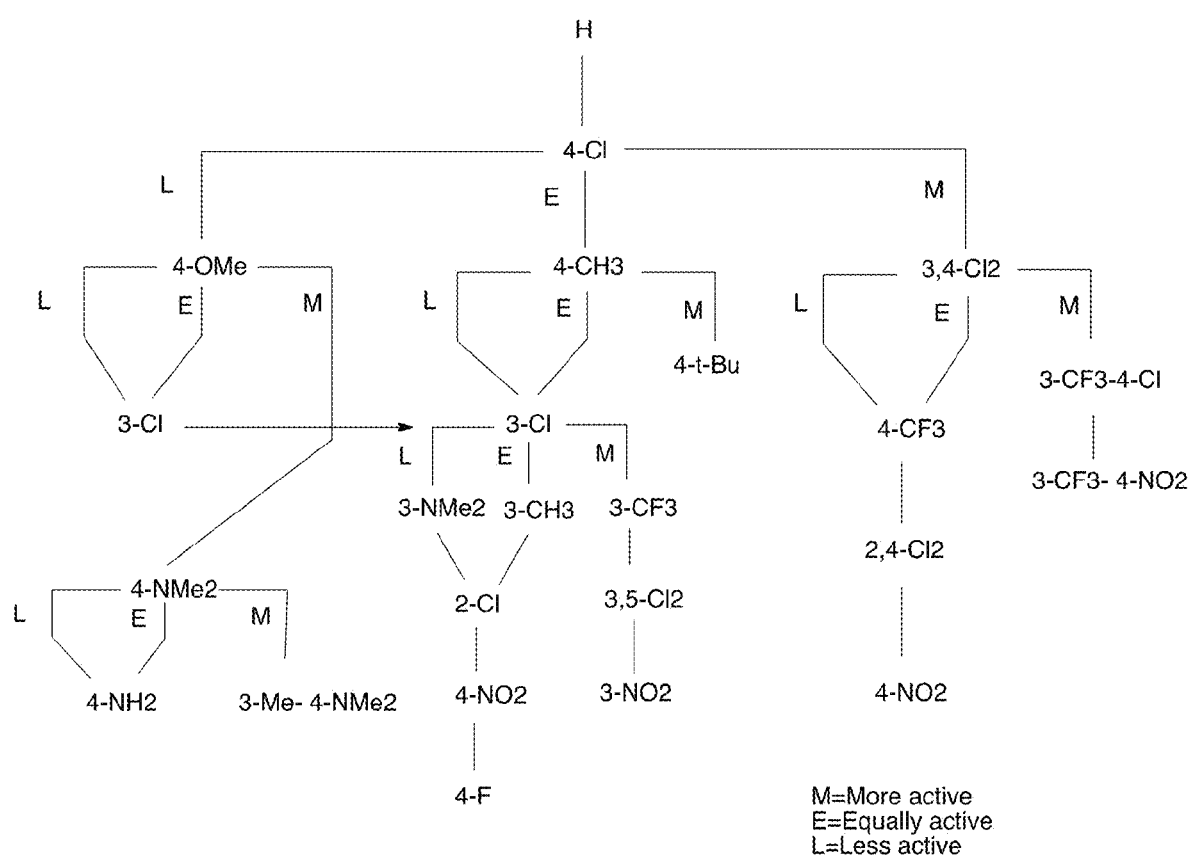
FIG. 12. Topliss Tree for Phenyl Substitutions—H designates an unsubstituted compound depending on activity of 4-Cl, different routes can be taken to obtain more potent compounds.
Figure 13:
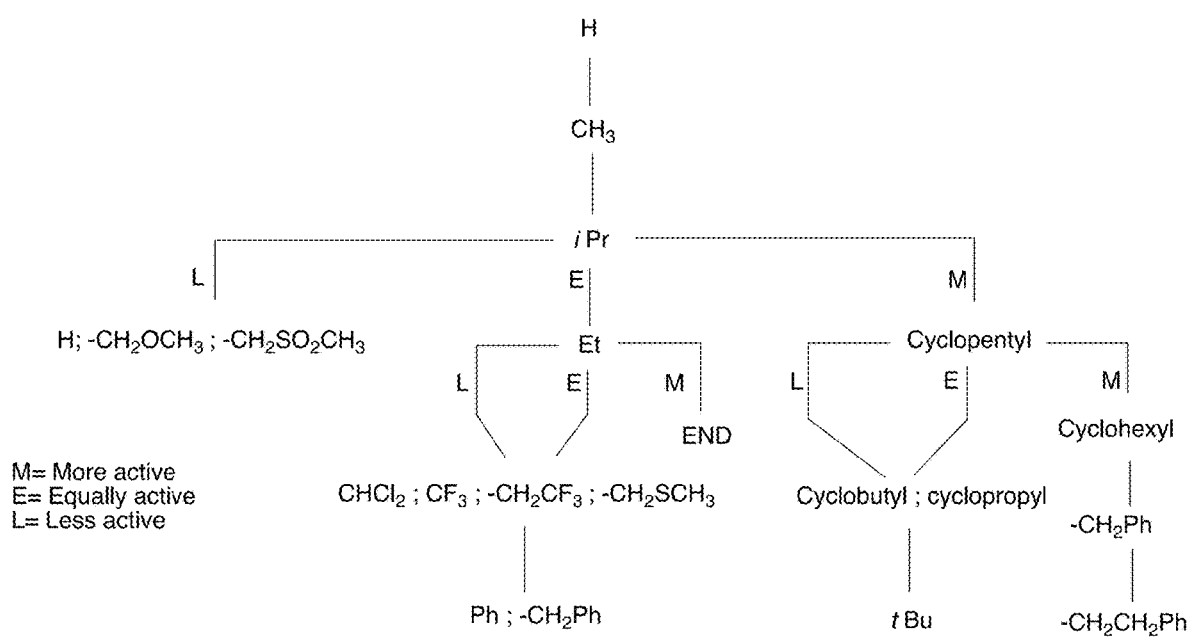
FIG. 13. Topliss Tree for Aliphatic Substitutions—H designates an unsubstituted compound and methyl is the first substitution followed by isopropyl. Depending on how moving from methyl to isopropyl affected the activity, the appropriate route of synthesis would be taken.

Professor J. G. Topliss developed a non-mathematical operation scheme in the 1970s that utilized the Hansch method parameters to progress rapidly to more potent compounds in a series of analogs. The non-mathematical scheme presented by Topliss became known as the Topliss tree (FIGS. 12 and 13). This stepwise method typically begins with an unsubstituted phenyl compound and a 4-chloro substituted phenyl analog or an unsubstituted parent compound in which aliphatic groups are added in place of hydrogen. In the case of phenyl substitutions, the 4-chloro substituent represents a +π value and +σ value because it is both lipophilic and electron withdrawing. The 4-chloro substituent is compared to the unsubstituted phenyl compound in potency and classified as less potent, equally potent, or more potent. If the compound is more potent, it can likely be attributed to a beneficial +π, +σ, or a combined effect. Therefore, a 3, 4-dichloro analog is synthesized next, as the +π and +σ effects are larger and could possibly lead to greater potency. However, if 4-chloro was equally as potent as the unsubstituted phenyl, then it is most likely attributed to a beneficial +π effect and but offset by a detrimental +σ effect, because typically increasing lipophilic character is better for small molecule binding affinity but the electron withdrawing effects may have been too large. Therefore, the next appropriate compound to make would be a 4-methyl substituted phenyl because this has a lipophilic character, +π, but it is also electron releasing, −σ. If the 4-chloro analog is significantly less potent than the unsubstituted phenyl, then it may be due to a steric interaction from the 4-substitution, or the activity is enhanced by a −π or −σ substituent (hydrophilic or electron donating). The most likely cause for the decrease in potency is due to a need for a −σ effect, so following the 4-chloro substitution, the next analog would be 4-methoxy due to its enhanced electron donating effect and only slightly enhanced hydrophilic character. A similar rational is used for the rest of the decision tree to designate different substituents on the phenyl ring. A similar scheme has also been applied to series with aliphatic side chain substitutions as well.

2. Design of Chemical Series

Without X-ray crystal structures of MpIspD and MaIspE with FOL7082 bound, it is difficult to make deliberate changes to the fragment to increase the binding efficiency. Therefore, the Topliss tree approach was taken utilizing the fragment FOL7082 as the core to develop a series of compounds to test for enzyme inhibition activity. The simplest method of generating a series of analogs was to determine which areas of the molecule would most suitable to change.

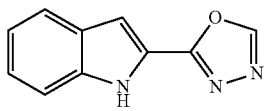

FOL 7082
2-(1H-indol-2-yl)-1,3,4-oxadiazole

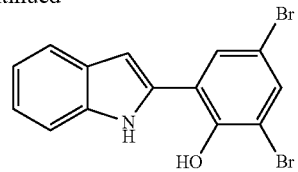

Figure 14A:
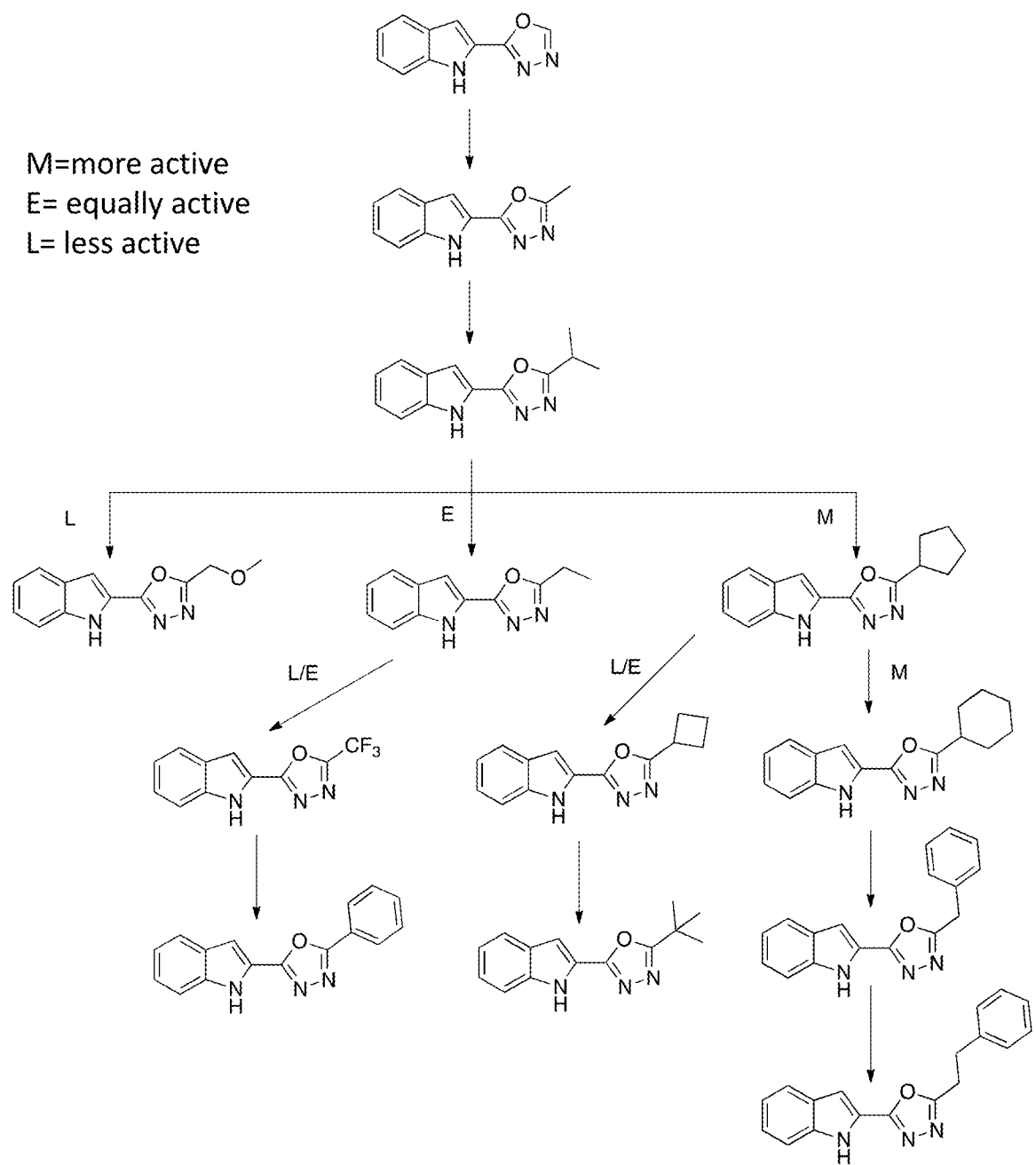
FIG. 14A-14B. Topliss Tree Sets for FOL7082. Compound set was designed by following the Topliss Tree scheme beginning with FOL7082, unsubstituted at the 5 position on the 1,3,4-oxadiazole ring.
Figure 14B:
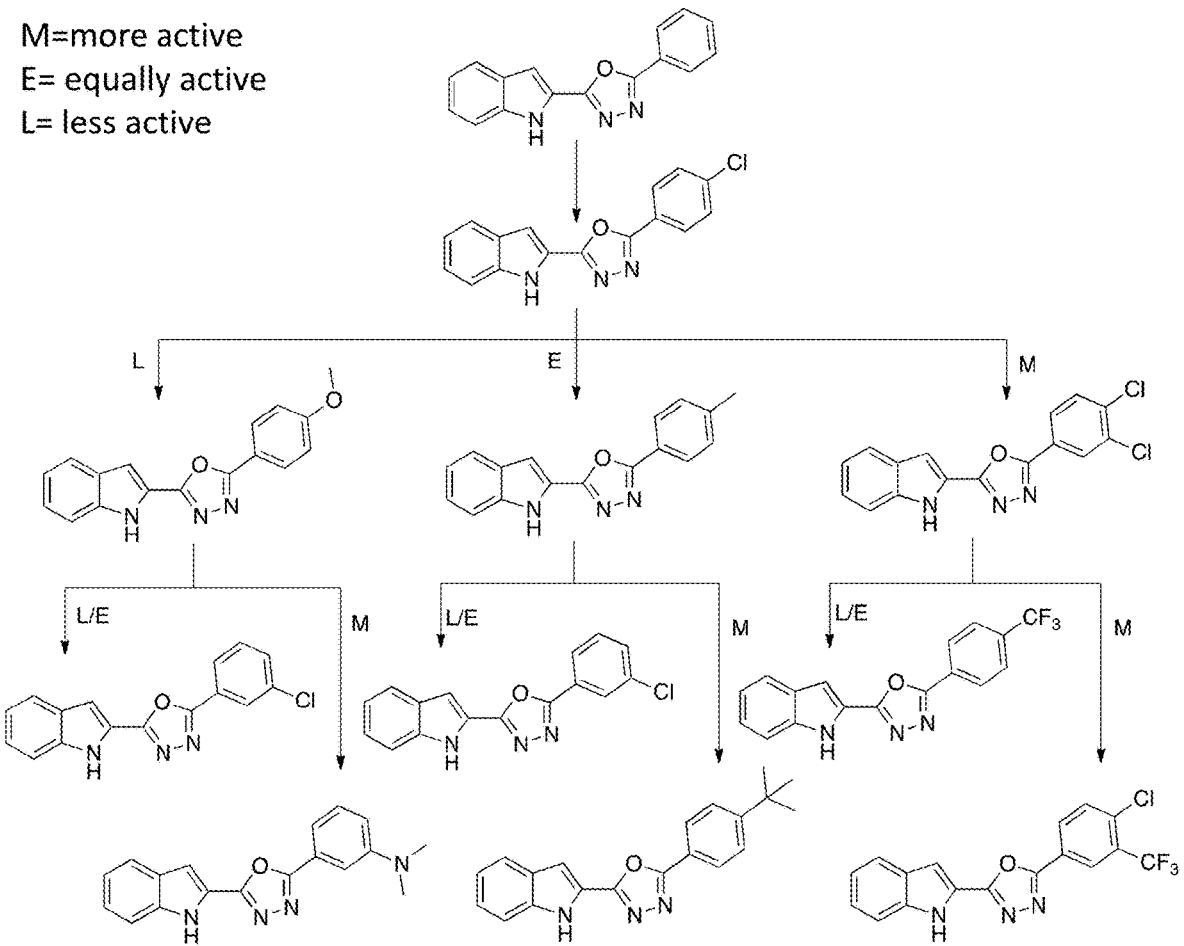
Figure 15A:
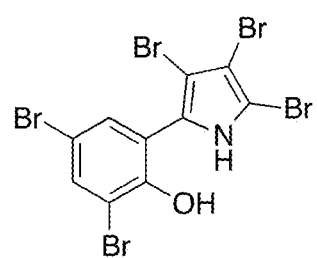
FIG. 15A-15C. Pentabromopseudilin—FIG. 15A, Pentabromopseudilin structure and FIG. 15B, IspD bound configuration of pentabromopseudilin in X-ray crystal structure with *Arabidopsis thaliana* IspD. Due to acidic nature of the tribromo substituted pyrrole and dibromo substituted phenol, these compounds were able to coordinate to $Mg^{2+}$. Crystal structure reprinted with permissions from Wiley Online Library.
Figure 15B:
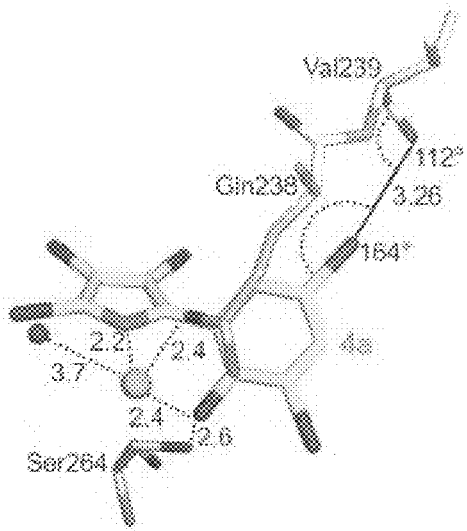
Figure 15C:
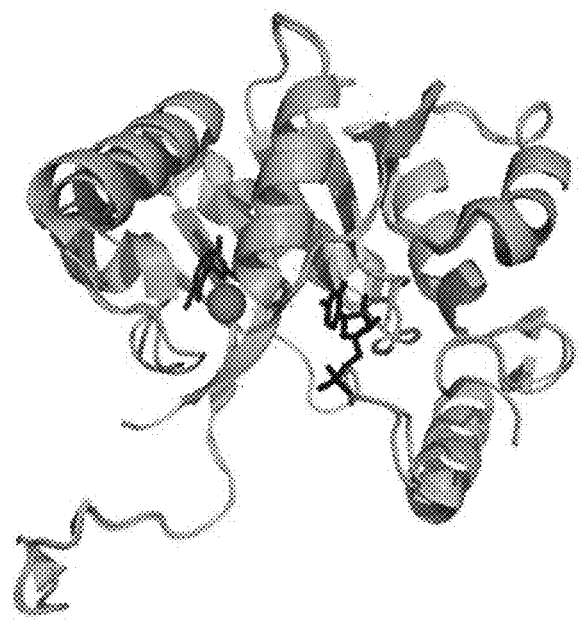
Figure 16:
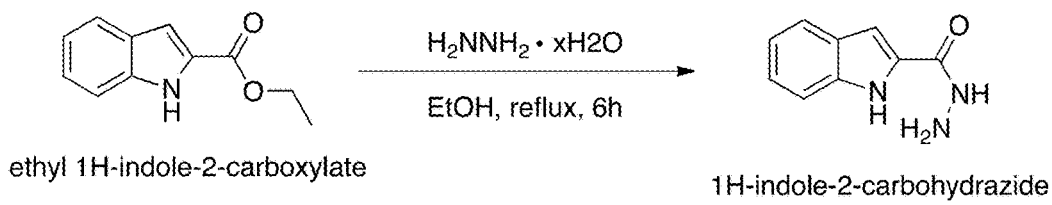
FIG. 16. Preparation of 1H-indole-2-carbohydrazide
Figure 17:
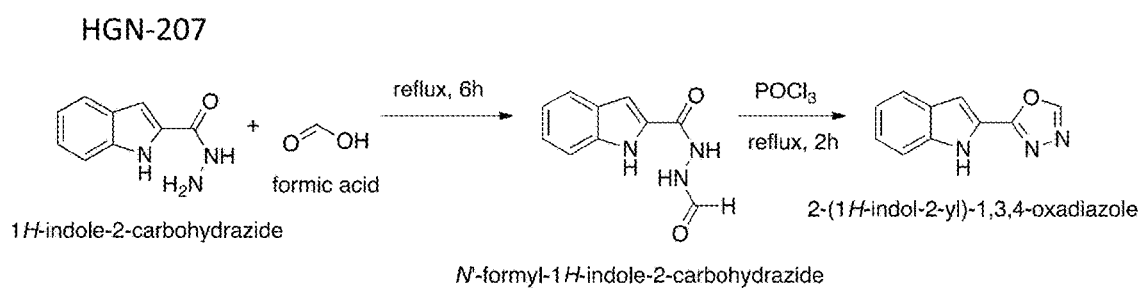
FIG. 17. Preparation of 2-(1H-indol-2-yl)-1,3,4-oxadiazole (HGN-207)
Figure 18:
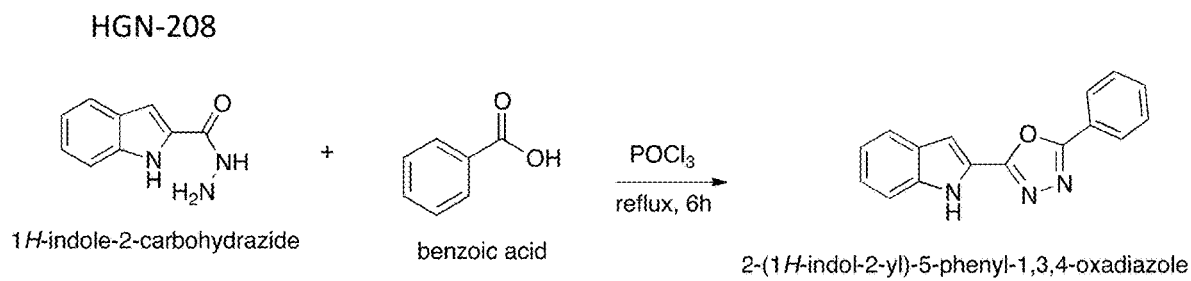
FIG. 18. Preparation of 2-(1H-indol-2-yl)-5-phenyl-1,3, 4-oxadiazole (HGN-208)
Figure 19:
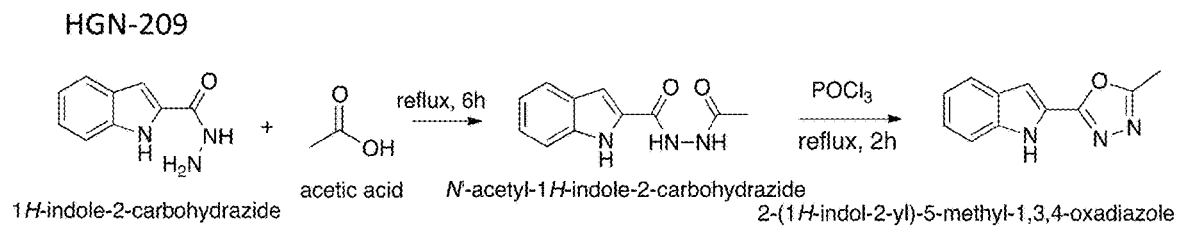
FIG. 19. Preparation of 2-(1H-indol-2-yl)-5-methyl-1,3,4-oxadiazole (HGN-209)
Figure 20:
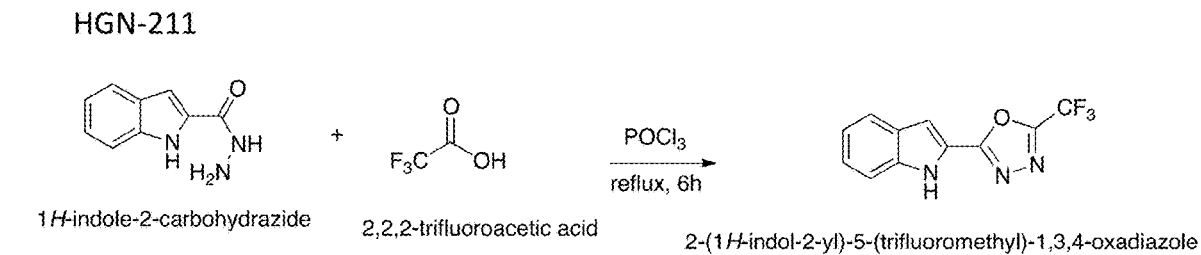
FIG. 20. Preparation of 2-(1H-indol-2-yl)-5-(trifluoromethyl)-1,3,4-oxadiazole (HGN-211)
Figure 21:
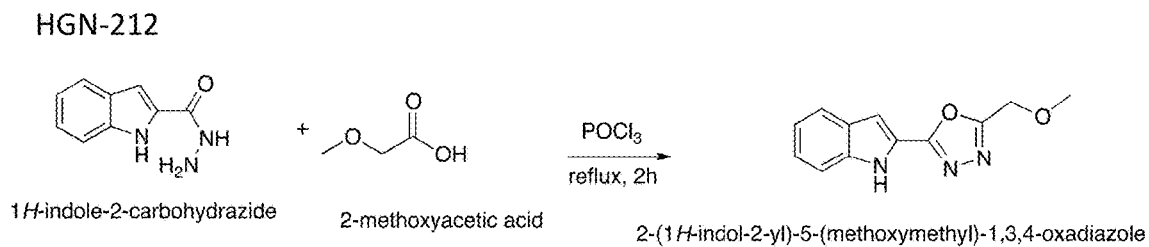
FIG. 21. Preparation of 2-(1H-indol-2-yl)-5-(methoxymethyl)-1,3,4-oxadiazole (HGN-212)
Figure 22:
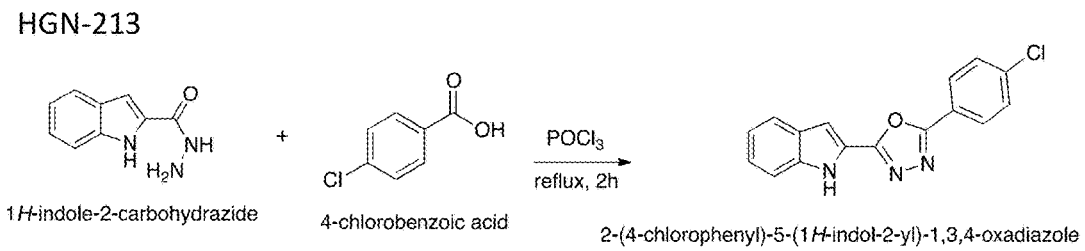
FIG. 22. Preparation of 2-(4-chlorophenyl)-5-(1H-indol-2-yl)-1,3,4-oxadiazole (HGN-213)
Figure 23:
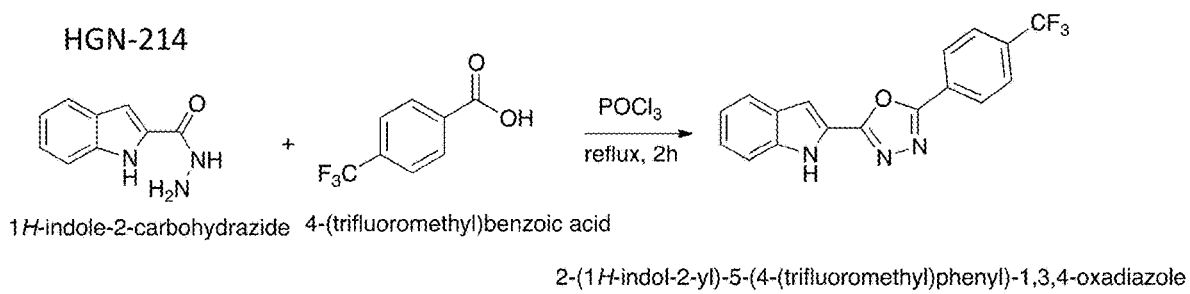
FIG. 23. Preparation of 2-(1H-indol-2-yl)-5-(4-(trifluoromethyl)phenyl)-1,3,4-oxadiazole (HGN-214)
Figure 24:
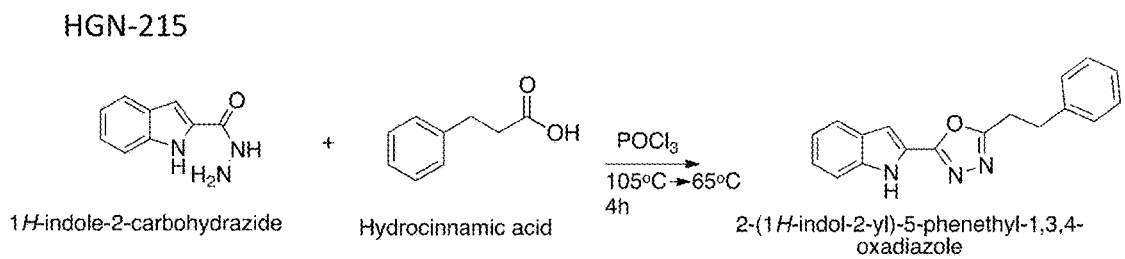
FIG. 24. Preparation of 2-(1H-indol-2-yl)-5-phenethyl-1,3,4-oxadiazole (HGN-215)
Figure 25:
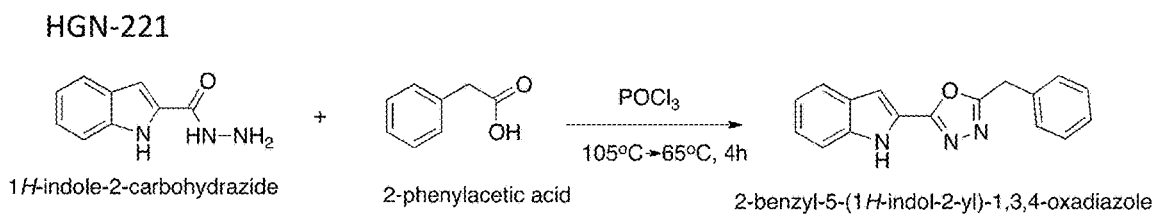
FIG. 25. Preparation of 2-benzyl-5-(1H-indol-2-yl)-1,3,4-oxadiazole (HGN-221)
Figure 26:
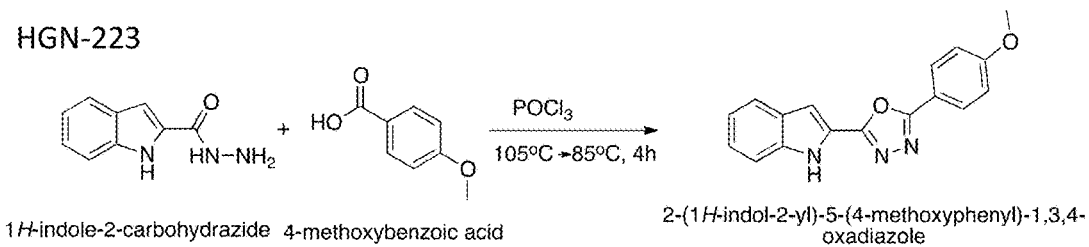
FIG. 26. Preparation of 2-(1H-indol-2-yl)-5-(4-methoxyphenyl)-1,3,4-oxadiazole (HGN-223)
Figure 27:
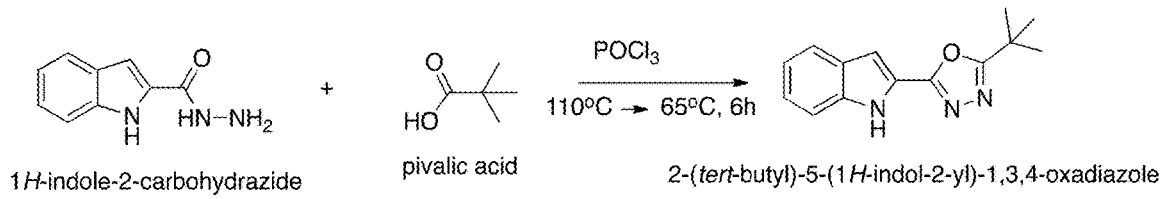
FIG. 27. Preparation of 2-(tert-butyl)-5-(1H-indol-2-yl)-1,3,4-oxadiazole (HGN-0239)
Figure 28:
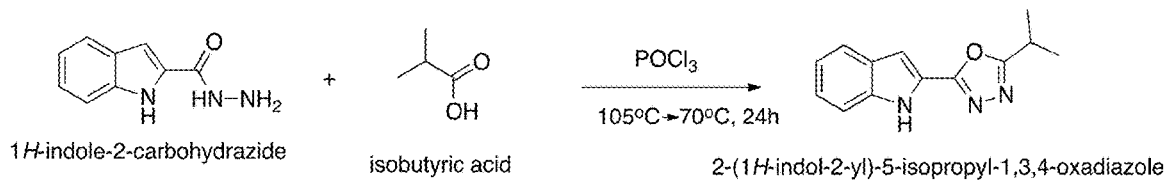
FIG. 28. Preparation of 2-(1H-indol-2-yl)-5-isopropyl-1,3,4-oxadiazole (HGN-240)
Figure 29:
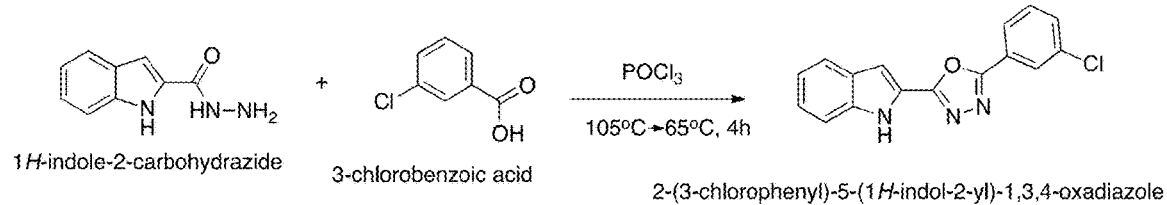
FIG. 29. Preparation of 2-(3-chlorophenyl)-5-(1H-indol-2-yl)-1,3,4-oxadiazole (HGN-241)
Figure 30:
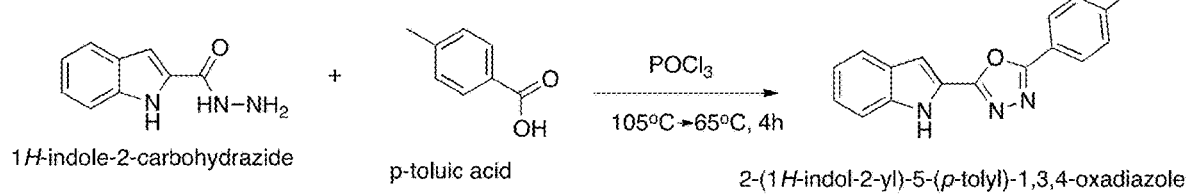
FIG. 30. Preparation of 2-(1H-indol-2-yl)-5-(p-tolyl)-1,3,4-oxadiazole (HGN-242)
Figure 31:
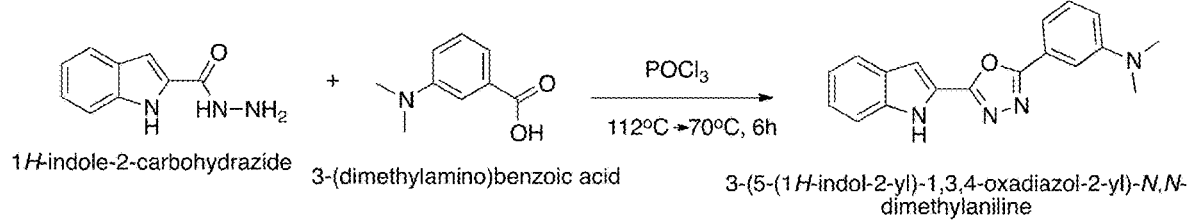
FIG. 31. Preparation of 3-(5-(1H-indol-2-yl)-1,3,4-oxadiazol-2-yl)-N,N-dimethylaniline (HGN-249)
Figure 32:
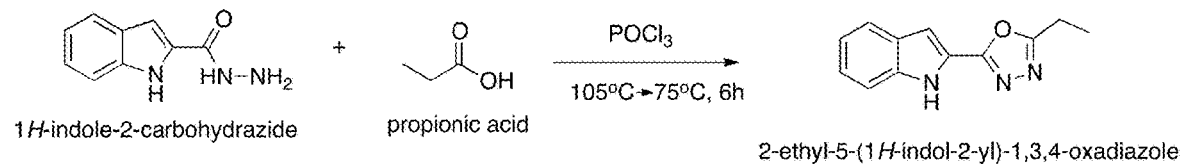
FIG. 32. Preparation of 2-ethyl-5-(1H-indol-2-yl)-1,3,4-oxadiazole (HGN-250)
Figure 33:
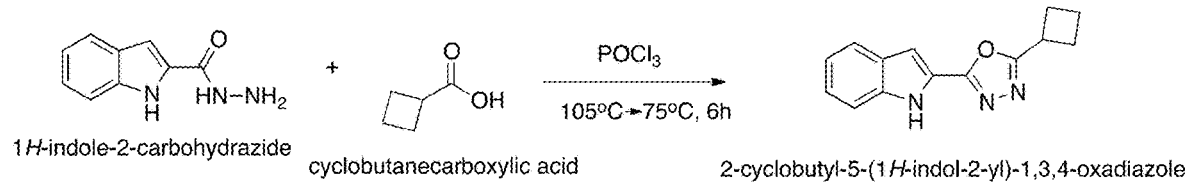
FIG. 33. Preparation of 2-cyclobutyl-5-(1H-indol-2-yl)-1,3,4-oxadiazole (HGN-251)
Figure 34:
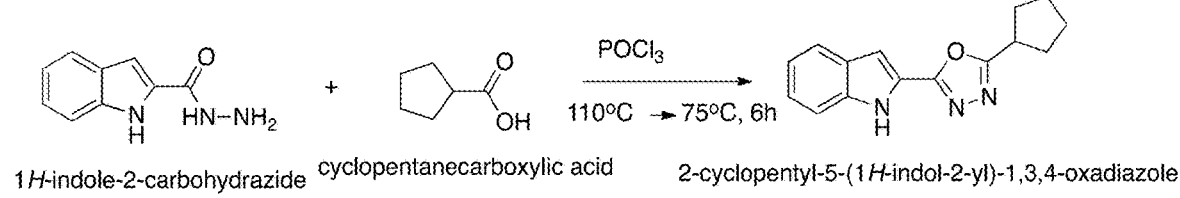
FIG. 34. Preparation of 2-cyclopentyl-5-(1H-indol-2-yl)-1,3,4-oxadiazole (HGN-252)
Figure 35:
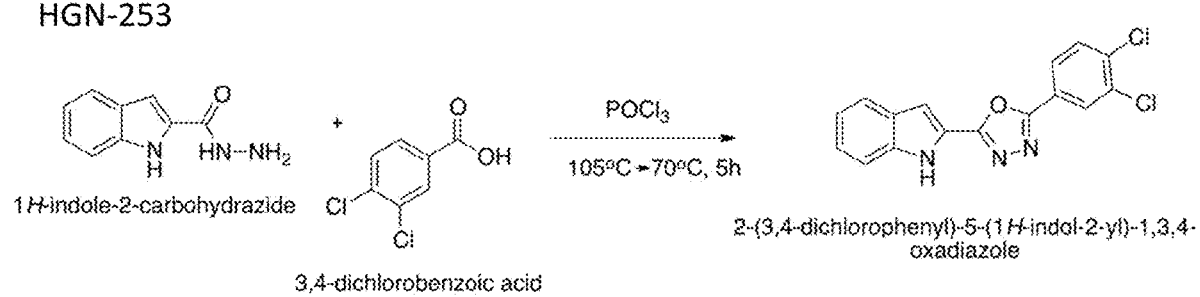
FIG. 35. Preparation of 2-(3,4-dichlorophenyl)-5-(1H-indol-2-yl)-1,3,4-oxadiazole (HGN-253)
Figure 36:
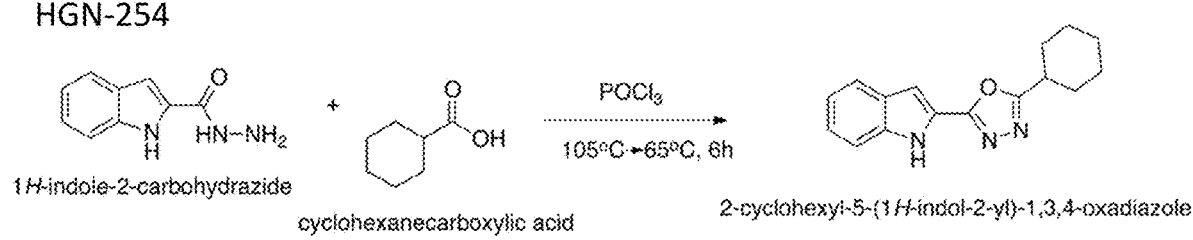
FIG. 36. Preparation of 2-cyclohexyl-5-(1H-indol-2-yl)-1,3,4-oxadiazole (HGN-254)
Figure 37:
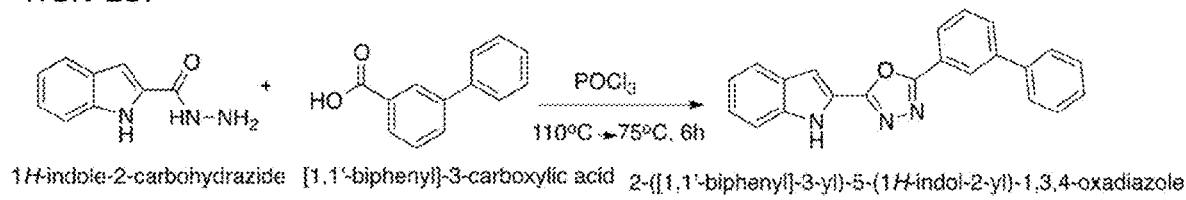
FIG. 37.
Figure 38:
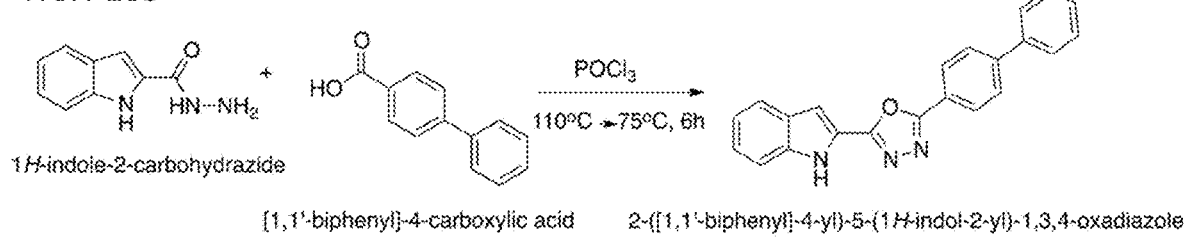
FIG. 38. Preparation of 2-([1,1'-biphenyl]-4-yl)-5-(1H-indol-2-yl)-1,3,4-oxadiazole (HGN-288)

Two areas of variability are the two heterocyles, the indole and the 1,3,4-oxadiazole. Typically, a fragment screening will identify fragments that have low binding affinity but high ligand efficiency. Therefore, the core fragment was kept constant throughout the analog series to maintain the high efficiency of the binding and the fragment was expanded to introduce new binding sites. Based on chemical synthesis of FOL7082, the most ideal area of variability was to substitute various functional groups on the 1,3,4-oxadiazole ring. Therefore, starting with the unsubstituted fragment, the following Topliss tree schemes were developed. (FIG. 14A-14B)

3. Pseudilin-Type IspD Inhibitor

In addition to the Topliss tree set of compounds, literature searches revealed similar compounds reported to have low micromolar $IC_{50}$ values. These compounds, evaluated using *Arabidopsis thaliana* IspD, were shown to bind to an allosteric binding site, possibly promoted by the high level of halogenation. While there were certain similarities to FOL7082, there are not enough to imply that they are binding in the same sites. The compound of interest is a pentabromopseudilin showing an $IC_{50}$ value of 13±2 µM without a metal added but 1.4±0.2 µM with 40 µM $Cd^{2+}$ added. The x-ray crystal structure with the pentabromopseudilin shows the halogen bonding and metal-ion interactions in AtIspD. The pentabromopseudilin compound synthetic route is 7 steps.

A simpler analog of the pentabromopseudlin compound may result in a similar activity with fewer steps. The analog chosen was the following:

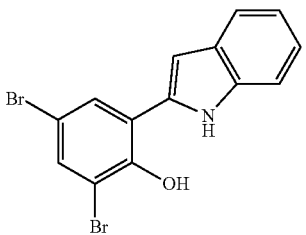 [SMILES: Oc1c(Br)cc(Br)cc1-c1cc2ccccc2[nH]1]

This compound could be synthesized in 3 steps by utilizing the Fischer-Indole synthesis. This compound is an analog of both the fragment hit FOL7082 and of the pentabromopseudilin. By changing the 1,3,4-oxadiazole ring of FOL7082 to a 2,4-dibromo phenol, this compound represents a single change analog of FOL7082 as shown below.

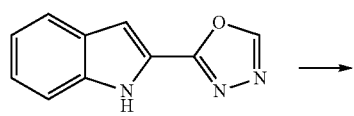

FOL7082

The x-ray crystal structure of pentabromopseudilin shows the pyrrole nitrogen coordinating with $Cd^{2+}$, and this is likely due to the fact that the bromines on the pyrrole ring increase the acidity of the N—H moiety. The hydroxyl group on the phenol is also much more acidic by placing bromines ortho and para to it. The coordination to the $Cd^{2+}$ is dependent on these acidities. In the FOL7082 analog, the brominated phenol allows for the hydroxyl acidity but without any indole substitutions, the coordination between the indole N—H and metal will likely be much weaker than the pseudilin compound and activity will likely be lower because of this if it binds the same way to the enzyme. However, the indole group allows for a larger amount of possible variability as it can be easily substituted, providing a starting point for a new set of analogs.

Preparation of Compounds

1. Indole Series (FIGS. 16-38)

To a round bottom flask add 0.005 moles of ethyl indole-2-carboxylate with 20 mL ethanol. Add 0.5 mL hydrazine hydrate (50-60%). Reflux solution for 6 hours. Allow solution to cool to room temperature and allow product to precipitate out by placing round bottom flask in an ice bath. Filter product and recrystallize in ethanol. Yield 77%.

2-(1H-indol-2-yl)-1,3,4-oxadiazole (HGN-207)

To a dry, 100 mL round bottom flask was added 1H-indole-2-carbohydrazide (211.6 mg, 1.208 mmol) and 15 mL formic acid. The resulting solution was stirred at reflux for 6 hours. Excess formic acid was removed under reduced pressure and the resulting solid was washed with cold ethanol, filtered, and dried solid. Yield of N'-formyl-1H-indole-2-carbohydrazide was 240.6 mg (98.0%). 214.8 mg (1.057 mmol) of resulting solid was dissolved and refluxed in 6 mL $POCl_3$ for 2 hours. The resulting reaction mixture was cooled to room temperature and poured over crushed ice. Saturated sodium bicarbonate solution was added slowly while stirring until solution was slightly basic (pH=8). Solid product was filtered and washed with cold ethanol and dried. Product was recrystallized with ethanol to produce 2-(1H-indol-2-yl)-1,3,4-oxadiazole (195.7 mg, 59% yield). $^1H$ NMR 300 MHz (DMSO-$d_6$) 12.28 (1H, s), 9.36 (1H,$), 7.68 (1H, d, J=8.0 Hz), 7.49 (1H, d, J=8.3 Hz), 7.27 (1H, t, J=7.2 Hz), 7.23 (1H, s), 7.11 (1H, t, J=7.0); $^{13}C$ NMR 300 MHz (DMSO-$d_6$): 159.45, 154.33, 138.21, 127.69, 124.71, 121.96, 121.38, 120.82, 112.75, 105.49; (cESI-MS) m/z $[M]^+$ calcd for $C_{10}H_8N_3O^+$ 186.07, found 186.2; m.p. 205-207° C.

2-(1H-indol-2-yl)-5-phenyl-1,3,4-oxadiazole (HGN-208)

To a dry, 100 mL round bottom flask was added benzoic acid (146.6 mg, 1.200 mmol) and 1H-indole-2-carbohydrazide (175.2 mg, 1.000 mmol) followed by 6 mL $POCl_3$ and the resulting mixture was refluxed for 6 h. The reaction mixture was cooled to room temperature and excess $POCl_3$ was removed under reduced pressure. Cold water was added to reaction vessel followed with saturated sodium bicarbonate solution until pH was slightly basic (pH=8). Product was filtered and dried and purified via column chromatography using a gradient of ethyl acetate in hexane starting with 1:5 ethyl acetate:hexane. Product was then recrystallized in ethanol to yield 2-(1H-indol-2-yl)-5-phenyl-1,3,4-oxadiazole (57.4 mg, 22% yield). $^1$H NMR 300 MHz (DMSO-d$_6$) 12.34 (1H, s), 8.14 (2H, dd, J=2.19, 5.52), 7.72-7.65 (4H, m), 7.52 (1H, d, J=8.3 Hz), 7.34 (1H, s), 7.28 (1H, t, J=7.6 Hz), 7.12 (1H, t, J=7.6 Hz); $^{13}$C NMR 300 MHz (DMSO-d$_6$):163.83, 159.87, 138.29, 132.51, 129.93, 127.79, 127.10, 124.75, 123.74, 121.96, 121.51, 120.85, 112.73, 105.62; (cESI-MS) m/z [M]$^+$ calcd for C$_{16}$H$_{12}$N$_3$O$^+$ 262.10, found 262.2; m.p 254-257° C.

2-(1H-indol-2-yl)-5-methyl-1,3,4-oxadiazole (HGN-209)

To a dry, 100 mL round bottom flask was added 1H-indole-2-carbohydrazide (175.2 mg, 1 mmol) and 15 mL of glacial acetic acid. Resulting mixture was refluxed for 6 h. Excess acetic acid was removed under reduced pressure to yield 247.6 mg crude product, which was then recrystallized in ethanol. Product was filtered, dried, and added to a clean, 100 mL round bottom flask. 6 mL POCl$_3$ was added and solution was refluxed for 2 hours under nitrogen. Excess POCl$_3$ was removed under reduced pressure and crushed ice was added to reaction vessel. The mixture was poured into a beaker and a saturated sodium bicarbonate solution was added slowly until pH was slightly basic (pH=8). Product was filtered, dried, and collected to yield 162.7 mg of product, which was then purified using column chromatography with a gradient starting at 5% methanol in dichloromethane to yield 2-(1H-indol-2-yl)-5-methyl-1,3,4-oxadiazole (89.0 mg, 45% yield). $^1$H NMR 300 MHz (DMSO-d$_6$) 12.21 (1H, s), 7.66 (1H, d, J=7.98 Hz), 7.47 (1H, d, J=8.16 Hz), 7.25 (1H, t, J=7.28 Hz), 7.14 (1H,$), 7.09 (1H, t, J=7.41 Hz), 2.60 (3H, s); $^{13}$C NMR 300 MHz (DMSO-d$_6$): 163.77, 159.78, 138.09, 127.71, 124.50, 121.85, 121.73, 120.72, 112.68, 104.80, 11.06; (cESI-MS) m/z [M]$^+$ calcd for C$_{11}$H$_{10}$N$_3$O$^+$ 200.08, found 200.2; m.p. 232-234° C.

2-(1H-indol-2-yl)-5-(trifluoromethyl)-1,3,4-oxadiazole (HGN-211)

To a 100 mL round bottom flask was added 1H-indole-2-carbohydrazide (175.2 mg, 1 mmol) and 6 mL POCl$_3$ followed by trifluoroacetic acid (171.0 mg, 1.5 mmol). The resulting mixture was refluxed for 6 h. The reaction mixture was poured over crushed ice and saturated sodium bicarbonate solution was added slowly until the mixture was slightly basic (pH=8). Product was filtered and dried followed by purification via column chromatography using 10% ethyl acetate in hexane as the eluting solvent to yield 2-(1H-indol-2-yl)-5-(trifluoromethyl)-1,3,4-oxadiazole (164.8 mg, 65.1% yield). $^1$H NMR 300 MHz (DMSO-d$_6$) 12.50 (1H, s), 7.71 (1H, d, J=7.92 Hz), 7.51 (1H, d, J=8.31 Hz), 7.40 (1H, s), 7.31 (1H, t, J=7.21 Hz), 7.14 (1H, t, J=6.93 Hz); $^{13}$C NMR 300 MHz (DMSO-d$_6$): 161.70, 153.97, 138.66, 127.58, 125.49, 122.30, (C—F q 121.15, 118.55, 114.97, 111.51, J=241 Hz), 119.87, 112.95, 107.52; m.p. 182-184° C.

2-(1H-indol-2-yl)-5-(methoxymethyl)-1,3,4-oxadiazole (HGN-212)

To a 100 mL round bottom flask was added 1H-indole-2-carbohydrazide (175.2 mg, 1 mmol) and 6 mL POCl$_3$ followed by methoxyacetic acid (135.1 mg, 1.5 mmol). The mixture was refluxed for 2 h. The reaction mixture was poured over crushed ice and saturated sodium bicarbonate solution was added slowly until mixture was slightly basic (pH=8). Solid product was filtered and dried followed by purification via column chromatography using a 1:2 mixture of ethyl acetate in hexane to yield 2-(1H-indol-2-yl)-5-(methoxymethyl)-1,3,4-oxadiazole (94.1 mg, 41%). $^1$H NMR 300 MHz (DMSO-d$_6$) 12.30 (1H, s), 7.68 (1H, d, J=8.01 Hz), 7.48 (1H, d, J=8.28 Hz), 7.27 (1H, t, J=7.63 Hz), 7.22 (1H,$), 7.11 (1H, t, J=7.00 Hz), 4.75 (2H, s), 3.41 (3H, s); $^{13}$C NMR 300 MHz (DMSO-d$_6$): 163.24, 160.43, 136.25, 127.69, 124.75, 121.97, 121.29, 120.84, 112.76, 105.54, 63.59, 58.79; (cESI-MS) m/z [M]$^+$ calcd for C$_{12}$H$_{12}$N$_3$O$_2$$^+$ 230.09, found 230.2; m.p. 152-156° C.

2-(4-chlorophenyl)-5-(1H-indol-2-yl)-1,3,4-oxadiazole (HGN-213)

To a 100 mL round bottom flask was added 1H-indole-2-carbohydrazide (175.2 mg, 1.0 mmol) and 6 mL POCl$_3$ followed by 4-chlorobenzoic acid (234.6 mg, 1.5 mmol). The resulting mixture was heated to reflux until fully dissolved and then the temperature was reduced to 60° C. for 2 h. The resulting reaction mixture was the poured over crushed ice and saturated sodium bicarbonate solution was added until the mixture was slightly basic (pH=8). Solid product was filtered and dried followed by purification via column chromatography using a gradient of 12% ethyl acetate in hexane to 60% ethyl acetate in hexane. Product crystallized in the test tubes and was collected and dried to yield 2-(4-chlorophenyl)-5-(1H-indol-2-yl)-1,3,4-oxadiazole (110.9 mg, 38% yield). $^1$H NMR 300 MHz (DMSO-d$_6$) 12.35 (1H, s), 8.20-8.08 (2H, m), 7.80-7.65 (3H, m), 7.51 (1H, d, J=8.28 Hz), 7.34 (1H,$), 7.28 (1H, t, J=7.60 Hz), 7.12 (1H, t, J=7.13 Hz); $^{13}$C NMR 300 MHz (DMSO-d$_6$): 163.09, 159.99, 138.30, 137.22, 130.12, 128.88, 127.77, 124.82, 122.64, 121.99, 121.38, 120.88, 112.73, 105.77; (cESI-MS) m/z [M]$^+$ calcd for C$_{16}$H$_{11}$ClN$_3$O$^+$ 296.06, found 296.1; m.p. 265-270° C.

2-(1H-indol-2-yl)-5-(4-(trifluoromethyl)phenyl)-1,3,4-oxadiazole (HGN-214)

To a 100 mL round bottom flask was added 1H-indole-2-carbohydrazide (175.2 mg, 1.0 mmol) and 6 mL POCl$_3$ followed by 4-(trifluoromethyl)benzoic acid (228.1 mg, 1.2 mmol). The resulting mixture was heated to reflux until fully dissolved and then the temperature was reduced to 60° C. for 2 h. The resulting reaction mixture was poured over crushed ice and saturated sodium bicarbonate solution was added slowly until the mixture was slightly basic (pH=8). Solid product was filtered, dried, and recrystallization in ethanol with decolorizing carbon. Product was collected filtered and dried to yield 2-(1H-indol-2-yl)-5-(4-(trifluoromethyl)phenyl)-1,3,4-oxadiazole (103.4 mg, 31% yield). $^1$H NMR 300 MHz (DMSO-d$_6$) 12.39 (1H, s), 8.34 (2H, d, J=7.8 Hz), 8.04 (2H, d, J=8.4 Hz), 7.72 (1H, d, J=7.8 Hz), 7.52 (1H, d, J=8.4 Hz), 7.38 (1H, s), 7.29 (1H, t, J=8.0 Hz), 7.10 (1H, t, J=8.0 Hz); $^{13}$C NMR 300 MHz (DMSO-d$_6$): 162.82, 160.36, 138.36, 132.19, 131.17, (C—F q 128.18, 126.94, 124.92, 122.44, J=143.5 Hz) 127.91, 127.77, 127.54, 126.89, 122.04, 121.26, 120.92, 112.77, 106.03; (cESI-MS) m/z [M]$^+$ calcd for C$_{17}$H$_{11}$F$_3$N$_3$O$^+$ 330.09, found 330.3; m.p. 258-260° C.

2-(1H-indol-2-yl)-5-phenethyl-1,3,4-oxadiazole (HGN-215)

To a 100 mL round bottom flask was added 1H-indole-2-carbohydrazide (175.2 mg, 1.0 mmol), hydrocinnamic acid (180.2 mg, 1.2 mmol) and 6 mL $POCl_3$. The mixture was heated to reflux until solid was fully dissolved, followed by a reduction in heat to 65° C. for 4 h under nitrogen. The resulting mixture was poured over crushed ice and saturated sodium bicarbonate solution was added slowly until solution was slightly basic (pH=8). Solid was filtered, collected, and dried to produce 567.8 mg of crude product. Product was purified via column chromatography using a gradient of ethyl acetate in hexane starting at 8% ethyl acetate and moving to 66% ethyl acetate. Further purification was done via recrystallization in ethanol to yield 2-(1H-indol-2-yl)-5-phenethyl-1,3,4-oxadiazole (169.3 mg, 44% yield). $^1$H NMR 300 MHz (DMSO-$d_6$) 12.22 (1H, s), 7.67 (1H, d, J=7.89 Hz), 7.48 (1H, t, J=8.04 Hz), 7.31-7.18 (6H, m), 7.14 (1H,$), 7.10 (1H, t, J=7.49 Hz), 3.28 (2H, t, J=7.68 Hz), 3.13 (2H, t, J=7.49 Hz); $^{13}$C NMR 300 MHz (DMSO-$d_6$): 166.02, 159.71, 140.29, 138.12, 128.89, 128.82, 127.71, 126.83, 124.56, 121.87, 121.65, 120.76, 112.69, 104.97, 32.04, 26.85; (cESI-MS) m/z [M]$^+$ calcd for $C_{18}H_{16}N_3O^+$ 290.13, found 290.3; m.p. 161-164° C.

2-benzyl-5-(1H-indol-2-yl)-1,3,4-oxadiazole (HGN-221)

To a 100 mL round bottom flask was added 1H-indole-2-carbohydrazide (175.2 mg, 1.0 mmol), phenylacetic acid (163.4 mg, 1.2 mmol) and 6 mL $POCl_3$. The mixture was heated to reflux until all solid was dissolved followed by a reduction in heat to 65° C. for 4 h under nitrogen. The resulting mixture was cooled to room temperature and poured over crushed ice and saturated sodium bicarbonate solution was added until solution was slightly basic (pH=8). Solid was filtered, collected, and dried. Crude product was purified via recrystallization in ethanol to yield 2-benzyl-5-(1H-indol-2-yl)-1,3,4-oxadiazole (157.3 mg, 57%). $^1$H NMR 300 MHz (DMSO-$d_6$) 12.22 (1H, s), 7.65 (1H, d, J=7.95 Hz), 7.47 (1H, d, J=8.19 Hz), 7.43-7.28 (5H, m), 7.25 (1H, t, J=7.58 Hz), 7.14 (1H, s), 7.09 (1H, t, J=7.44 Hz), 4.38 (2H, s); $^{13}$C NMR 300 MHz (DMSO-$d_6$): 165.44, 160.08, 138.16, 134.90, 129.40, 129.25, 127.73, 127.68, 124.60, 121.89, 121.49, 120.76, 112.70, 105.16, 31.21; (cESI-MS) m/z [M]$^+$ calcd for $C_{17}H_{14}N_3O^+$ 276.11, found 276.3; m.p. 211-215° C.

To a 100 mL round bottom flask was added 1H-indole-2-carbohydrazide (350.4 mg, 2.0 mmol), 4-methoxybenzoic acid (365.2 mg, 2.4 mmol) and 12 mL $POCl_3$. The mixture was heated to reflux until all solid was dissolved followed by a reduction in heat to 85° C. for 4 h under nitrogen. The resulting mixture was cooled to room temperature and poured over crushed ice and saturated sodium bicarbonate solution was added until solution was slightly basic (pH=8). Solid was filtered, collected, and dried. Crude product was purified via recrystallization in ethanol to yield 2-(1H-indol-2-yl)-5-(4-methoxyphenyl)-1,3,4-oxadiazole (111.2 mg, 19.1% yield). $^1$H NMR 300 MHz (DMSO-$d_6$) 12.32 (1H, s), 8.07 (2H, d, J=8.7 Hz), 7.70 (1H, d, J=9 Hz), 7.51 (1H, d, J=8.7 Hz), 7.35-7.09 (5H, m), 3.87 (3H, s); $^{13}$C NMR 300 MHz (DMSO-$d_6$): 163.78, 162.58, 159.38, 138.21, 128.97, 127.80, 124.63, 121.90, 121.65, 120.80, 116.03, 115.40, 112.70, 105.30, 56.03; m.p. 243-246° C. (mass spec data not available due to low solubility in hplc grade methanol and acetonitrile)

2-(tert-butyl)-5-(1H-indol-2-yl)-1,3,4-oxadiazole (HGN-0239)

To a 100 mL round bottom flask was added 1H-indole-2-carbohydrazide (175.2 mg, 1.0 mmol), pivalic acid (122.6 mg, 1.2 mmol) and 6 mL $POCl_3$. The mixture was heated to reflux until all solid was dissolved followed by a reduction in heat to 65° C. for 6 h under nitrogen. The resulting mixture was cooled to room temperature and poured over crushed ice and saturated sodium bicarbonate solution was added until solution was slightly basic (pH=8). Solid was filtered, collected, and dried. Crude product was purified via recrystallization in ethanol to yield 2-(tert-butyl)-5-(1H-indol-2-yl)-1,3,4-oxadiazole (77.9 mg, 32%). $^1$H NMR 300 MHz (DMSO-$d_6$) 12.20 (1H, s), 7.66 (1H, d, J=7.5 Hz), 7.48 (1H, d, J=8.1 Hz), 7.25 (1H, t, J=7.7 Hz), 7.18 (1H, s), 7.09 (1H, t, J=7.5 Hz), 1.44 (9H, s); $^{13}$C NMR 300 MHz (DMSO-$d_6$): 172.57, 159.71, 138.10, 127.71, 124.52, 121.85, 121.71, 120.73, 112.68, 105.02, 32.52, 28.30; (cESI-MS) m/z [M]$^+$ calcd for $C_{14}H_{16}N_3O^+$ 242.13, found 242.3; m.p. 163-168° C.

2-(1H-indol-2-yl)-5-isopropyl-1,3,4-oxadiazole (HGN-240)

To a 100 mL round bottom flask was added 1H-indole-2-carbohydrazide (175.2 mg, 1.0 mmol), isobutyric acid (105.7 mg, 1.2 mmol) and 6 mL $POCl_3$. The mixture was heated to reflux to dissolve reactants followed by a reduction in heat to 70° C. for 24 h under nitrogen. The resulting mixture was cooled and poured over crushed ice and saturated sodium bicarbonate solution was added slowly until solution was slightly basic (pH=8). Solid was filtered, collected, and dried to produce 233.1 mg of crude product. Product was extracted with ethyl acetate and water. The organic layer was collected and dried over anhydrous sodium sulfate. The solution was transferred to a 250 mL round bottom flask and solvent was removed under reduced pressure. Product was purified via recrystallization in acetone and product was filtered and dried to yield 2-(1H-indol-2-yl)-5-isopropyl-1,3,4-oxadiazole (122.1 mg, 54% yield). $^1$H NMR 300 MHz (DMSO-$d_6$) 12.21 (1H, s), 7.66 (1H, d, J=7.50), 7.47 (1H, d, J=7.74 Hz), 7.25 (1H, t, J=7.20 Hz), 7.17 (1H, s), 7.09 (1H, t, 7.19), 3.29 (1H, m), 1.38 (6H, d, J=6.42 Hz); $^{13}$C NMR 300 MHz (DMSO-$d_6$): 170.45, 159.66, 138.10, 127.71, 124.50, 121.84, 121.73, 120.72, 112.67, 104.94, 26.11, 20.19; (cESI-MS) m/z [M]$^+$ calcd for $C_{13}H_{-14}N_3O^+$ 228.11, found 228.2; m.p. 164-170° C.

2-(3-chlorophenyl)-5-(1H-indol-2-yl)-1,3,4-oxadiazole (HGN-241)

To a 100 mL round bottom flask was added 1H-indole-2-carbohydrazide (175.2 mg), 3-chlorobenzoic acid (187.9 mg, 1.2 mmol) and 6 mL $POCl_3$. The mixture was heated to reflux with stirring until all solid was fully dissolved followed by a reduction in heat to 65° C. for 4 h under nitrogen. The resulting mixture was cooled to room temperature and poured over crushed ice and saturated sodium bicarbonate solution was added slowly until solution was slightly basic (pH=8). Solid was filtered, collected, dried, and purified via recrystallization in acetone to yield 2-(3-chlorophenyl)-5-(1H-indol-2-yl)-1,3,4-oxadiazole (74.5 mg, 25% yield). $^1$H NMR 300 MHz (DMSO-$d_6$) 12.35 (1H, s), 8.16 (1H, s), 8.10

(1H, d, J=7.41 Hz), 7.78-7.64 (3H, m), 7.52 (1H, d, J=8.49 Hz), 7.38 (1H, s), 7.29 (1H, t, J=7.14), 7.12 (1H, t, J=7.47 Hz); $^{13}$C NMR 300 MHz (DMSO-d$_6$): 162.67, 160.12, 138.30, 134.58, 132.27, 131.97, 127.78, 126.64, 125.74, 125.70, 124.86, 122.01, 121.32, 120.90, 112.73, 105.94; (cESI-MS) m/z [M]$^+$ calcd for C$_{16}$H$_{11}$ClN$_3$O$^+$ 296.06, found 296.2; m.p. 202-207° C.

2-(1H-indol-2-yl)-5-(p-tolyl)-1,3,4-oxadiazole (HGN-242)

To a 100 mL round bottom flask was added 1H-indole-2-carbohydrazide (175.2 mg, 1.0 mmol), p-toluic acid (163.4 mg, 1.2 mmol) and 6 mL POCl$_3$. The resulting mixture was heated to reflux with stirring until all solid was fully dissolved followed by a reduction in heat to 65° C. for 4 h under nitrogen. The mixture was cooled to room temperature and poured over crushed ice and saturated sodium bicarbonate solution was added slowly until solution was slightly basic (pH=8). Solid was filtered, collected, dried, and purified via recrystallization in acetone to yield 2-(1H-indol-2-yl)-5-(p-tolyl)-1,3,4-oxadiazole (101.2 mg, 37% yield). $^1$H NMR 300 MHz (DMSO-d$_6$) 12.41 (1H, s), 8.03 (2H, d, J=7.98), 7.69 (1H, d, J=8.46), 7.52 (1H, d, J=8.49 Hz), 7.46 (2H, d, J=7.98 Hz), 7.31 (1H, s), 7.27 (1H, t, J=7.76 Hz), 7.11 (1H, t, J=7.25 Hz), 2.42 (3H, s); $^{13}$C NMR 300 MHz (DMSO-d$_6$): 163.91, 159.62, 142.69, 138.25, 130.47, 127.77, 127.07, 124.65, 121.91, 121.54, 120.96, 120.81, 105.41, 21.64; (cESI-MS) m/z [M]$^+$ calcd for C$_{17}$K$_4$N$_3$O$^+$ 276.11, found 276.2; m.p. 228-234° C.

3-(5-(1H-indol-2-yl)-1,3,4-oxadiazol-2-yl)-N,N-dimethylaniline (HGN-249)

To a 100 mL round bottom flask was added 1H-indole-2-carbohydrazide (175.2 mg, 1.0 mmol), 3-(dimethylamino)benzoic acid (165.2 mg, 1.0 mmol) and 6 mL POCl$_3$. The resulting mixture was heated to reflux with stirring until all solid was fully dissolved followed by a reduction in heat to 70° C. for 6 h under nitrogen. The resulting mixture was cooled to room temperature and poured over crushed ice and saturated sodium bicarbonate solution was added slowly until solution was slightly basic (pH=8). Solid was filtered, collected, dried, and purified via recrystallization in ethanol to yield 3-(5-(1H-indol-2-yl)-1,3,4-oxadiazol-2-yl)-N,N-dimethylaniline (136.6 mg, 45%). Product did not completely dissolve in hot ethanol and the product was still impure. Solubility issues prevented proper purification and pure product was not isolated.

2-ethyl-5-(1H-indol-2-yl)-1,3,4-oxadiazole (HGN-250)

To a 100 mL round bottom flask was added 1H-indole-2-carbohydrazide (175.2 mg, 1.0 mmol), propionic acid (88.9 mg, 1.2 mmol) and 6 mL POCl$_3$. The resulting mixture was heated to reflux until all solid was fully dissolved followed by a reduction in heat to 75° C. for 6 h under nitrogen. The mixture was cooled to room temperature and poured over crushed ice and saturated sodium bicarbonate solution was added slowly until solution was slightly basic (pH=8). Solid product was filtered, collected, and dried followed by extraction with ethyl acetate and water. The organic layer was dried over anhydrous sodium sulfate. Organic layer was then transferred to a round bottom flask and solvent was removed under reduced pressure. Product was purified via recrystallization in ethanol to yield 2-ethyl-5-(1H-indol-2-yl)-1,3,4-oxadiazole (117.8 mg, 55% yield). $^1$H NMR 300 MHz (DMSO-d$_6$) 12.21 (1H, s), 7.66 (1H, d, J=7.44 Hz), 7.48 (1H, d, J=7.62 Hz), 7.25 (1H, t, J=6.99 Hz), 7.15 (1H, s), 7.10 (1H, t, J=7.40 Hz), 3.02-2.86 (2H, m), 1.35 (3H, t, J=7.02 Hz); $^{13}$C NMR 300 MHz (DMSO-d$_6$): 167.59, 159.69, 138.10, 127.72, 124.50, 121.85, 121.75, 120.72, 112.68, 104.86, 18.84, 10.89; m.p. 138-143° C.

(mass spec data not available due to low solubility in hplc grade methanol and acetonitrile)

2-cyclobutyl-5-(1H-indol-2-yl)-1,3,4-oxadiazole (HGN-251)

To a 100 mL round bottom flask was added 1H-indole-2-carbohydrazide (175.2 mg, 1.0 mmol), cyclobutanecarboxylic acid (120.1 mg, 1.2 mmol) and 6 mL POCl$_3$. The resulting mixture was heated to reflux until all solid was fully dissolved, followed by a reduction in heat to 75° C. for 6 h under nitrogen. The mixture was cooled and poured over crushed ice and saturated sodium bicarbonate solution was added slowly until solution was slightly basic. Solid was filtered, collected, and dried to produce 294.3 mg of crude product. Purification was done via recrystallization in acetone to yield 2-cyclobutyl-5-(1H-indol-2-yl)-1,3,4-oxadiazole (127.0 mg, 53% yield). $^1$H NMR 300 MHz (DMSO-d$_6$) 12.21 (1H, s), 7.66 (1H, d, J=7.95 Hz), 7.48 (1H, d, J=8.25 Hz), 7.24 (1H, t, J=7.62 Hz), 7.17 (1H, s), 7.09 (1H, t, J=7.49 Hz), 3.85 (1H, quin., J=8.45 Hz), 2.43 (4H, q, J=8.07 Hz), 2.18-1.95 (2H, m); $^{13}$C NMR 300 MHz (DMSO-d$_6$): 168.69, 159.71, 138.12, 127.73, 124.50, 121.84, 121.75, 120.72, 112.68, 104.96, 30.04, 26.79, 18.78; (cESI-MS) m/z [M]$^+$ calcd for C$_{14}$H$_{14}$N$_3$O$^+$ 240.11, found 240.2; m.p. 169-173° C.

2-cyclopentyl-5-(1H-indol-2-yl)-1,3,4-oxadiazole (HGN-252)

To a 100 mL round bottom flask was added 1H-indole-2-carbohydrazide (175.2 mg, 1.0 mmol), cyclopentanecarboxylic acid (137.0 mg, 1.2 mmol) and 6 mL POCl$_3$. The resulting mixture was heated to reflux until all solid was fully dissolved, followed by a reduction in heat to 75° C. for 6 hours under nitrogen. The mixture was cooled and poured over crushed ice and saturated sodium bicarbonate solution was added slowly until solution was slightly basic (pH=8). Solid was filtered, collected, and dried. Purification was done via recrystallization in ethanol to yield 2-cyclopentyl-5-(1H-indol-2-yl)-1,3,4-oxadiazole (164.8 mg, 54% yield). $^1$H NMR 300 MHz (DMSO-d$_6$); $^{13}$C NMR 300 MHz (DMSO-d$_6$): 169.16, 159.24, 137.62, 127.23, 123.97, 121.32, 121.29, 120.21, 112.17, 104.41, 35.13, 30.49, 25.01; (cESI-MS) m/z [M]$^+$ calcd for C$_{15}$H$_{16}$N$_3$O$^+$ 254.13, found 254.2; m.p. 150-154° C.

2-(3,4-dichlorophenyl)-5-(1H-indol-2-yl)-1,3,4-oxadiazole (HGN-253)

To a 100 mL round bottom flask was added 1H-indole-2-carbohydrazide (175.2 mg, 1.0 mmol), 3,4-dichlorobenzoyl chloride (209.5 mg, 1.0 mmol) and 6 mL POCl$_3$. The mixture was heated to reflux until all solid was fully dissolved, followed by a reduction in heat to 70° C. for 5 hours under nitrogen. Excess POCl$_3$ was removed under reduced pressure and the mixture was poured onto crushed ice and saturated sodium bicarbonate solution was added slowly until solution was slightly basic (pH=8). Solid product was filtered, collected, and extracted with ethyl acetate and water. Organic layer was dried over anhydrous sodium sulfate, collected, and solvent was removed under reduced pressure to produce 358.8 mg of crude product. Product was purified via recrystallization in acetone to yield 2-(3,4-dichlorophenyl)-5-(1H-indol-2-yl)-1,3,4-oxadiazole (96.2 mg, 28% yield). Product was still impure after recrystallization and further purification would yield too little product to continue.

2-cyclohexyl-5-(1H-indol-2-yl)-1,3,4-oxadiazole (HGN-254)

To a 100 mL round bottom flask was added 1H-indole-2-carbohydrazide (175.2 mg, 1.0 mmol), cyclohexanecarboxylic acid (153.8 mg, 1.2 mmol) and 6 mL $POCl_3$. The mixture was heated to reflux until all solid is dissolved, followed by a reduction in heat to 65° C. for 6 hours under nitrogen. The mixture was cooled and poured over crushed ice and saturated sodium bicarbonate solution was slowly added until solution was slightly basic (pH=8). Solid product was filtered, collected, and dried to produce 417.7 mg of crude product. Product was purified via recrystallization in acetone to yield 2-cyclohexyl-5-(1H-indol-2-yl)-1,3,4-oxadiazole (154.3 mg, 49% yield). $^1$H NMR 300 MHz (DMSO-$d_6$) 12.18 (1H, s), 7.66 (1H, d, J=7.92 Hz), 7.48 (1H, d, J=8.22 Hz), 7.25 (1H, t, J=7.62 Hz), 7.15 (1H, s), 7.09 (1H, t, J=7.49 Hz), 3.05 (1H, tt, J=3.69 Hz, 10.82 Hz), 2.15-2.03 (2H, m), 1.84-1.73 (2H, m), 1.73-1.52 (3H, m), 1.52-1.20 (3H, m); $^{13}$C NMR 300 MHz (DMSO-$d_6$): 168.88, 158.98, 137.62, 127.23, 123.99, 121.33, 121.27, 120.22, 112.18, 104.41, 34.11, 29.57, 25.16, 24.65; (cESI-MS) m/z $[M]^+$ calcd for $C_{16}H_{18}N_3O^+$ 268.14, found 268.2; m.p. 187-193° C.

To a 100 mL round bottom flask was added 1H-indole-2-carbohydrazide (175.2 mg, 1.0 mmol), [1,1'-biphenyl]-3-carboxylic acid (237.9 mg, 1.2 mmol) and 6 mL $POCl_3$. The mixture was heated to reflux until all solid is dissolved, followed by a reduction in heat to 75° C. for 6 hours under nitrogen. The mixture was cooled and poured over crushed ice and saturated sodium bicarbonate solution was slowly added until solution was slightly basic (pH=8). Solid product was filtered, collected, and dried to produce 307.7 mg of crude product. Product was purified via recrystallization in ethanol to yield 2-([1,1'-biphenyl]-3-yl)-5-(1H-indol-2-yl)-1,3,4-oxadiazole (95.4 mg, 28% yield). $^1$H NMR 300 MHz (DMSO-$d_6$) 12.33 (1H, s), 8.38 (1H, s), 8.15 (1H, d, J=9 Hz), 7.97 (1H, d, J=8.1 Hz), 7.85-7.68 (4H, m), 7.60-7.43 (4H, m), 7.40 (1H, s), 7.29 (1H, t, J=7.8 Hz), 7.13 (1H, t, J=7.4 Hz); $^{13}$C NMR 300 MHz (DMSO-$d_6$): 163.29, 159.47, 141.34, 138.92, 137.81, 130.26, 130.16, 129.11, 128.15, 127.33, 126.90, 125.57, 124.64, 124.28, 123.95, 121.47, 121.01, 120.37, 112.23, 105.32; m.p. 222-226° C.

(mass spec data not available due to low solubility in hplc grade methanol and acetonitrile)

To a 100 mL round bottom flask was added 1H-indole-2-carbohydrazide (175.2 mg, 1.0 mmol), [1,1'-biphenyl]-4-carboxylic acid (237.9 mg, 1.2 mmol) and 6 mL $POCl_3$. The mixture was heated to reflux until all solid is dissolved, followed by a reduction in heat to 75° C. for 6 hours under nitrogen. The mixture was cooled and poured over crushed ice and saturated sodium bicarbonate solution was slowly added until solution was slightly basic (pH=8). Solid product was filtered, collected, and dried to produce 320.8 mg of crude product. Product was purified via recrystallization in ethanol to yield 2-([1,1'-biphenyl]-4-yl)-5-(1H-indol-2-yl)-1,3,4-oxadiazole (102.4 mg, 30% yield). $^1$H NMR 300 MHz (DMSO-$d_6$) 12.34 (1H, s), 8.23 (1H, d, J=8.4 Hz), 7.98 (1H, d, J=8.4 Hz), 7.90-7.61 (4H, m), 7.60-7.42 (4H, m), 7.37 (1H, s), 7.29 (1H, t, J=7.8 Hz), 7.13 (1H, t, J=8.0 Hz); $^{13}$C NMR 300 MHz (DMSO-$d_6$): 143.88, 139.24, 138.30, 130.42, 129.62, 129.54, 128.87, 128.09, 127.73, 127.37, 127.28, 124.78, 122.61, 121.98, 121.53, 120.88, 112.74, 105.66; m.p. 258-260° C.

(mass spec data not available due to low solubility in hplc grade methanol and acetonitrile)

2. Benzothiazole Series. (FIGS. 39-46)

Figure 39:
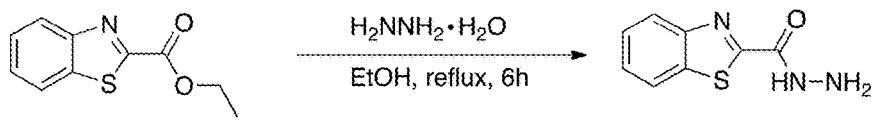
FIG. 39. Preparation of benzo[d]thiazole-2-carbohydrazide.
Figure 40:
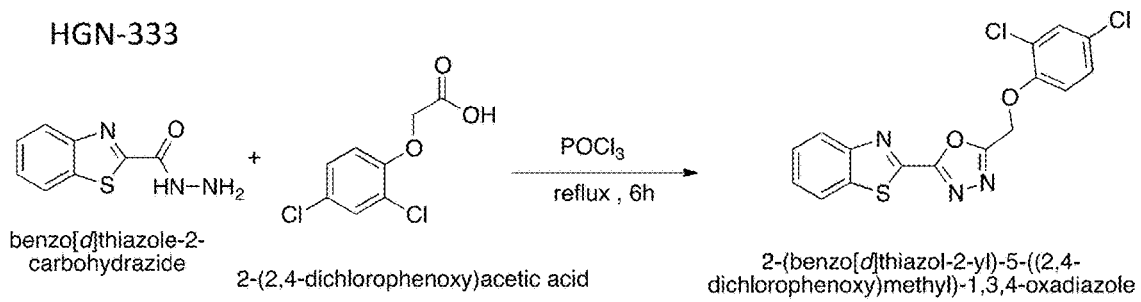
FIG. 40. Preparation of 2-(benzo[d]thiazol-2-yl)-5-((2,4-dichlorophenoxy)methyl)-1,3,4-oxadiazole (HGN-333)
Figure 41:
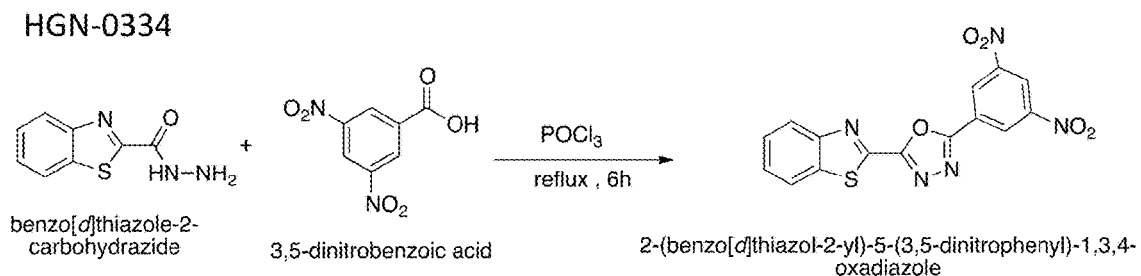
FIG. 41. Preparation of 2-(benzo[d]thiazol-2-yl)-5-(3,5-dinitrophenyl)-1,3,4-oxadiazole (HGN-334)
Figure 42:
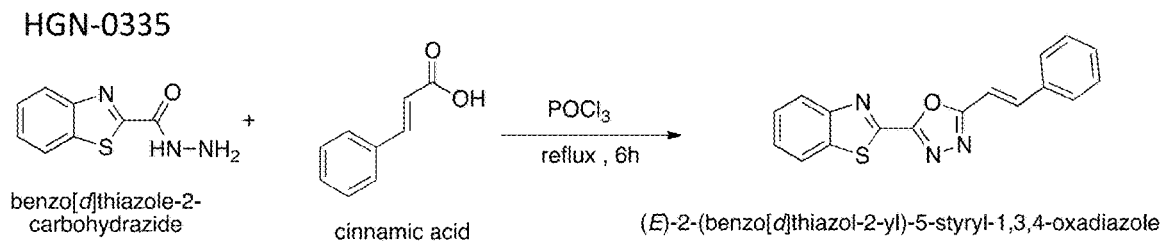
FIG. 42. Preparation of (E)-2-(benzo[d]thiazol-2-yl)-5-styryl-1,3,4-oxadiazole (HGN-335)
Figure 43:
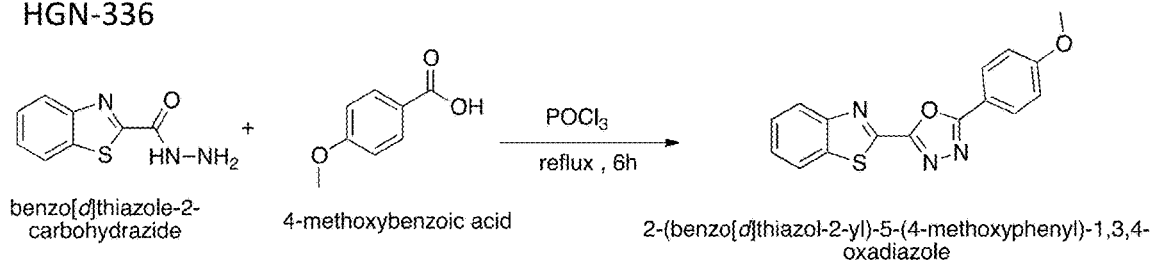
FIG. 43. Preparation of 2-(benzo[d]thiazol-2-yl)-5-(4-methoxyphenyl)-1,3,4-oxadiazole (HGN-336)
Figure 44:
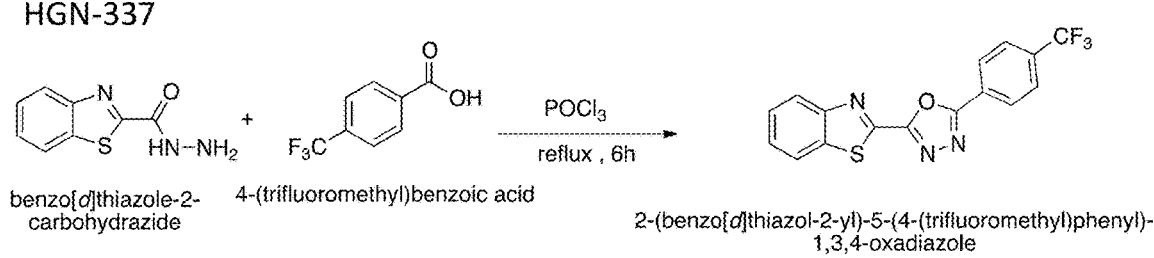
FIG. 44. Preparation of 2-(benzo[d]thiazol-2-yl)-5-(4-(trifluoromethyl)phenyl)-1,3,4-oxadiazole (HGN-337)
Figure 45:
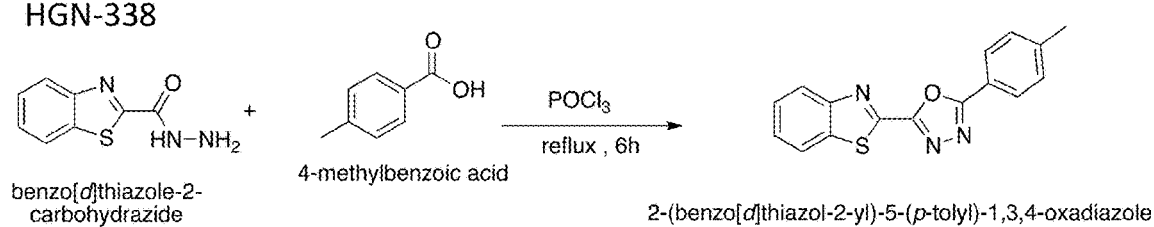
FIG. 45. Preparation of 2-(benzo[d]thiazol-2-yl)-5-(p-tolyl)-1,3,4-oxadiazole (HGN-338)
Figure 46:
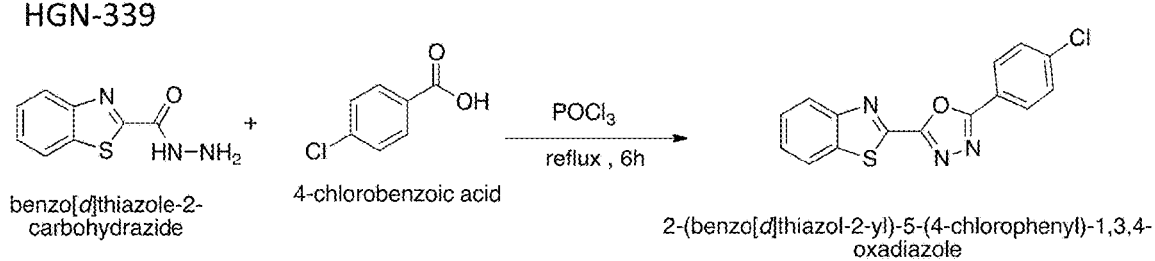
FIG. 46. Preparation of 2-(benzo[d]thiazol-2-yl)-5-(4-chlorophenyl)-1,3,4-oxadiazole (HGN-339)

Preparation of benzo[d]thiazole-2-carbohydrazide (FIG. 39)

To a 250 mL round bottom flask was added ethyl benzothiazole-2-carboxylate (1.0363 g, 5.0 mmol). 20 mL ethanol and 2 mL hydrazine hydrate were added followed by heating the solution to reflux for 6 hours. The reaction mixture was cooled to room temperature and solid precipitate was filtered, collected, and recrystallized in ethanol to yield benzo [d]thiazole-2-carbohydrazide (943.4 mg, 89.1% yield).

2-(benzo[d]thiazol-2-yl)-5-((2,4-dichlorophenoxy)methyl)-1,3,4-oxadiazole (HGN-333)

To a 250 mL round bottom flask was added benzo[d] thiazole-2-carbohydrazide (193.2 mg, 1.0 mmol), 2,4-dichlorophenoxyacetic acid (442.1 mg, 2.0 mmol), and 10 mL $POCl_3$. The resulting mixture was refluxed for 6 hours. The solution was cooled to room temperature and poured over crushed ice. The solution was left until precipitate formed, after which saturated sodium bicarbonate solution was added until solution was slightly basic. Product was extracted with ethyl acetate and the organic layer was collected and dried over anhydrous sodium sulfate. Organic layer was transferred to a clean 250 mL round bottom flask and solvent was removed under reduced pressure to yield 699.4 mg of crude product which was recrystallized in ethanol to produce 256.3 mg of product. Further purification was done via column chromatography using 25% ethyl acetate in hexane to yield 2-(benzo[d]thiazol-2-yl)-5-((2,4-dichlorophenoxy)methyl)-1,3,4-oxadiazole (171.9 mg, 46% yield). $^1$H NMR 300 MHz (CDCl$_3$) 8.31 (1H, dd, J=2.03, 6.33 Hz), 8.25 (1H, dd, J=2.03, 6.72 Hz), 7.73-7.61 (3H, m), 7.49-7.39 (2H, m), 5.72 (2H, s); $^{13}$C NMR 300 MHz (CDCl$_3$): 162.85, 161.40, 153.25, 152.00, 150.00, 135.57, 130.58, 128.25, 127.86, 127.68, 127.43, 124.98, 124.92, 122.02, 116.10, 61.28; (cESI-MS) m/z $[M]^+$ calcd for $C_{16}H_{10}Cl_2N_3O_2S^+$ 377.99, found 377.1; m.p. 163-165° C.

2-(benzo[d]thiazol-2-yl)-5-(3,5-dinitrophenyl)-1,3,4-oxadiazole (HGN-334)

To a 250 mL round bottom flask was added benzo[d] thiazole-2-carbohydrazide (193.2 mg, 1.0 mmol), 3,5-dinitrobenzoic acid (424.2 mg, 2.0 mmol), and 10 mL $POCl_3$. Resulting solution was refluxed for 6 hours. Reaction mixture was cooled to room temperature and poured over crushed ice. The solution was allowed to sit until product precipitated from solution, after which saturated sodium bicarbonate solution was slowly added until the solution was slightly basic (pH=8). Product was extracted using ethyl acetate. The organic layer was collected and dried over anhydrous sodium sulfate. Organic layer was then transferred to a clean 250 mL round bottom flask and solvent was removed under reduced pressure to yield 755.4 mg of crude product. Product was recrystallized in ethanol to yield 2-(benzo[d]thiazol-2-yl)-5-(3,5-dinitrophenyl)-1,3,4-oxadiazole (234.4 mg, 64%). $^1$H NMR 300 MHz (CDCl$_3$) 9.42 (2H, s), 9.27 (1H, s), 8.32 (1H, d, J=8.10 Hz), 8.08 (1H, d, J=7.62 Hz), 5.72 (2H, s), 7.72-7.61 (2H, m); $^{13}$C NMR 300 MHz (DMSO-d$_6$): 162.28, 161.42, 149.42, 149.29, 135.72, 128.00, 127.69, 127.01, 126.56, 124.99, 122.12, 121.57; (cESI-MS) m/z [M]$^+$ calcd for C$_{15}$H$_8$N$_5$O$_5$S$^+$ 370.02, found 371.0; m.p. 180-185° C.

(E)-2-(benzo[d]thiazol-2-yl)-5-styryl-1,3,4-oxadiazole (HGN-335)

To a 250 mL round bottom flask was added benzo[d]thiazole-2-carbohydrazide (193.2 mg, 1.0 mmol), trans cinnamic acid (177.8 mg, 1.2 mmol), and 10 mL POCl$_3$. Resulting solution was refluxed for 6 hours. Reaction mixture was allowed to cool to room temperature and poured over crushed ice. The solution was allowed to sit until product precipitated out, after which saturated sodium bicarbonate solution was slowly added until solution was slightly basic (pH=8). Product was extracted with ethyl acetate and the organic layer was collected and dried over anhydrous sodium sulfate. Organic layer was transferred to a clean 250 mL round bottom flask and solvent was removed under reduced pressure to produce (E)-2-(benzo[d]thiazol-2-yl)-5-styryl-1,3,4-oxadiazole (296.1 mg, 92% yield). $^1$H NMR 300 MHz (CDCl$_3$) 8.33-8.24 (1H, m), 8.28 (1H, dd, J=1.71, 9.42 Hz), 7.91-7.84 (2H, m), 7.80 (1H, s), 7.72-7.62 (2H, m), 7.53 (1H, s), 7.51-7.42 (3H, m); $^{13}$C NMR 300 MHz (CDCl$_3$): 165.59, 159.59, 153.35, 150.87, 141.24, 135.49, 134.50, 130.45, 129.11, 127.77, 127.40, 127.29, 124.69, 121.99, 108.97; (cESI-MS) m/z [M]$^+$ calcd for C$_{17}$H$_{12}$N$_3$OS$^+$ 306.07, found 306.3; m.p. 202-204° C.

2-(benzo[d]thiazol-2-yl)-5-(4-methoxyphenyl)-1,3,4-oxadiazole (HGN-336)

To a 250 mL round bottom flask was added benzo[d]thiazole-2-carbohydrazide (193.2 mg, 1.0 mmol), 4-methoxybenzoic acid (304.3 mg, 2.0 mmol), and 10 mL POCl$_3$. Resulting mixture was refluxed for 6 hours. Reaction mixture was allowed to cool to room temperature and poured over crushed ice and allowed to sit until product precipitated out and saturated sodium bicarbonate solution was added until solution was slightly basic (pH=8). Product was extracted with ethyl acetate and the organic layer was collected and dried over anhydrous sodium sulfate. Organic layer was transferred to a clean 250 mL round bottom flask and solvent was removed under reduced pressure to yield 318.4 mg of crude product. Product was recrystallized in ethanol to produce 2-(benzo[d]thiazol-2-yl)-5-(4-methoxyphenyl)-1,3,4-oxadiazole (105.6 mg, 34% yield). $^1$H NMR 300 MHz (CDCl$_3$) 8.27 (1H, d, J. 8.04 Hz), 8.21 (2H, d, J=8.64 Hz), 7.66-7.54 (3H, m), 7.07 (2H, d, J=8.64 Hz), 3.93 (3H, s); $^{13}$C NMR 300 MHz (CDCl$_3$): 165.92, 163.01, 159.80, 153.38, 151.05, 135.44, 129.45, 127.25, 127.19, 124.62, 121.95, 115.47, 114.65, 55.52; (cESI-MS) m/z [M]$^+$ calcd for C$_{16}$H$_{12}$N$_3$O$_2$S$^+$ 310.07, found 310.2; m.p. 167-169° C.

2-(benzo[d]thiazol-2-yl)-5-(4-(trifluoromethyl)phenyl)-1,3,4-oxadiazole (HGN-337)

To a 250 mL round bottom flask was added benzo[d]thiazole-2-carbohydrazide (386.5 mg, 2.0 mmol), 4-(trifluoromethyl)benzoic acid (380.2 mg, 2.0 mmol), and 10 mL POCl$_3$. Mixture was refluxed for 6 hours and allowed to cool to room temperature. Solution was poured over crushed ice and allowed to sit until product precipitated out. Saturated sodium bicarbonate solution was added slowly until solution is slightly basic (pH=8). Product was extracted with ethyl acetate and the organic layer was collected and dried over anhydrous sodium sulfate. Solution was transferred to a clean 250 mL round bottom flask and solvent was removed under reduced pressure to produce 238.9 mg of crude product. Product was recrystallized in ethanol to yield 2-(benzo[d]thiazol-2-yl)-5-(4-(trifluoromethyl)phenyl)-1,3,4-oxadiazole (197.1 mg, 28% yield). $^1$H NMR 300 MHz (CDCl$_3$) 8.41 (2H, d, J=8.10 Hz), 8.29 (1H, d, J=7.23 Hz), 8.05 (1H, d, J=7.83 Hz), 7.86 (2H, d, J=8.22 Hz), 7.65 (1H, td, J=1.48, 7.73 Hz), 7.59 (1H, td, J=1.41, 7.38 Hz); $^{13}$C NMR 300 MHz (CDCl$_3$): 164.67, 160.69, 153.34, 150.41, 135.56, 134.72, 134.26, 133.82, 133.43, 127.90, 127.61, (C—F q 127.42, 125.29, 124.80, 122.05, J=134.1 Hz), 126.29, 126.24; (cESI-MS) m/z [M]$^+$ calcd for C$_{16}$H$_9$F$_3$N$_3$OS$^+$ 348.04, found 348.2; m.p. 145-148° C.

2-(benzo[d]thiazol-2-yl)-5-(p-tolyl)-1,3,4-oxadiazole (HGN-338)

To a 250 mL round bottom flask was added benzo[d]thiazole-2-carbohydrazide (386.5 mg, 2.0 mmol), p-toluic acid (272.3 mg, 2.0 mmol), and 10 mL POCl$_3$. Resulting solution was refluxed for 6 hours, allowed to cool to room temperature, and pour over crushed ice. The reaction mixture was allowed to sit until product precipitated out after which saturated sodium bicarbonate solution was added until solution was slightly basic (pH=8). Product was extracted with ethyl acetate and the organic layer was collected and dried with anhydrous sodium sulfate. Solution was transferred to a clean 250 mL round bottom flask and solvent was removed followed by recrystallization in ethanol to yield 2-(benzo[d]thiazol-2-yl)-5-(p-tolyl)-1,3,4-oxadiazole (157.3 mg, 27% yield). $^1$H NMR 300 MHz (DMSO-d$_6$) 8.28 (1H, d, J=7.41 Hz), 8.16 (2H, d, J=6.6 Hz), 8.04 (1H, d, J=7.62 Hz), 7.63 (1H, td, J=1.47, 7.68 Hz), 7.57 (1H, td, J=1.34, 7.43 Hz), 2.48 (3H, s); $^{13}$C NMR 300 MHz (DMSO-d$_6$): 165.66, 160.14, 153.25, 151.25, 143.51, 135.30, 130.63, 128.17, 127.97, 127.49, 124.62, 123.42, 120.38, 21.68; (cESI-MS) m/z [M]$^+$ calcd for C$_{16}$H$_{12}$N$_3$OS$^+$ 294.07, found 294.1; m.p. 155-160° C.

2-(benzo[d]thiazol-2-yl)-5-(4-chlorophenyl)-1,3,4-oxadiazole (HGN-339)

To a 250 mL round bottom flask was added benzo[d]thiazole-2-carbohydrazide (386.5 mg, 2.0 mmol), 4-chlorobenzoic acid (313.1 mg, 2.0 mmol), and 10 mL POCl$_3$. Resulting solution was refluxed for 6 hours, allowed to cool to room temp and pour over crushed ice. The reaction mixture was allowed to sit until product precipitated out, after which saturated sodium bicarbonate solution was slowly added until solution was slightly basic (pH=8). Product was extracted with ethyl acetate and the organic layer was collected and dried over anhydrous sodium sulfate. Organic layer was collected in a clean 250 mL round bottom flask and solvent was removed under reduced pressure to yield 344.6 mg crude product. Product was recrystallized in ethanol to yield 2-(benzo[d]thiazol-2-yl)-5-(4-chlorophenyl)-1,3,4-oxadiazole (185.6 mg, 30% yield). $^1$H NMR 300 MHz (DMSO-d$_6$) 8.27 (1H, d, J=7.95 Hz), 8.21 (2H, d, J=8.61 Hz), 8.04 (1H, d, J=6.96 Hz), 7.67-7.55 (4H, m); $^{13}$C NMR 300 MHz (CDCl$_3$): 165.10, 160.32, 153.33, 150.61, 138.94, 135.50, 129.63, 128.82, 127.49, 127.34, 124.73, 122.02, 121.50; (cESI-MS) m/z [M]$^+$ calcd for C$_{15}$H$_9$ClN$_3$OS$^+$ 314.02, found 314.1; m.p. 161-163° C.

Figure 47:
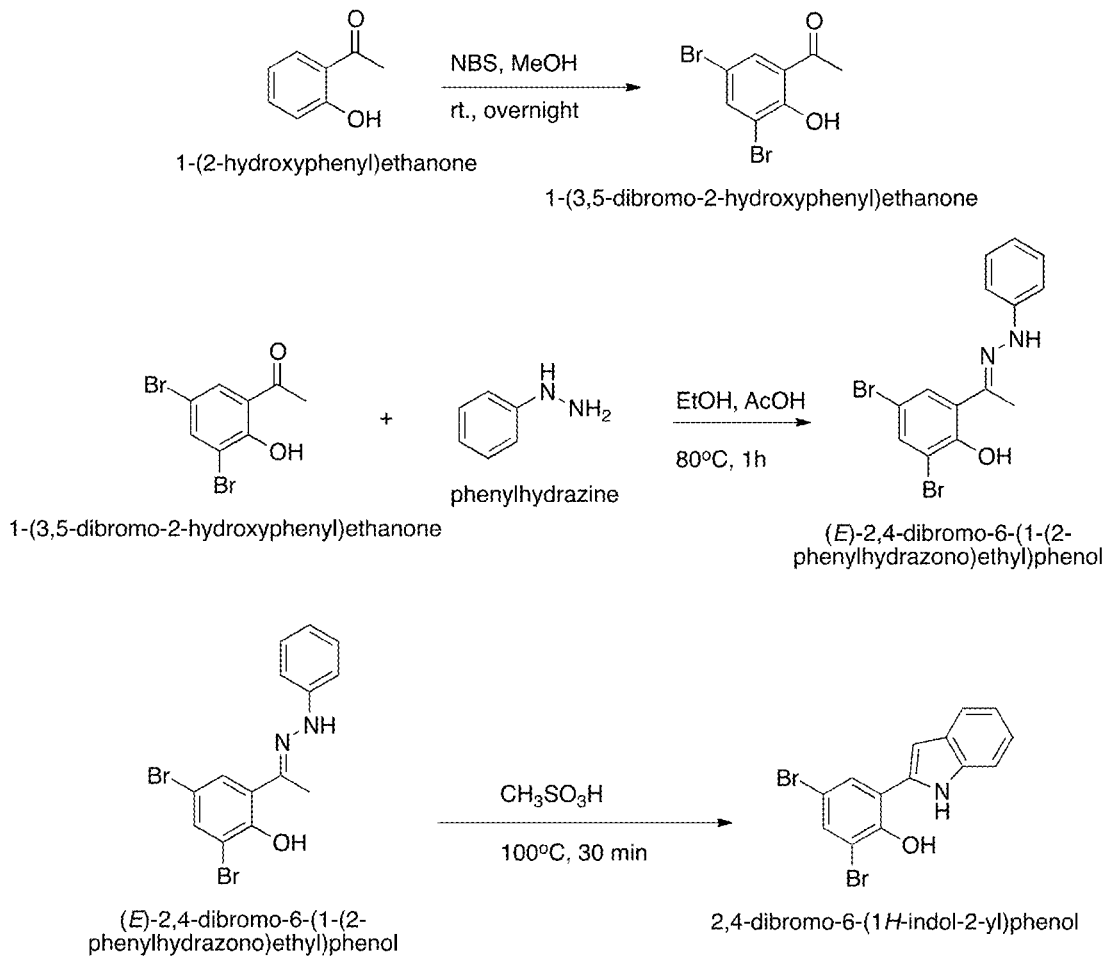
FIG. 47. Preparation of 2,4-dibromo-6-(1H-indol-2-yl)phenol (HGN-340)

3. Pseudilin-Like Series (FIG. 47)

2,4-dibromo-6-(1H-indol-2-yl)phenol (HGN-340)

To a 250 mL round bottom flask was added by 2'-hydroxyacetophenone (5.0 g, 36.7 mmol) and 60 mL of methanol. This solution was cooled to 0° C. in an ice bath. N-bromosuccinimide (19.6 g, 110.2 mmol) was added slowly with stirring to the solution on ice. The solution was brought up to room temperature, sealed, and allowed to stir overnight. The solution was poured into 100 mL water and allowed to sit producing a light yellow precipitate. The product was filtered, collected, and recrystallized in ethanol to yield 1-(3,5-dibromo-2-hydroxyphenyl)ethanone (2.2940 g, 21% yield). 1-(3,5-dibromo-2-hydroxyphenyl)ethanone (456.8 mg, 1.55 mmol) was added to a 100 mL round bottom flask with 10 mL ethanol and stirred. Phenylhydrazine (0.15 mL, 1.5 mmol) was added with 5 drops of glacial acetic acid and mixture was refluxed at 80° C. for 1 hour. The solution was cooled to room temperature and the solvent is evaporated off under reduced pressure to yield 598.1 mg crude product ((E)-2,4-dibromo-6-(1-(2-phenylhydrazono)ethyl)phenol). 10 mL of methanesulfonic acid was added to (E)-2,4-dibromo-6-(1-(2-phenylhydrazono)ethyl)phenol, which was not purified from the previous step. The mixture was heated at 100° C. for 30 minutes and then poured over crushed ice and neutralized with 1 M NaOH solution. The product was extracted with ethyl acetate, dried over anhydrous sodium sulfate, and concentrated. Purification was done using a gradient of ethyl acetate in hexane to yield 2,4-dibromo-6-(1H-indol-2-yl)phenol (342.1 mg, 60% yield, 12.7% yield overall). $^1$H NMR 300 MHz (DMSO-d$_6$) 11.38 (1H, s), 9.81 (1H, s), 7.91 (1H, s), 7.70 (1H, s), 7.56 (1H, d, J=7.56 Hz), 7.44 (1H, d, J=8.07 Hz), 7.12 (1H, td, J=1.09, 7.59 Hz), 7.08 (1H, s), 7.01 (1H, td, J=0.95, 7.43 Hz); $^{13}$C NMR 300 MHz (DMSO-d$_6$): 150.05, 136.53, 132.68, 132.48, 129.24, 128.05, 124.78, 121.98, 120.27, 119.28, 114.24, 111.97, 111.37, 103.44; (cESI-MS) m/z [M]$^+$ calcd for C$_{14}$H$_{10}$Br$_2$NO$^+$ 367.91, found 368.1; m.p. 104-110° C.

Figure 48:
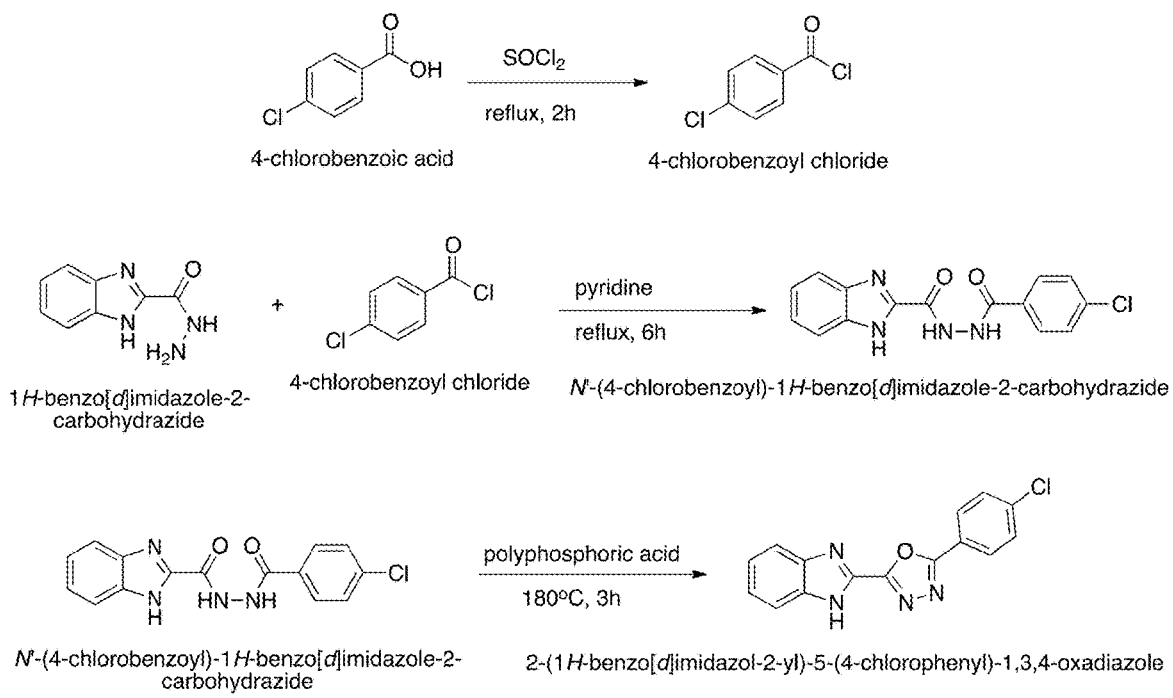
FIG. 48. Preparation of 2-(1H-benzo[d]15midazole-2-yl)-5-(4-chlorophenyl)-1,3,4-oxadiazole (HGN-421)
Figure 49:
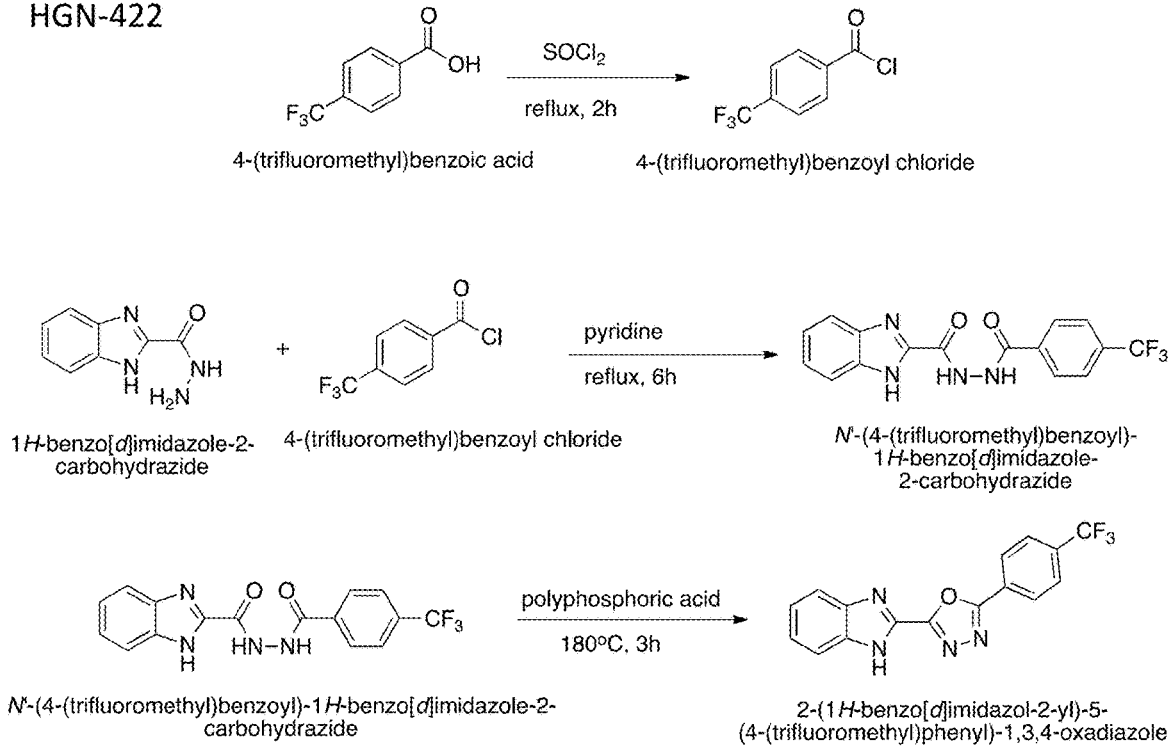
FIG. 49. Preparation of 2-(1H-benzo[d]imidazol-2-yl)-5-(4-(trifluoromethyl)phenyl)-1,3,4-oxadiazole (HGN-422)
Figure 50A:
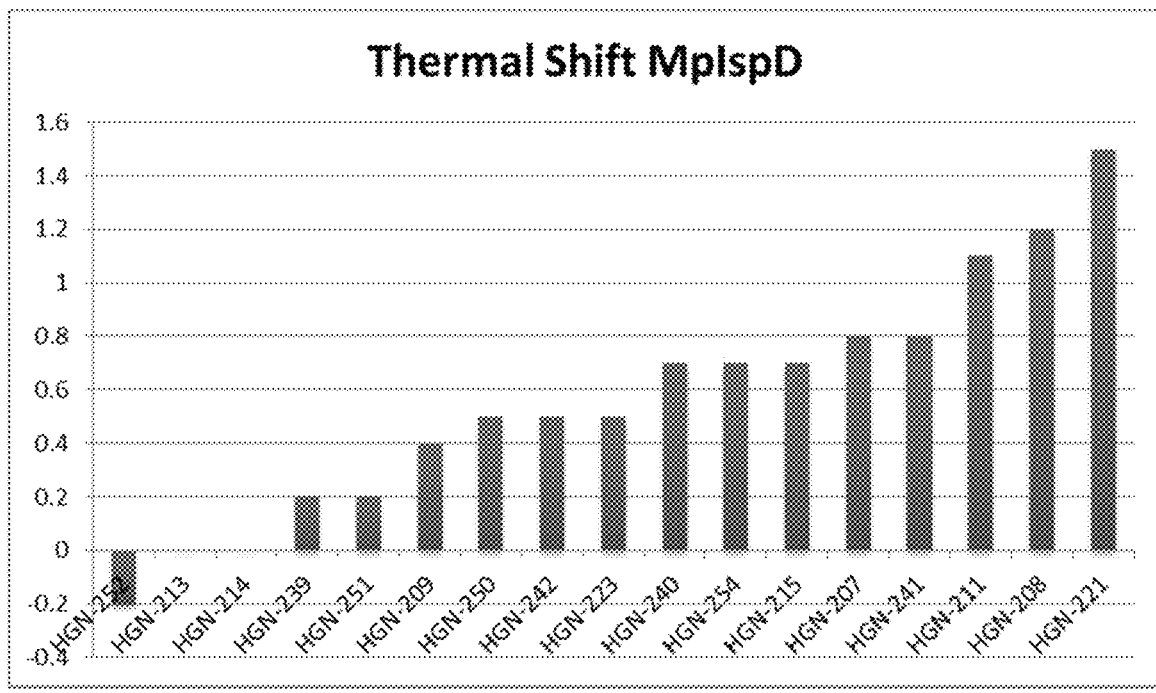
FIG. 50A-50B. Thermal shift data for FIG. 50A, MpIspD and FIG. 50B EcIspD. Values are $\Delta T_m$ given in ° C. for the unfolding event.
Figure 50B:
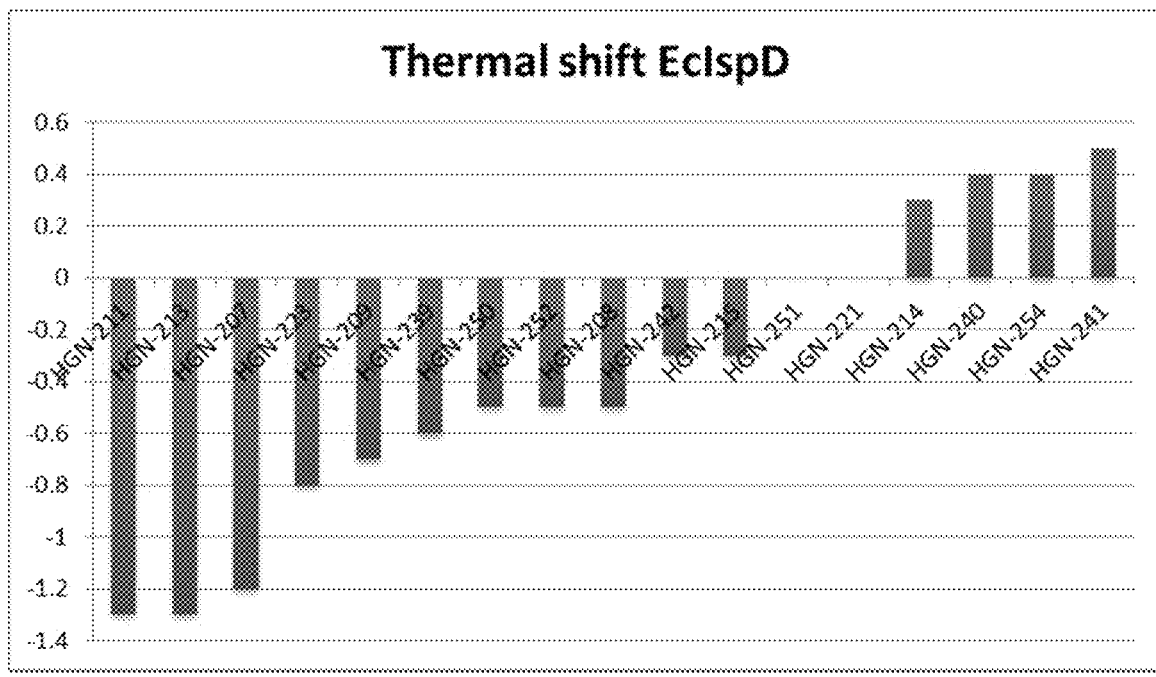

4. Benzimidazole Series (FIGS. 48-49)

2-(1H-benzo[d]imidazole-2-yl)-5-(4-chlorophenyl)-1,3,4-oxadiazole (HGN-421)

To a 100 mL round bottom flask was added 4-chlorobenzoic acid (470.4 mg, 3.0 mmol) and 10 mL thionyl chloride. The solution was heated at reflux for 2 hours with stirring. Excess thionyl chloride was removed under reduced pressure to yield 4-chlorobenzoyl chloride (484.4 mg). The 4-chlorobenzoyl chloride was dissolved in 20 mL pyridine and 1H-benzo[d]imidazole-2-carbohydrazide (287.4 mg, 1.63 mmol) was added. The resulting solution was stirred and heated at reflux for 6 hours. The solution was cooled to room temperature and excess pyridine was removed under reduced pressure to yield crude N'-(4-chlorobenzoyl)-1H-benzo[d]imidazole-2-carbohydrazide. N'-(4-chlorobenzoyl)-1H-benzo[d]imidazole-2-carbohydrazide was scraped off the flask walls to the bottom of the round bottom flask and polyphosphoric acid was added to completely cover the product. The mixture was heated to 150° C. until the polyphosphoric acid was less viscous, and a stirbar was added. The mixture was stirred at 150° C. for 2 hours. The reaction mixture was poured over crushed ice and allowed to sit until precipitate formed. The solution was neutralized with sodium bicarbonate and the solid was filtered and collected. Purification was done via recrystallization to yield 2-(1H-benzo[d]imidazole-2-yl)-5-(4-chlorophenyl)-1,3,4-oxadiazole (121.5 mg, 25.1% yield). $^1$H NMR 300 MHz (DMSO-d$_6$) 8.15 (2H, d, J=8.4 Hz), 7.77-7.69 (4H, m), 7.38-7.34 (2H, m); $^{13}$C NMR 300 MHz (DMSO-d$_6$): 164.22, 163.90, 158.40, 137.64, 137.50, 137.33, 130.23, 130.07, 129.14, 129.01, 124.40, 122.60, 122.34; m.p. 250-255° C.

(mass spec data not available due to low solubility in hplc grade methanol and acetonitrile)

2-(1H-benzo[d]imidazol-2-yl)-5-(4-(trifluoromethyl)phenyl)-1,3,4-oxadiazole (HGN-422)

To a 100 mL round bottom flask was added 4-(trifluoromethyl)benzoic acid (570.4 mg, 3.0 mmol) and 10 mL thionyl chloride. The solution was heated at reflux for 2 hours with stirring. Excess thionyl chloride was removed under reduced pressure to yield 4-(trifluromethyl)benzoyl chloride (620.7 mg). The 4-(trifluoromethyl)benzoyl chloride was dissolved in 20 mL pyridine and 1H-benzo[d]imidazole-2-carbohydrazide (300.2 mg, 1.7 mmol) was added. The resulting solution was stirred and heated at reflux for 6 hours. The solution was cooled to room temperature and excess pyridine was removed under reduced pressure to yield crude N'-(4-(trifluoromethyl)benzoyl)-1H-benzo[d]imidazole-2-carbohydrazide. N'-(4-(trifluoromethyl)benzoyl)-1H-benzo[d]imidazole-2-carbohydrazide was scraped off the flask walls to the bottom of the round bottom flask and polyphosphoric acid was added to completely cover the product. The mixture was heated to 150° C. until the polyphosphoric acid was less viscous, and a stirbar was added. The mixture was stirred at 150° C. for 2 hours. The reaction mixture was poured over crushed ice and allowed to sit until precipitate formed. The solution was neutralized with sodium bicarbonate and the solid was filtered and collected. Purification was done via recrystallization in ethanol to yield 2-(1H-benzo[d]imidazol-2-yl)-5-(4-(trifluoromethyl)phenyl)-1,3,4-oxadiazole (203.6 mg, 36% yield). $^1$H NMR 300 MHz (DMSO-d$_6$) 8.38-8.33 (2H, m), 8.11-8.00 (2H, m), 7.74-7.70 (2H, m), 7.36-7.32 (2H, m); $^{13}$C NMR 300 MHz (DMSO-d$_6$): 164.01, 163.82, 159.06, 139.48, 137.93, 132.48, 132.05, (C—F q 128.17, 126.00, 124.15, 122.39, J=144.5 Hz) 127.43, 127.31, 127.02, 126.97, 126.91, 116.88; m.p. 275-280° C.

LIST OF ABBREVIATIONS $^1$H-NMR Proton Nuclear Magnetic Resonance
$^{13}$C-NMR Carbon-13 Nuclear Magnetic Resonance
AtIspD *Arabidopsis thaliana* IspD
AtIspF *Arabidopsis thaliana* IspF
ATP Adenosine triphosphate
BC *Bacillus cereus*
BpIspF *Burkholderia pseudomallei*
BT *Burkholderia thailandensis*
CDP-ME 4-(cytidine 5'-diphospho)-2-C-methyl-D-erythritol
CDP-MEP 2-phospho-4-(cytidine 5'-diphospho)-2-C-methyl-D-erythritol
cESI-MS Capillary Electrospray Ionization Mass Spectrometry
CP *Corynebacterium pseudodiphtheriae*
CTP Cytidine triphosphate
CX *Corynebacterium xerosis*
DMAPP Dimethylallyl diphosphate
DMSO-d$_6$ Deuterated Dimethyl Sulfoxide DSF Differential Scanning Fluorimetry
DXS 1-deoxy-D-xylulose-5-phosphate synthase
EC *Escherichia coli*
FOL7082 Fragments of Life 7082
GHMP galactose/homoserine/mevalonate/phophomevalonate
HMG 3-hydroxy-3-methylglutaryl
$IC_{50}$ Half Maximal Inhibitory Concentration
IPP Isopentenyl diphosphate
KP *Klebsiella pneumonia*
LeIspE *Lycopersicon esculentum* IspE
MaIspE *Mycobacterium abscessus* IspE
MEcPP 2-C-methyl-D-erythritol 2,4-cyclodiphosphate
MEP 2-C-methyl-D-erythritol 4-phosphate
ML *Micrococcus luteus*
MPD MVA diphosphate decarboxylase
MpIspD *Mycobacterium paratuberculosis* IspD
MS *Mycobacterium smegmatis*
MtIspD *Mycobacterium tuberculosis* IspD
MVA Mevalonic acid
NADPH Nicotinamide adenine dinucleotide phosphate
NOE Nuclear overhauser effect
PA *Pseudomonas aeruginosa*
PfIspD *Plasmodium falciparum* IspD
PMK phospho-MVA kinase
QSAR Quantitative Structure Activity Relationship
SAR Structure Activity Relationship
STD Saturation Transfer Difference
ADMET Absorption, distribution, metabolism, and excretion toxicity
Acetyl-CoA Acetyl-CoA
Amp Ampicillin
BSAT Biological select agents and toxins
CD Circular dichroism
CDC Center for Disease Control and Prevention
CDP Cytidine diphosphate
CMP Cytidine monophosphate
DMSO Dimethyl sulfoxide
DNA Deoxyribonucleic acid
DOXP 1-deoxy-D-xylulose 5-phosphate
DTT Dithiothreitol
FDA US Food and Drug Administration
FPLC Fast protein liquid chromatography
FSAP Federal Select Agent Program
$\Delta H°_{obs}$ Change in enthalpy
HEPES 4-(2-hydroxyethyl)-1-piperazineethanesulfonic acid
HGN Hagen Compound Code
$(His)_6$ Hexahistidine peptide affinity tag
HMBDP (E)-4-hydroxy-3-methylbut-2-enyl diphosphate
HMG-CoA 3-hydroxy-3-methyl-glutaryl-coenzyme A
HPLC High performance liquid chromatography
IMAC Immobilized metal affinity chromatography
IPTG Isopropyl β-D-1 thiogalactopyranoside
IspC 1-deoxy-D-xylulose 5-phosphate reductoisomerase
IspD 2-C-methyl-D-erythritol 4-phosphate cytidylyltransferase
IspE 4-diphosphocytidyl-2-C-methyl-D-erythritol kinase
IspF 2-C-methyl-D-erythritol 2,4-cylcodiphosphate synthase
IspG 4-hydroxy-3-methylbut-2-en-1-yl diphosphate synthase
IspH 4-hydroxy-3-methylbut-2-enyl diphosphate reductase
ITC Isothermal titration calorimetry
Kan Kanamycin
$K_B$ Binding affinity
$K_D$ Dissociation constant
LB Lysogeny broth
MEcDP 2C-methyl-D-erythritol 2,4-cyclodiphosphate
MESG 2-amino-6-mercapto-7-methylpurine riboside
$MgCl_2$ Magnesium Chloride
mRNA Messenger ribonucleic acid
n Stoichiometry
$NaN_3$ Sodium azide
NaCl Sodium chloride
$OD_{600}$ Optical density at 600 nm
PABA Para-aminobenzoic acid
PBS Phosphate buffered saline
PCR Polymerase chain reaction
PDB Protein databank
PNP Purine nucleoside phosphorylase
RNA Ribonucleic acid
$T_m$ Melting temperature
TEV Tobacco etch virus
TRIS Trishydroxyaminomethane
tRNA Transfer ribonucleic acid
USDA US Department of Agriculture
UV Ultra-violet Methods Expression of *Escherichia coli* (Ec) and *Burkholderia thailandensis* (Bt) IspD The gene of EcIspD, in the parent vector pET-14b with the restriction enzymes BgI II at the 5' and the NcoI at the 3' and a hexahistidine peptide tobacco etch virus affinity (($His)_6$-TEV) tag at the N'-terminal (obtained from Odom lab) was transformed into BL21(DE3) competent cells. The gene of Bt IspD was obtained from the SSGCID (ButhA.00168.a) within the AVA0421 vector (a pET-14b derivative), which possesses ampicillin resistance and a N'-terminal $(His)_6$-3C tag. The sequences of the vectors and genes were verified at University of Chicago CRC-DNA sequencing facility. Once transformed with the respective plasmids, the cells are grown on a Lysogeny broth (LB) agar plate with 100 μg/mL ampicillin (amp). A single colony was selected and added to 5 mL of LB with 100 μg/mL amp and grown overnight at 37° C. with shaking (235 rpm). A 50 mL subculture was inoculated using the 5 mL overnight culture, which was subsequently used to inoculate a 1 L LB/amp culture. Cells were grown at 37° C. at 235 RPM until the optical density at 600 nm ($OD_{600}$), determined with a Novaspec® II visible spectrophotometer (Pharmacia Biotech), reached a mid-log phase reading 0.5-0.8. Once at mid-log phase, the cells were induced with 1 mM IPTG for 16 hours at 8° C. at 235 RPM.[76] The cells were pelleted via centrifugation at 8,000 RPM for 15 minutes and stored at −20° C.

Purification of *Escherichia coli* (Ec) and *Burkholderia thailandensis* (Bt) IspD The frozen cells were resuspended in 10 mM Trishydroxyaminomethane (TRIS) buffer and lysed by sonication using a Digital Sonifier 450® (Branson) for six cycles of 20 seconds on/60 seconds off. Once sonicated, the sample was centrifuged at 15,000 RPM for 20 minutes at 4° C. to separate the cell remains and insoluble proteins from the soluble fraction containing IspD. The supernatant was loaded onto a HisTrap HP nickel affinity IMAC column (GE Healthcare Life Sciences) using a BioLogic LP (Bio-Rad Life Sciences) fast protein liquid chromatography (FPLC) systems. The loading buffer was 20 mM imidazole, pH 8.0, 50 mM sodium phosphate, 500 mM NaCl, and 1 mM dithiothreitol (DTT). The protein was eluted using a linear gradient of elution buffer (500 mM imidazole, pH 8.0, 50 mM sodium phosphate, 500 mM NaCl, and 1 mM dithiothreitol (DTT). The fractions containing the IspD enzyme were combined and purified further with a Superdex 75 HiLoad 26/60 size exclusion column (GE Healthcare Life Sciences) using 20 mM TRIS, 150 mM NaCl and 1 mM DTT.

Thermal Stability Determined Using Circular Dichroism

Protein secondary structure can be observed using far ultra-violet (UV) circular dichroism (CD). This method measures the difference between the right and left-handed circularly polarized light in the far UV range (190-250 nm). By following the observed loss of signal related to secondary structure as the temperature was increased, the percent of protein in the native or unfolded form was determined.

All protein samples were dialyzed overnight in 4 L of 20 mM sodium phosphate with 150 mM NaCl at pH 7.0. CD experiments were performed using a Circular Dichroism Spectrophotometer 215 (AVIV Biomedical) with a quartz cuvette containing a 1 mm path length. Wavelength scans were determined from 200 to 250 nm at 25° C., both before and after thermal unfolding. Thermal unfolding scans were read at either 208 nm for Ec IspD or 218 nm for Bt IspD over the temperature range of 25 to 100° C. at 1° C. increments and a temperature equilibrium time of one minute, with a bandwidth of one nanometer and an averaging time of one second. OriginPro 8 Boltzmann fit was used to determine the melting temperature ($T_m$) of each protein.

Thermal Stability Determined Using Differential Scanning Fluorimetry

While CD is a useful technique for observing thermal unfolding of proteins, there are limitations. One of the greatest limitations is that CD typically allows only one sample to be run at a time, and each sample can take several hours to run. Differential scanning fluorimetry (DSF) can follow thermal unfolding of multiple protein samples, at lower volumes, and at a much faster rate than CD. Similar to a CD observed protein thermal melt, DSF will determine the fraction of protein in native and unfolded forms. However, while CD directly measures the protein itself, DSF measures fluorescence of a reporter dye. As a protein unfolds, hydrophobic residues are exposed that interact with the added dye, causing a change in the dye molecule's fluorescence emission profile. The point of 50% native and 50% unfolded is the considered the melting temperature of the protein.

Ligand-protein binding events can be evaluated using DSF by observing the change in melting temperature in the presence and absence of ligand. If a ligands presence increases the melting temperature, the ligand is considered to be a stabilizing compounds, which most often suggests binding to the native form. A decrease in melting temperature would indicate a destabilization of the protein. While the observation of thermal stabilization indicates binding, it does not reveal where the compound binds, whether it binds to the active site, an allosteric site, or even a crevice on the protein surface unrelated to enzyme activity; each would result in stabilization of the protein's native state.

All DSF experiments were performed in 50 mM phosphate buffer at pH 7.4, 150 mM NaCl, 1×SYPRO orange, 2% DMSO and 200 to 1000 nM of the enzyme with a total volume of 25 µL. Final enzyme concentrations used were 2.0 µM for Ec IspD and 0.5 µM for Bt IspD. Samples were measured on a Bio-Rad iQ5 Real-Time PCR (Bio-Rad Life Sciences) using a temperature range of 25 to 95° C. at a rate of 1° C. per minute with the fluorescence measured every 0.5° C. every 10 seconds with wavelengths of 530 and 570 nm used for excitation and emission, respectively. The melting temperature (Tm value) was determined from the first derivative of the graph of relative fluorescence units vs. temperature.

Binding Studies with Isothermal Titration Calorimetry

Binding studies are essential for determining what type of affinity a protein has for a ligand. Isothermal titration calorimetry (ITC) allows the ability to determine the binding affinity ($K_B$) which is characterized as the ratio of the protein (or macromolecule) ligand complex concentration [ML] by the concentration of free macromolecule [M] and ligand [L], as presented in the following equation:

$$K_B = \frac{[ML]}{[M][L]}. \qquad \text{Eq. 2-1}$$

The equilibrium dissociation constant ($K_D$) can be obtained by taking the inverse of the binding affinity constant:

$$K_D = \frac{1}{K_B}. \qquad \text{Eq. 2-2}$$

Along with the binding affinity, the enthalpy change ($\Delta H°_{obs}$) and stoichiometry (n) are determined directly from an ITC experiment, which also allows calculation of the change in entropy ($\Delta S°_{obs}$).

ITC studies were performed with a Microcal VP-ITC titration calorimeter (Malvern Instruments). Proteins were dialyzed overnight against four liters of buffer (20 mM sodium phosphate, 150 mM NaCl, pH 7.4). Compounds were dissolved in DMSO and brought to concentration with the dialysis buffer, with a maximum DMSO concentration of 10% by volume, and centrifuged at 10,000 RPM for 10 minutes. DMSO concentrations were matched between the protein and ligand. The dialysis buffer was used for all sample dilutions to ensure buffers matching between the titrant and titrate, thus minimizing the excess heat due to buffer mismatch. The Pace method was utilized for the determination of the extinction coefficients at 280 nm for Ec IspD (30,940 $M^{-1}$ $cm^{-1}$) and Bt IspD (41,940 $M^{-1}$ $cm^{-1}$). Cytidine triphosphate's extinction coefficient was 9,100 $M^{-1}$ $cm^{-1}$. The absorbance values of protein and CTP solutions were determined using the NanoDrop (in triplicate). All other compound concentrations were determined by dry weight. ITC experiments were performed with IspD in the cell and ligand in the syringe, which is at 100 times the concentration of the sample in the cell due to the low predicted affinities for IspD.

The initial injection volume was 2 µL (omitted) followed by 27 10 µL injections, every 240 seconds. Samples were run at 25° C., at pH 7.4, with a stirring speed of 307 RPM. Dilution runs were performed to allow determination of background heats caused by solution mismatch and instrument noise. Dilution runs were performed with ligand (at the same concentration as in the experiment run) in the syringe titrated into the dialysis buffer in the cell. Data were fit using OriginPro 7 with the ITC add-on by the manufacturer.

Enzyme Inhibition Determined Using EnzChek® Phosphate Assay Kit

Thermal shift assays allow observation of binding. However, binding does not always equate to activity. An enzymatic assay typically follows a decrease in reactant concentration, an increase in product concentration, or the formation of a byproduct. Here, for the plate-based assay, IspD converts MEP to CDP-ME pyrophosphate, which in turn is converted to inorganic phosphate ($P_i$) with the enzyme inorganic pyrophosphatase. The EnzChek® Phosphate Assay kit follows the formation of the inorganic phosphate through a reaction with 2-amino-6-mercapto-7-methylpurine riboside (MESG) and the enzyme purine nucleoside phosphorylase (PNP). This reaction converts the MESG into ribose 1-phosphate and 2-amino-6-mercapto-7-methylpurine resulting in a spectrophotometric shift in a maximum absorbance from 330 nm to 360 nm. Reactions were performed in 50 µL final volumes in 96-well clear flat bottom plates, and were initiated by addition of 50 ng purified Ec IspD. Absorbance at 360 nm was measured every 31 seconds for 20 minutes on a Synergy 2 Multi-Mode plate reader (BioTek), preheated to 37° C. Final concentration of reagents was as follows: 1×EnzChek® reaction buffer (50 mM Tris pH 7.5, 1 mM magnesium chloride ($MgCl_2$), 100 µM sodium azide ($NaN_3$)), 0.2 mM MESG, 1 U/ml PNP, 1 U/mL inorganic Pyrophosphatase (NEB), 200 mM CMP (Sigma), and 50 µM MEP (Echelon).

Purification of Ec and Bt IspD

Both *Escherichia coli* and *Burkholderia thailandensis* IspD were purified using a nickel affinity column with a 20-500 mM gradient elution using imidazole. Fractions associated with the UV absorbance peak in the chromatogram, verified with a NanoDrop 2000c spectrophotometer (Thermo Scientific), were combined and concentrated to 10 mL using a spin concentrator. The resulting concentrate was further purified using a size exclusion chromatography column (Superdex 75 HiLoad 26/60), and fractions related to the UV absorbance peak of IspD were collected, combined, and concentrated. The protein was aliquoted and stored at −80° C. until needed for thermal shift (DSF), circular dichroism and enzymatic assays.

Melting Point Determination of IspD

Circular Dichroism was used to determine the thermal stability of Ec and Bt IspD. Prior to performing CD, 20 mM of each protein was dialyzed in four liters of buffer (20 mM phosphate at pH 7.0 and 150 mM NaCl) overnight. Wavelength scans were run before the thermal melt to get a baseline reading which confirmed the mainly alpha helical secondary structure of the proteins. Full scans were repeated post-thermal melt to characterize the protein's reversibility. Both species show loss of secondary structure which may suggest the thermal unfolding to be non-reversible under the conditions of the experiment. The thermal stability of each of the proteins was observed at a single wavelength over a temperature range of 25–100° C. The melting temperature ($T_m$) was determined to be approximately 66° C. for Ec IspD and 53.5° C. for Bt IspD, which will be used as reference temperatures for further thermal shift assays.

Thermal Shift of IspD to Determine Binding of Compounds

Prior to testing compounds directly against IspD, a concentration test was performed to determine the lowest concentration of IspD that would still provide a reasonable change in signal upon unfolding. Comparing the melting temperature with and without the presence of compound can result in a thermal shift, which may indicate binding. The oxadiazole series were evaluated with very little observed thermal shifts against Ec IspD.

Binding Studies of Bt IspD with CTP

ITC studies were performed to observe the dissociation constant along with thermodynamic properties of the reactant CTP with Bt IspD. Due to the low affinity, the binding stoichiometry was fixed at two CTPs per dimer during data analysis. The ΔH° of CTP showed to have a value of −6.991±1.749 kcal/mol and an unfavorable entropic contribution of −TΔS of 5.6±1.838. $K_{D\ app}$ of CTP was shown to be in the millimolar range.

TABLE 1

Thermal Shift Assay Results -Compounds tested against *Mycobacterium tuberculosis* IspD (MtIspD) and *Lycopericon esculentum* IspE (LeIspE).

| Sample | Structure | MtIspD melting temp (° C.) | MtIspD melting point change (° C.) | LeIspE melting temp (° C.) | LeIspE melting point change (° C.) |
|---|---|---|---|---|---|
| HGN-207 | 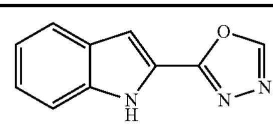 | 49.5 | 1.5 | 48.25 | −1.25 |
| HGN-209 | 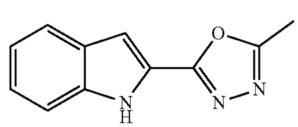 | 49.5 | 1.5 | 47.25 | −2.25 |
| HGN-250 | 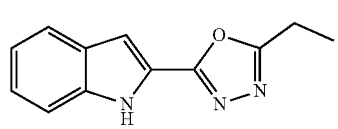 [SMILES: CCc1nnc(-c2cc3ccccc3[nH]2)o1] | 48.8 | 0.8 | 46.75 | −2.75 |
| HGN-240 | 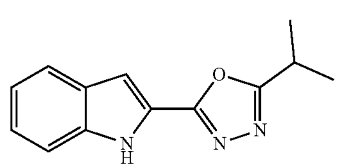 [SMILES: CC(C)c1nnc(-c2cc3ccccc3[nH]2)o1] | 48.8 | 0.8 | 48.00 | −1.50 |

TABLE 1-continued

Thermal Shift Assay Results -Compounds tested against *Mycobacterium tuberculosis* IspD (MtIspD) and *Lycopericon esculentum* IspE (LeIspE).

| Sample | Structure | MtIspD melting temp (° C.) | MtIspD melting point change (° C.) | LeIspE melting temp (° C.) | LeIspE melting point change (° C.) |
|---|---|---|---|---|---|
| HGN-239 | 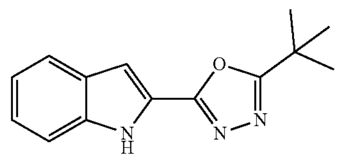 [SMILES: CC(C)(C)c1nnc(-c2cc3ccccc3[nH]2)o1] | 49.5 | 1.5 | 47.00 | −2.50 |
| HGN-211 | 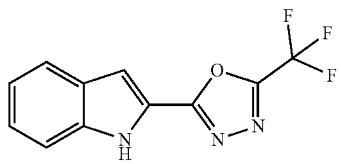 [SMILES: FC(F)(F)c1nnc(-c2cc3ccccc3[nH]2)o1] | 49.3 | 1.3 | 48.75 | −0.75 |
| HGN-252 | 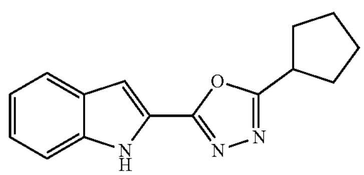 [SMILES: c1ccc2[nH]c(-c3nnc(C4CCCC4)o3)cc2c1] | 49.5 | 1.5 | 47.00 | −2.50 |
| HGN-254 | 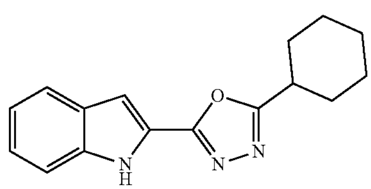 [SMILES: c1ccc2[nH]c(-c3nnc(C4CCCCC4)o3)cc2c1] | 48.5 | 0.5 | 47.50 | −2.00 |
| HGN-241 | 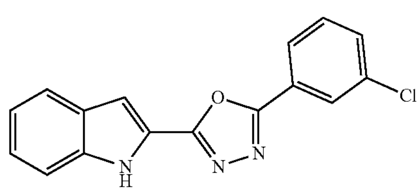 [SMILES: Clc1cccc(-c2nnc(-c3cc4ccccc4[nH]3)o2)c1] | 48.5 | 0.5 | 47.75 | −1.75 |
| HGN-213 | 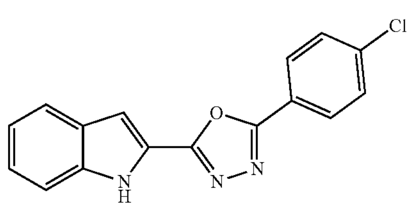 | 48.8 | 0.8 | 47.50 | −2.00 |
| HGN-214 | 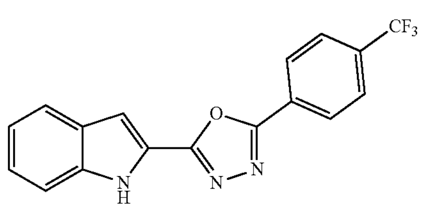 [SMILES: FC(F)(F)c1ccc(-c2nnc(-c3cc4ccccc4[nH]3)o2)cc1] | 49.8 | 1.8 | 48.50 | −1.00 |

TABLE 1-continued

Thermal Shift Assay Results -Compounds tested against *Mycobacterium tuberculosis* IspD (MtIspD) and *Lycopericon esculentum* IspE (LeIspE).

| Sample | Structure | MtIspD melting temp (° C.) | MtIspD melting point change (° C.) | LeIspE melting temp (° C.) | LeIspE melting point change (° C.) |
| --- | --- | --- | --- | --- | --- |
| HGN-242 | 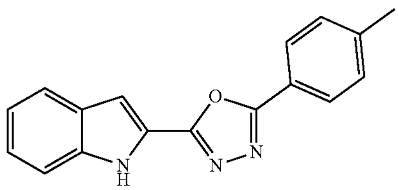 [SMILES: Cc1ccc(-c2nnc(-c3cc4ccccc4[nH]3)o2)cc1] | 48.8 | 0.8 | 47.75 | −1.75 |
| HGN-223 | 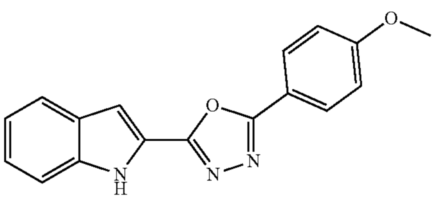 [SMILES: COc1ccc(-c2nnc(-c3cc4ccccc4[nH]3)o2)cc1] | 48.0 | 0.0 | 49.25 | −0.25 |
| HGN-339 | 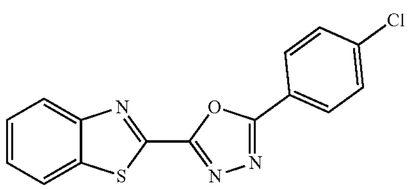 [SMILES: Clc1ccc(-c2nnc(-c3nc4ccccc4s3)o2)cc1] | 49.3 | 1.3 | 47.50 | −2.00 |
| HGN-337 | 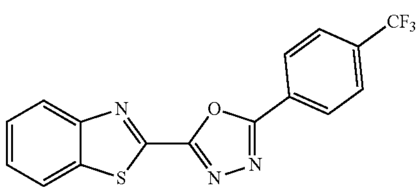 [SMILES: FC(F)(F)c1ccc(-c2nnc(-c3nc4ccccc4s3)o2)cc1] | 48.8 | 0.8 | 47.75 | −1.75 |
| HGN-338 | 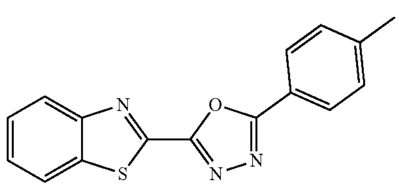 [SMILES: Cc1ccc(-c2nnc(-c3nc4ccccc4s3)o2)cc1] | 48.0 | 0.0 | 48.00 | −1.50 |
| HGN-336 | 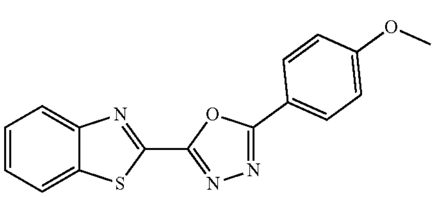 [SMILES: COc1ccc(-c2nnc(-c3nc4ccccc4s3)o2)cc1] | 49.5 | 1.5 | 48.25 | −1.25 |
| HGN-333 | 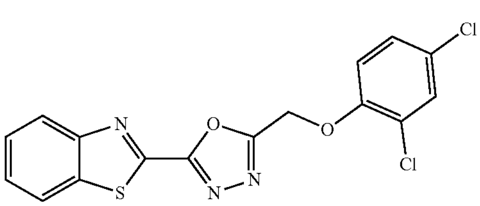 [SMILES: Clc1ccc(OCc2nnc(-c3nc4ccccc4s3)o2)c(Cl)c1] | 49.3 | 1.3 | 47.75 | −1.75 |

TABLE 1-continued

Thermal Shift Assay Results -Compounds tested against *Mycobacterium tuberculosis* IspD (MtIspD) and *Lycopericon esculentum* IspE (LeIspE).

| Sample | Structure | MtIspD melting temp (° C.) | MtIspD melting point change (° C.) | LeIspE melting temp (° C.) | LeIspE melting point change (° C.) |
|---|---|---|---|---|---|
| HGN-334 | 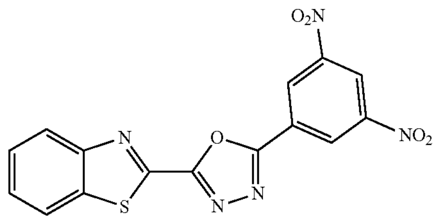 [SMILES: O=[N+]([O-])c1cc(-c2nnc(-c3nc4ccccc4s3)o2)cc([N+](=O)[O-])c1] | 48.0 | 0.0 | 48.00 | −1.50 |
| HGN-335 | 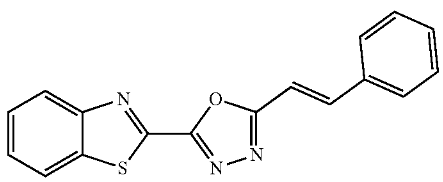 [SMILES: C(=C\c1nnc(-c2nc3ccccc3s2)o1)/c1ccccc1] | 48.5 | 0.5 | 48.00 | −1.50 |
| HGN-421 | 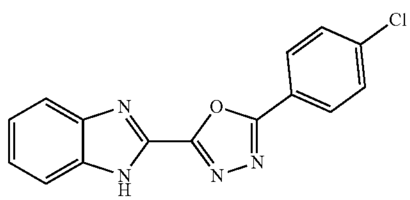 [SMILES: Clc1ccc(-c2nnc(-c3nc4ccccc4[nH]3)o2)cc1] | 48.8 | 0.8 | 48.00 | −1.50 |
| HGN-422 | 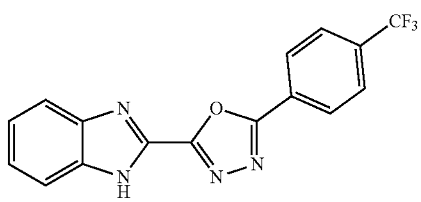 [SMILES: FC(F)(F)c1ccc(-c2nnc(-c3nc4ccccc4[nH]3)o2)cc1] | 49.0 | 1.0 | 46.25 | −3.25 |
| HGN-221 | 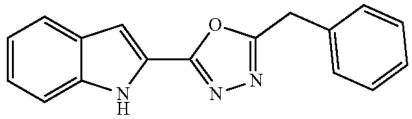 [SMILES: c1ccc(Cc2nnc(-c3cc4ccccc4[nH]3)o2)cc1] | 48.5 | 0.5 | 49.50 | 0.00 |
| HGN-215 | 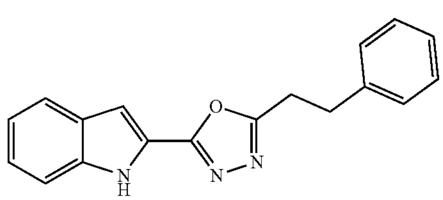 [SMILES: c1ccc(CCc2nnc(-c3cc4ccccc4[nH]3)o2)cc1] | 48.8 | 0.8 | 47.50 | −2.00 |
| HGN-287 | 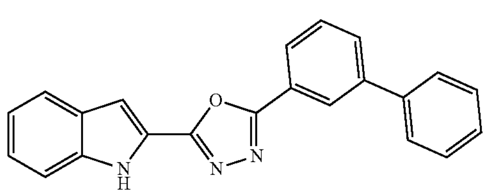 [SMILES: c1ccc(-c2cccc(-c3nnc(-c4cc5ccccc5[nH]4)o3)c2)cc1] | 48.5 | 0.5 | 49.25 | −0.25 |

TABLE 1-continued

Thermal Shift Assay Results -Compounds tested against *Mycobacterium tuberculosis* IspD (MtIspD) and *Lycopericon esculentum* IspE (LeIspE).

| Sample | Structure | MtIspD melting temp (° C.) | MtIspD melting point change (° C.) | LeIspE melting temp (° C.) | LeIspE melting point change (° C.) |
|---|---|---|---|---|---|
| HGN-288 | 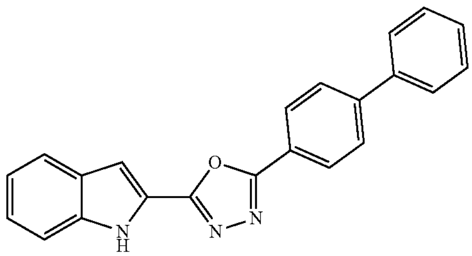 [SMILES: c1ccc(-c2ccc(-c3nnc(-c4cc5ccccc5[nH]4)o3)cc2)cc1] | 49.0 | 1.0 | 48.00 | −1.50 |
| HGN-340 | 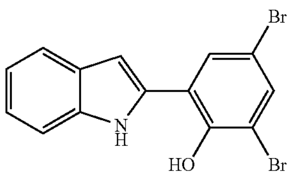 [SMILES: Oc1c(Br)cc(Br)cc1-c1cc2ccccc2[nH]1] | 49.3 | 1.3 | 50.00 | 0.50 |

TABLE 2

Lettuce Leaf Assay Results- In vivo assay results of compounds tested against lettuce seeds to test for bleaching, root development inhibition, and germination inhibition. Ranking is a qualitative measure from 0 (no effect) to 5 (complete inhibition or bleaching).

| Sample | Structure | Conc. | Bleaching | Root Dev. | Germination |
|---|---|---|---|---|---|
| HGN-207 | 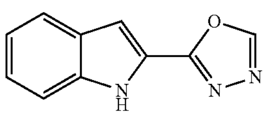 [SMILES: c1ccc2[nH]c(-c3nnco3)cc2c1] | 1.0 mM | 3 | 0 | 2 |
|  |  | 0.5 mM | 2 | 0 | 2 |
| HGN-209 | 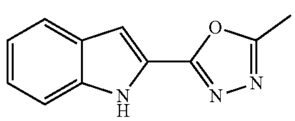 | 1.0 mM | 0 | 1 | 2 |
|  |  | 0.5 mM | 0 | 1 | 1 |
| HGN-250 | 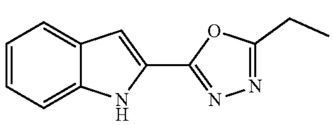 [SMILES: CCc1nnc(-c2cc3ccccc3[nH]2)o1] | 1.0 mM | 0 | 0 | 3 |
|  |  | 0.5 mM | 0 | 0 | 1 |
| HGN-240 | 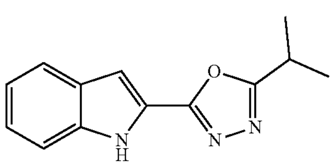 [SMILES: CC(C)c1nnc(-c2cc3ccccc3[nH]2)o1] | 1.0 mM | 0 | 0 | 2 |
|  |  | 0.5 mM | 0 | 0 | 1 |
| HGN-239 | 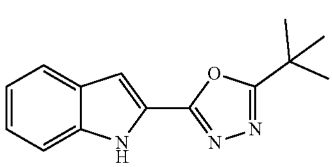 [SMILES: CC(C)(C)c1nnc(-c2cc3ccccc3[nH]2)o1] | 1.0 mM | 0 | 0 | 1 |
|  |  | 0.5 mM | 0 | 0 | 0 |

TABLE 2-continued

Lettuce Leaf Assay Results- In vivo assay results of compounds tested against lettuce seeds to test for bleaching, root development inhibition, and germination inhibition. Ranking is a qualitative measure from 0 (no effect) to 5 (complete inhibition or bleaching).

| Sample | Structure | Conc. | Bleaching | Root Dev. | Germination |
|---|---|---|---|---|---|
| HGN-211 | 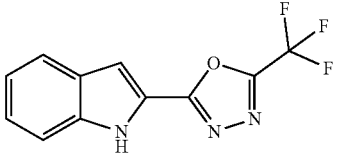 [SMILES: FC(F)(F)c1nnc(-c2cc3ccccc3[nH]2)o1] | 1.0 mM<br>0.5 mM | 0<br>0 | 0<br>0 | 2<br>1 |
| HGN-252 | 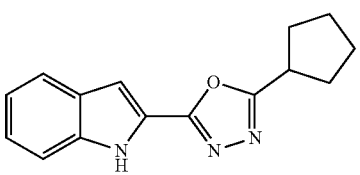 [SMILES: c1ccc2[nH]c(-c3nnc(C4CCCC4)o3)cc2c1] | 1.0 mM<br>0.5 mM | 0<br>0 | 0<br>0 | 2<br>1 |
| HGN-254 | 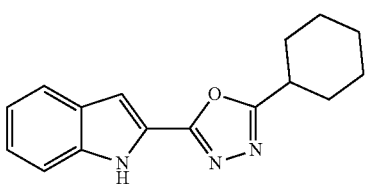 [SMILES: c1ccc2[nH]c(-c3nnc(C4CCCCC4)o3)cc2c1] | 0.3 mM<br>0.15 mM | 0<br>0 | 0<br>0 | 0<br>0 |
| HGN-241 | 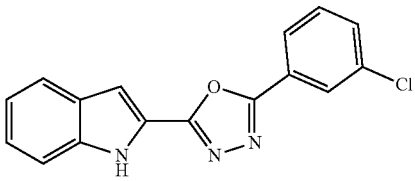 [SMILES: Clc1cccc(-c2nnc(-c3cc4ccccc4[nH]3)o2)c1] | 0.2 mM | 0 | 0 | 1 |
| HGN-213 | 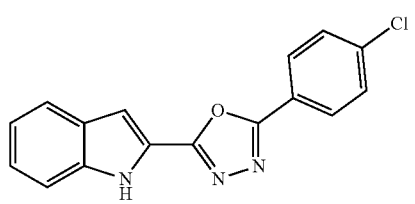 | 0.2 mM | 0 | 0 | 1 |
| HGN-214 | 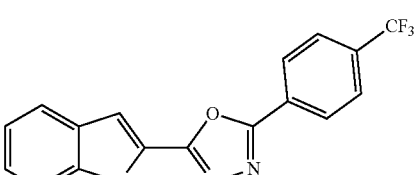 | 1.0 mM<br>0.5 mM<br>0.2 mM | 0<br>0<br>0 | 0<br>0<br>0 | 3<br>1<br>0 |
| HGN-242 | 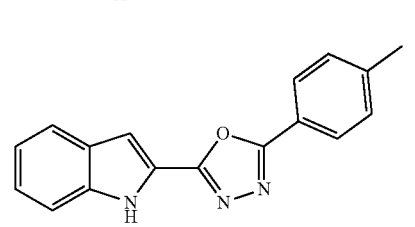 [SMILES: Cc1ccc(-c2nnc(-c3cc4ccccc4[nH]3)o2)cc1] | 1.0 mM<br>0.5 mM | 0<br>0 | 0<br>0 | 4<br>2 |

TABLE 2-continued

Lettuce Leaf Assay Results- In vivo assay results of compounds tested against lettuce seeds to test for bleaching, root development inhibition, and germination inhibition. Ranking is a qualitative measure from 0 (no effect) to 5 (complete inhibition or bleaching).

| Sample | Structure | Conc. | Bleaching | Root Dev. | Germination |
|---|---|---|---|---|---|
| HGN-223 | 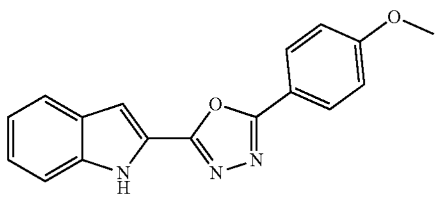 [SMILES: COc1ccc(-c2nnc(-c3cc4ccccc4[nH]3)o2)cc1] | 1.0 mM | 0 | 0 | 4 |
| | | 0.5 mM | 0 | 0 | 1 |
| HGN-339 | 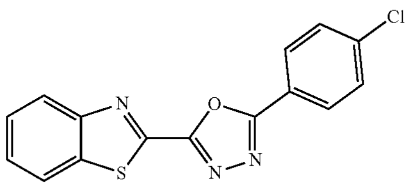 [SMILES: Clc1ccc(-c2nnc(-c3nc4ccccc4s3)o2)cc1] | 0.3 mM | 0 | 0 | 0 |
| | | 0.15 mM | 0 | 0 | 0 |
| HGN-337 | 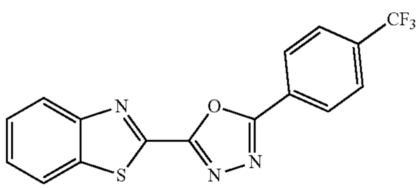 [SMILES: FC(F)(F)c1ccc(-c2nnc(-c3nc4ccccc4s3)o2)cc1] | 0.3 mM | 0 | 0 | 0 |
| | | 0.15 mM | 0 | 0 | 0 |
| HGN-338 | 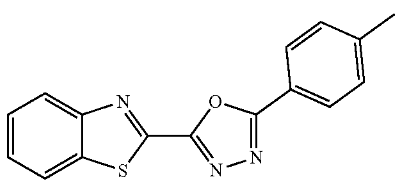 [SMILES: Cc1ccc(-c2nnc(-c3nc4ccccc4s3)o2)cc1] | 0.3 mM | 0 | 0 | 1 |
| | | 0.15 mM | 0 | 0 | 0 |
| HGN-336 | 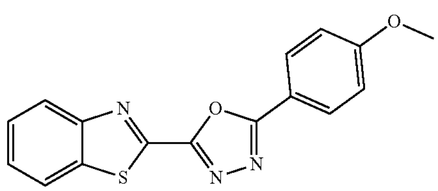 [SMILES: COc1ccc(-c2nnc(-c3nc4ccccc4s3)o2)cc1] | 0.3 mM | 0 | 0 | 0 |
| | | 0.15 mM | 0 | 0 | 1 |
| HGN-333 | 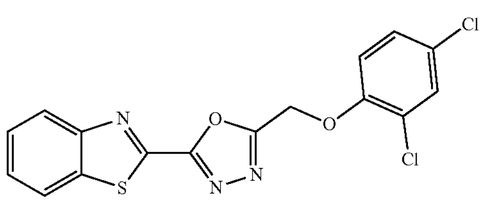 [SMILES: Clc1ccc(OCc2nnc(-c3nc4ccccc4s3)o2)c(Cl)c1] | 0.3 mM | 0 | 0 | 0 |
| | | 0.15 mM | 0 | 0 | 0 |
| HGN-334 | 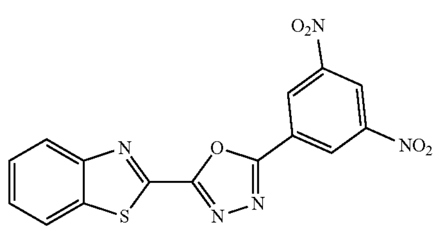 [SMILES: O=[N+]([O-])c1cc(-c2nnc(-c3nc4ccccc4s3)o2)cc([N+](=O)[O-])c1] | 0.3 mM | 0 | 0 | 0 |
| | | 0.15 mM | 0 | 0 | 0 |

TABLE 2-continued

Lettuce Leaf Assay Results- In vivo assay results of compounds tested against lettuce seeds to test for bleaching, root development inhibition, and germination inhibition. Ranking is a qualitative measure from 0 (no effect) to 5(complete inhibition or bleaching).

| Sample | Structure | Conc. | Bleaching | Root Dev. | Germination |
|---|---|---|---|---|---|
| HGN-335 | 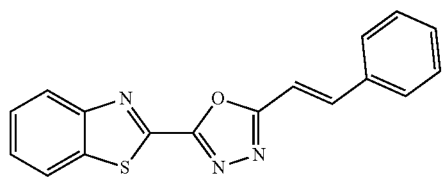 [SMILES: C(=C\c1nnc(-c2nc3ccccc3s2)o1)/c1ccccc1] | 0.2 mM<br>0.1 mM | 0<br>0 | 0<br>0 | 0<br>0 |
| HGN-421 | 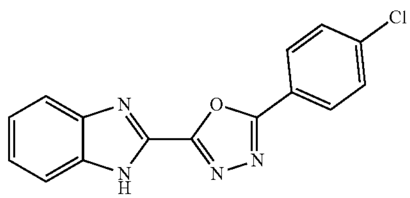 [SMILES: Clc1ccc(-c2nnc(-c3nc4ccccc4[nH]3)o2)cc1] | 0.3 mM<br>0.15 mM | 0<br>0 | 0<br>0 | 1<br>1 |
| HGN-422 | 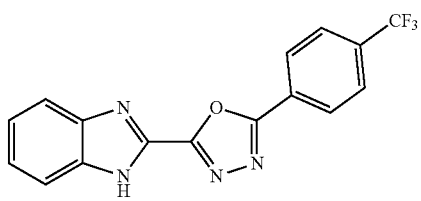 [SMILES: FC(F)(F)c1ccc(-c2nnc(-c3nc4ccccc4[nH]3)o2)cc1] | 0.3 mM<br>0.15 mM | 0<br>0 | 0<br>0 | 0<br>0 |
| HGN-221 | 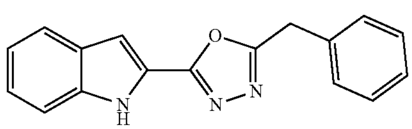 [SMILES: c1ccc(Cc2nnc(-c3cc4ccccc4[nH]3)o2)cc1] | 0.3 mM<br>0.15 mM | 0<br>0 | 0<br>0 | 0<br>0 |
| HGN-215 | 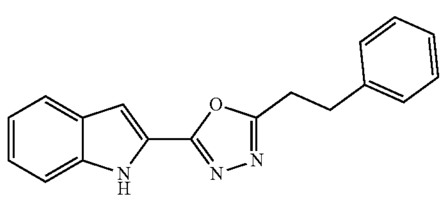 [SMILES: c1ccc(CCc2nnc(-c3cc4ccccc4[nH]3)o2)cc1] | 0.3 mM<br>0.15 mM | 0<br>0 | 0<br>0 | 0<br>0 |
| HGN-287 | 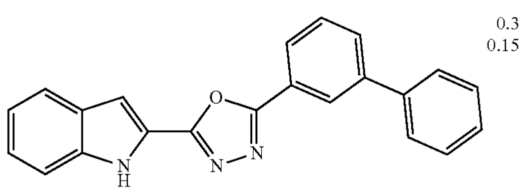 | 0.3 mM<br>0.15 mM | 0<br>0 | 0<br>0 | 0<br>0 |
| HGN-288 | 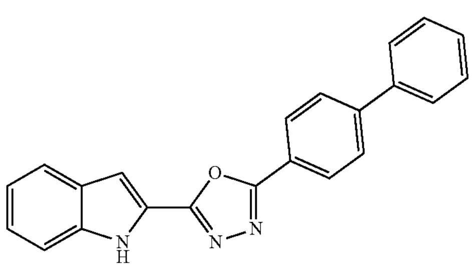 [SMILES: c1ccc(-c2ccc(-c3nnc(-c4cc5ccccc5[nH]4)o3)cc2)cc1] | 0.2 mM<br>0.1 mM | 0<br>0 | 0<br>0 | 0<br>0 |

TABLE 2-continued

Lettuce Leaf Assay Results- In vivo assay results of compounds tested against lettuce seeds to test for bleaching, root development inhibition, and germination inhibition. Ranking is a qualitative measure from 0 (no effect) to 5(complete inhibition or bleaching).

| Sample | Structure | Conc. | Bleaching | Root Dev. | Germination |
|---|---|---|---|---|---|
| HGN-340 | (indole-phenol with 2 Br and OH) | 0.3 mM | 0 | 0 | 0 |
|  |  | 0.15 mM | 0 | 0 | 0 |

TABLE 3

Assay Results - Compounds were tested against AtIspD, LeIspE, and AtIspF and results are given as IC50 values. (University of Hamburg, Boris Illarionov, director Markus Fischer)

| HGN # | X | Y | R₁ | AtIspD IC$_{50}$, μM | LeIspE IC$_{50}$, μM | AtIspF IC$_{50}$, μM |
|---|---|---|---|---|---|---|
| 207 | C | NH | R—H | >1000 | >1000 | >1000 |
| 209 | C | NH | R—CH₃ | >1000 | >1000 | >1000 |
| 250 | C | NH | R-ethyl | >1000 | >1000 | >1000 |
| 240 | C | NH | R-isopropyl | >1000 | >1000 | >1000 |
| 239 | C | NH | R-tert-butyl | >1000 | >1000 | >1000 |
| 212 | C | NH | R-CH₂-O-CH₃ | >1000 | >1000 | >1000 |
| 211 | C | NH | R—CF₃ | >1000 | >1000 | >1000 |
| 251 | C | NH | R-cyclobutyl | >1000 | >1000 | >1000 |
| 252 | C | NH | R-cyclopentyl | >1000 | >1000 | >1000 |
| 254 | C | NH | R-cyclohexyl | 322 ± 14 | >1000 | >1000 |
| 208 | C | NH | R-phenyl | 342 ± 42 | 165 ± 47 | >1000 |
| 241 | C | NH | R-(4-chlorophenyl) | >1000 | 149 ± 41 | >1000 |

TABLE 3-continued
Assay Results - Compounds were tested against AtIspD, LeIspE, and AtIspF and results are given as IC50 values.
(University of Hamburg, Boris Illarionov, director Markus Fischer)
| | | | | | | |
|---|---|---|---|---|---|---|
| 213 | C | NH |  | 490 ± 91 | 326 ± 29 | >1000 |
| 214 | C | NH | 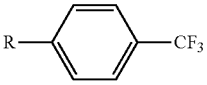 | >1000 | 269 ± 23 | >1000 |
| 242 | C | NH |  | 225 ± 17 | 109 ± 35 | >1000 |
| 223 | C | NH |  | 209 ± 29 | 126 ± 12 | >1000 |
| 339 | N | S |  | 158 ± 14 | >500 | >500 |
| 337 | N | S | 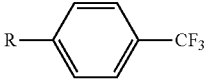 | >500 | >500 | >500 |
| 338 | N | S |  | >500 | >500 | >500 |
| 336 | N | S |  | >500 | 493 ± 49 | >500 |
| 333 | N | S | 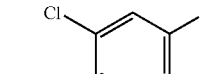 | 151 ± 28 | 31 ± 17 | 291 ± 26 |
| 334 | N | S | 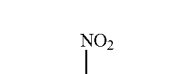 | >500 | >500 | >500 |
| 335 | N | S | 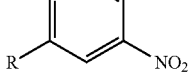 | >500 | >500 | >500 |
| 421 | N | NH | 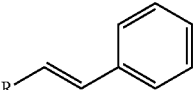 | 88 ± 20 | 298 ± 49 | 484 ± 95 |
| 422 | N | NH | 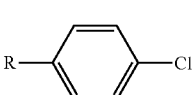 | 251 ± 21 | 267 ± 12 | >500 |
| 221 | C | NH | 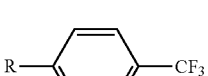 | 636 ± 68 | >1000 | >1000 |

TABLE 3-continued

Assay Results - Compounds were tested against AtIspD, LeIspE, and AtIspF and results are given as IC50 values.
(University of Hamburg, Boris Illarionov, director Markus Fischer)

| HGN # | | | Structure | AtIspD | LeIspE | AtIspF |
|---|---|---|---|---|---|---|
| 215 | C | NH |  | >1000 | 430 ± 48 | >1000 |
| 287 | C | NH | 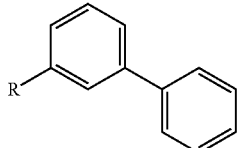 | 501 ± 82 | >1000 | >1000 |
| 288 | C | NH | 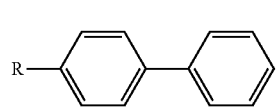 | 255 ± 35 | >1000 | >1000 |

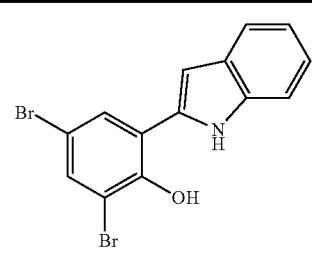

| HGN # | AtIspD IC$_{50}$, μM | LeIspE IC$_{50}$, μM | AtIspF IC$_{50}$, μM |
|---|---|---|---|
| 340 | 50 ± 2 | >500 | 470 ± 116 |

TABLE 4

Results from Antibacterial Preliminary Screening- Compounds are given scores from 0-3 in the preliminary screening in which 0 represents no inhibition and 3 is comparable to commercial antibiotic control.

| HGN# | Structure | BT | MS | CX | CP | EC | KP | ML | BC | PA |
|---|---|---|---|---|---|---|---|---|---|---|
| 207 | 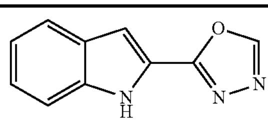 | 0 | 0 | 0 | 0 | 0 | 0 | 0 | 0 | 0 |
| 209 | 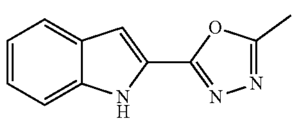 | 0 | 0 | 0 | 0 | 0 | 0 | 0 | 0 | 0 |
| 250 | 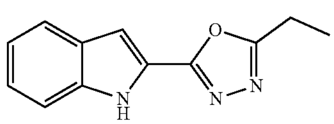 [SMILES: CCc1nnc(-c2cc3ccccc3[nH]2)o1] | 0 | 0 | 0 | 0 | 0 | 0 | 0 | 0 | 0 |
| 240 | 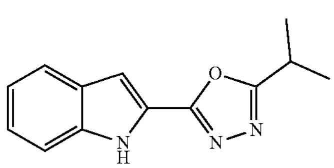 [SMILES: CC(C)c1nnc(-c2cc3ccccc3[nH]2)o1] | 0 | 0 | 0 | 0 | 0 | 0 | 0 | 0 | 0 |

TABLE 4-continued

Results from Antibacterial Preliminary Screening- Compounds are given scores from 0-3 in the preliminary screening in which 0 represents no inhibition and 3 is comparable to commercial antibiotic control.

| HGN# | Structure | BT | MS | CX | CP | EC | KP | ML | BC | PA |
|---|---|---|---|---|---|---|---|---|---|---|
| 239 | 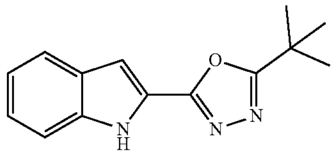 [SMILES: CC(C)(C)c1nnc(-c2cc3ccccc3[nH]2)o1] | 0 | 0 | 0 | 0 | 0 | 0 | 0 | 0 | 0 |
| 212 | 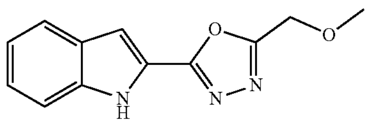 [SMILES: COCc1nnc(-c2cc3ccccc3[nH]2)o1] | 0 | 0 | 0 | 0 | 0 | 0 | 0 | 0 | 0 |
| 211 | 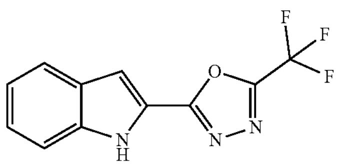 [SMILES: FC(F)(F)c1nnc(-c2cc3ccccc3[nH]2)o1] | 0 | 0 | 0 | 0 | 0 | 0 | 0 | 0 | 0 |
| 251 | 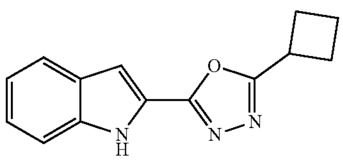 [SMILES: c1ccc2[nH]c(-c3nnc(C4CCC4)o3)cc2c1] | 0 | 0 | 0 | 0 | 0 | 0 | 0 | 0 | 0 |
| 252 | 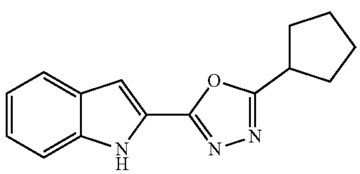 [SMILES: c1ccc2[nH]c(-c3nnc(C4CCCC4)o3)cc2c1] | 0 | 0 | 0 | 0 | 0 | 0 | 0 | 0 | 0 |
| 254 | 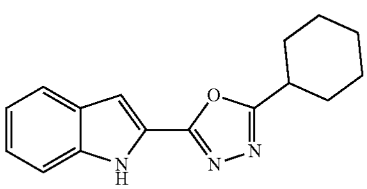 [SMILES: c1ccc2[nH]c(-c3nnc(C4CCCCC4)o3)cc2c1] | 0 | 0 | 0 | 0 | 0 | 0 | 0 | 0 | 0 |
| 208 | 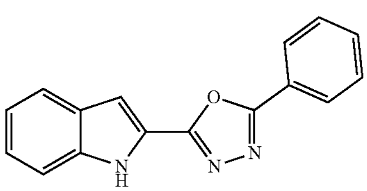 [SMILES: c1ccc(-c2nnc(-c3cc4ccccc4[nH]3)o2)cc1] | 0 | 0 | 0 | 0 | 0 | 0 | 0 | 0 | 0 |
| 241 | 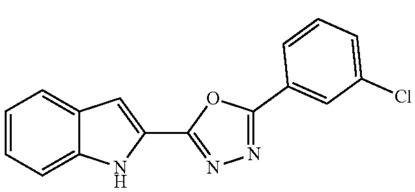 [SMILES: Clc1cccc(-c2nnc(-c3cc4ccccc4[nH]3)o2)c1] | 0 | 0 | 0 | 0 | 0 | 0 | 0 | 0 | 0 |

TABLE 4-continued

Results from Antibacterial Preliminary Screening- Compounds are given scores from 0-3 in the preliminary screening in which 0 represents no inhibition and 3 is comparable to commercial antibiotic control.

| HGN# | Structure | BT | MS | CX | CP | EC | KP | ML | BC | PA |
|---|---|---|---|---|---|---|---|---|---|---|
| 213 | indole-oxadiazole-C6H4-Cl | 0 | 0 | 0 | 0 | 0 | 0 | 0 | 0 | 0 |
| 214 | indole-oxadiazole-C6H4-CF3 | 0 | 0 | 0 | 0 | 0 | 0 | 0 | 0 | 0 |
| 242 | indole-oxadiazole-C6H4-CH3 | 0 | 0 | 0 | 0 | 0 | 0 | 0 | 0 | 0 |
| 223 | indole-oxadiazole-C6H4-OCH3 | 0 | 0 | 0 | 0 | 0 | 0 | 0 | 0 | 0 |
| 339 | benzothiazole-oxadiazole-C6H4-Cl | 0 | 0 | 0 | 0 | 0 | 0 | 0 | 0 | 0 |
| 337 | benzothiazole-oxadiazole-C6H4-CF3 | 0 | 0 | 0 | 0 | 0 | 0 | 0 | 0 | 0 |
| 338 | benzothiazole-oxadiazole-C6H4-CH3 | 0 | 0 | 0 | 0 | 0 | 0 | 0 | 0 | 0 |

TABLE 4-continued
Results from Antibacterial Preliminary Screening- Compounds are given scores from 0-3 in the preliminary screening in which 0 represents no inhibition and 3 is comparable to commercial antibiotic control.
| HGN# | Structure | BT | MS | CX | CP | EC | KP | ML | BC | PA |
|---|---|---|---|---|---|---|---|---|---|---|
| 336 | 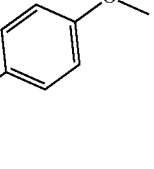 | 0 | 0 | 0 | 0 | 0 | 0 | 0 | 0 | 0 |
| 333 | 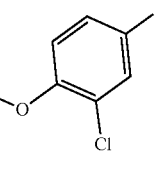 | 0 | 0 | 0 | 0 | 0 | 0 | 0 | 0 | 2 |
| 334 | 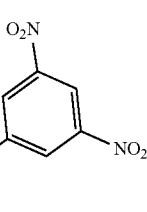 | 0 | 0 | 0 | 0 | 0 | 0 | 0 | 0 | 0 |
| 335 | 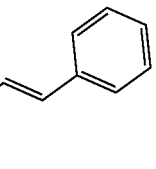 | 0 | 0 | 0 | 0 | 0 | 0 | 0 | 0 | 1 |
| 421 | 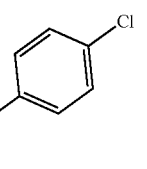 | 1 | 1 | 0 | 0 | 0 | 0 | 0 | 0 | 0 |
| 422 | 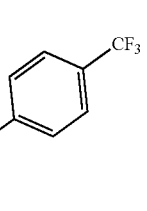 | 1 | 1 | 0 | 0 | 0 | 0 | 0 | 0 | 0 |
| 221 | 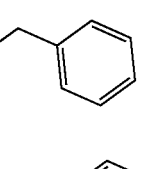 | 0 | 0 | 0 | 0 | 0 | 0 | 0 | 0 | 0 |
| 215 | 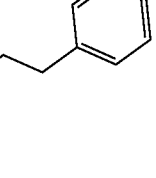 | 0 | 0 | 0 | 0 | 0 | 0 | 0 | 0 | 0 |

TABLE 4-continued

Results from Antibacterial Preliminary Screening- Compounds are given scores from 0-3 in the preliminary screening in which 0 represents no inhibition and 3 is comparable to commercial antibiotic control.

| HGN# | Structure | BT | MS | CX | CP | EC | KP | ML | BC | PA |
|------|-----------|----|----|----|----|----|----|----|----|----|
| 287 | indole-oxadiazole-biphenyl (3-) | 0 | 0 | 0 | 0 | 0 | 0 | 0 | 0 | 0 |
| 288 | indole-oxadiazole-biphenyl (4-) | 0 | 0 | 0 | 0 | 0 | 0 | 0 | 0 | 0 |
| 340 | indole-(dibromo-hydroxyphenyl) | 0 | 0 | 0 | 0 | 0 | 0 | 0 | 2 | 0 |

BT = *Burkholderia thailandensis*, MS = *Mycobacterium smegmatis*, CX = *Corynebacterium xerosis*, CP = *Corynebacterium pseudodiphtheriae*, EC = *Escherichia coli*, KP = *Klebsiella pneumonia*, ML = *Micrococcus luteus*, BC = *Bacillus cereus*, PA = *Pseudomonas aeruginosa*.
(University of Northern Illinois, Debarati Gose and R. Meganathan)

Antibacterial assay results for additional oxadiazole compounds shown in Table 5. The data obtained from this assay was determined by the organisms' growth and zone of inhibition, measured in millimeters, when introduced to a compound. The antibacterial assays show the zone of inhibition of each of the nine organisms.

TABLE 5

Results from Antibacterial Preliminary Screening- Compounds are given scores from 0-3 in the preliminary screening in which 0 represents no inhibition and 3 is comparable to commercial antibiotic control.

| HGN # | X | Y | Z | R | Conc. (mM) | Bt | Pa | Ml | Kp | Ec | Bc | Ms | Cx | Cp |
|-------|---|---|---|---|------------|----|----|----|----|----|----|----|----|----|
| 811 | C | NH | O | phenyl | 0.1 | 0 | 0 | 0 | 0 | 0 | 0 | 0 | 0 | 0 |
|     |   |    |   |        | 0.5 | 8 | 0 | 0 | 0 | 0 | 12.5 | 0 | 0 | 0 |
|     |   |    |   |        | 1   | 12 | 0 | 0 | 0 | 0 | 16 | 0 | 0 | 0 |
| 810 | C | NH | O | 2,4-dichlorophenyl | 0.1 | 0 | 0 | 0 | 0 | 0 | 0 | 0 | 0 | 0 |
|     |   |    |   |        | 0.5 | 11.5 | 0 | 0 | 0 | 0 | 11 | 0 | 0 | 0 |
|     |   |    |   |        | 1   | 17 | 0 | 0 | 0 | 0 | 16.5 | 0 | 0 | 0 |
| 824 | N | S | $CH_2$ | 2,4-dichlorophenyl | 0.1 | 0 | 0 | 0 | 0 | 0 | 0 | 0 | 0 | 0 |
|     |   |    |   |        | 0.5 | 0 | 0 | 0 | 0 | 0 | 0 | 12 | 0 | 0 |
|     |   |    |   |        | 1   | 0 | 0 | 0 | 0 | 0 | 0 | 18 | 0 | 10 |

TABLE 5-continued

Results from Antibacterial Preliminary Screening- Compounds are given scores from 0-3 in the preliminary screening in which 0 represents no inhibition and 3 is comparable to commercial antibiotic control.

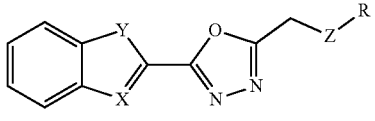

| HGN # | X | Y | Z | R | Conc. (mM) | Bt | Pa | Ml | Kp | Ec | Bc | Ms | Cx | Cp |
|---|---|---|---|---|---|---|---|---|---|---|---|---|---|---|
| 840 | N | S | O | 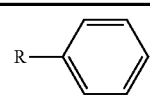 | 0.1 | 0 | 0 | 0 | 0 | 0 | 0 | 0 | 0 | 0 |
|  |  |  |  |  | 0.5 | 14 | 0 | 0 | 0 | 0 | 0 | 0 | 0 | 12 |
|  |  |  |  |  | 1 | 17.5 | 0 | 0 | 16.5 | 0 | 14.5 | 0 | 0 | 19 |
| 826 | N | S | O | 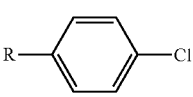 | 0.1 | 0 | 0 | 0 | 0 | 0 | 0 | 0 | 0 | 0 |
|  |  |  |  |  | 0.5 | 0 | 0 | 0 | 0 | 0 | 0 | 13 | 0 | 0 |
|  |  |  |  |  | 1 | 0 | 0 | 0 | 0 | 0 | 12 | 20 | 0 | 0 |
| 825 | N | S | O |  | 0.1 | 0 | 0 | 0 | 0 | 0 | 0 | 0 | 0 | 0 |
|  |  |  |  |  | 0.5 | 0 | 0 | 0 | 0 | 0 | 0 | 13 | 0 | 0 |
|  |  |  |  |  | 1 | 0 | 0 | 11 | 0 | 0 | 11.5 | 18 | 0 | 0 |
| 833 | N | S | O |  | 0.1 | 0 | 0 | 0 | 0 | 0 | 0 | 0 | 0 | 0 |
|  |  |  |  |  | 0.5 | 12 | 0 | 0 | 0 | 0 | 10 | 0 | 0 | 0 |
|  |  |  |  |  | 1 | 17 | 0 | 13 | 0 | 0 | 15 | 0 | 15 | 14 |
| 834 | N | S | O |  | 0.1 | 0 | 0 | 0 | 0 | 0 | 0 | 0 | 0 | 0 |
|  |  |  |  |  | 0.5 | 0 | 0 | 0 | 0 | 0 | 11 | 0 | 0 | 0 |
|  |  |  |  |  | 1 | 0 | 0 | 0 | 0 | 0 | 18 | 0 | 0 | 0 |
| 835 | N | S | O | 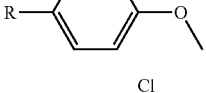 | 0.1 | 0 | 0 | 0 | 0 | 0 | 0 | 0 | 0 | 0 |
|  |  |  |  |  | 0.5 | 12.5 | 0 | 0 | 14 | 0 | 14 | 0 | 0 | 0 |
|  |  |  |  |  | 1 | 18 | 0 | 14 | 18 | 0 | 20 | 0 | 0 | 0 |
| 836 | N | S | O |  | 0.1 | 0 | 0 | 0 | 0 | 0 | 0 | 0 | 0 | 0 |
|  |  |  |  |  | 0.5 | 15 | 0 | 0 | 0 | 0 | 0 | 0 | 0 | 0 |
|  |  |  |  |  | 1 | 18 | 0 | 0 | 7 | NT | 13 | 0 | 11 | 0 |
| 333 | N | S | O | 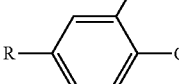 | 0.1 | 0 | 0 | 0 | 0 | 0 | 0 | 0 | 0 | 0 |
|  |  |  |  |  | 0.5 | 15 | 18 | 0 | 0 | 0 | 0 | 0 | 0 | 0 |
|  |  |  |  |  | 1 | 19 | 25 | 0 | 0 | 0 | 12.5 | 0 | 0 | 0 |
| 837 | N | S | O | 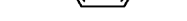 | 0.1 | 0 | 0 | 0 | 0 | 0 | 0 | 0 | 0 | 0 |
|  |  |  |  |  | 0.5 | 13 | 0 | 6 | 0 | 10 | 13 | 0 | 11 | 0 |
|  |  |  |  |  | 1 | 19.5 | 0 | 10 | 0 | 17 | 19 | 0 | 17 | 0 |

Bt = *Burkholderia thailandensis*, Ms = *Mycobacterium smegmatis*, Cx = *Corynebacterium xerosis*, Cp = *Corynebacterium pseudodiphtheriae*, Ec = *Escherichia coli*, Kp = *Klebsiella pneumonia*, Ml = *Micrococcus luteus*, Bc = *Bacillus cereus*, Pa = *Pseudomonas aeruginosa*.

TABLE 6

| Target | Organism | SSGCID ID | Primary Screen Hits |
|---|---|---|---|
| IspD | *Mycobacterium paratuberculosis* | MypaA.00168.a | 102 |
| IspE | *Mycobacterium abscessus* | MyabA.00725.a | 176 |
| IspF | *Burkholderia pseudomallei* | BupsA.00122.a | 72 |
| control | *Toxoplasma gondii* | TogoA.00914.a | 81 |

The following publications are hereby incorporated by reference herein:

60 Bali, A., et al. Synthesis, docking and pharmacological evaluation of novel indole based potential atypical antipsychotics. *European Journal of Medicinal Chemistry* 2014, 74, 477-490.

65 Baugh, L., et al. Increasing the structural coverage of tuberculosis drug targets. *Tuberculosis* (Edinb) 2015, 95, 142-148.

Bjorkelid, C., et al. Structural and functional studies of mycobacterial IspD enzymes. *Acta Crystallogr D Biol Crystallogr* 2011, 67, 403-414.

Eisenreich, W., et al. Biosynthesis of isoprenoids via the non-mevalonate pathway. *Cellular and Molecular Life Sciences CMLS* 2004, 61,1401-1426.

Eoh, H., et al. Characterization of the *Mycobacterium tuberculosis* 4-diphosphocytidyl-2-C-methyl-D-erythritol synthase: potential for drug development. *J Bacteriol* 2007, 189, 8922-8927.

Hansch, C. and T. Fujita. p-σ-π Analysis. A Method for the Correlation of Biological Activity and Chemical Structure. *Journal of the American Chemical Society* 1964, 86, 1616-1626.

Hedden, P. and S. G. Thomas. Gibberellin biosynthesis and its regulation. *Biochem J* 2012, 444, 11-25.

Hunter, W. N. The Non-mevalonate Pathway of Isoprenoid Precursor Biosynthesis. *Journal of Biological Chemistry* 2007, 282, 21573-21577.

Illarionova, V., et al. Nonmevalonate terpene biosynthesis enzymes as antiinfective drug targets: substrate synthesis and high-throughput screening methods. *J Org Chem* 2006, 71, 8824-8834.

Imlay, L. S., et al. *Plasmodium* IspD (2-C-Methyl-d-erythritol 4-Phosphate Cytidyltransferase), an Essential and Druggable Antimalarial Target. *ACS Infectious Diseases* 2015, 1, 157-167.

Jomaa, H., et al. Inhibitors of the Nonmevalonate Pathway of Isoprenoid Biosynthesis as Antimalarial Drugs. *Science* 1999, 285, 1573-1576.

Kranz, J. K. and C. Schalk-Hihi. Chapter eleven—Protein Thermal Shifts to Identify Low Molecular Weight Fragments. *Methods in Enzymology*. C. K. Lawrence, Academic Press. 2011, 493, 277-298.

Kunfermann, A., Witschel, M., Illarionov, B., Martin, R., Rottmann, M., Höffken, H. W., Seet, M., Eisenreich, W., Knölker, H.-J., Fischer, M., Bacher, A., Groll, M. and Diederich, F. Pseudilins: Halogenated, Allosteric Inhibitors of the Non-Mevalonate Pathway Enzyme IspD. *Angew. Chem. Int. Ed.* 2014, 53, 2235-2239.

Kuzuyama, T., et al. Formation of 4-(cytidine 5'-diphospho)-2-C-methyl-d-erythritol from 2-C-methyl-d-erythritol 4-phosphate by 2-C-methyl-d-erythritol 4-phosphate cytidylyltransferase, a new enzyme in the nonmevalonate pathway. *Tetrahedron Letters* 2000, 41, 703-706.

Kuzuyama, T., et al. Studies on the nonmevalonate pathway: conversion of 4-(cytidine 5'-diphospho)-2-C-methyl-d-erythritol to its 2-phospho derivative by 4-(cytidine 5'-diphospho)-2-C-methyl-d-erythritol kinase. *Tetrahedron Letters* 2000, 41, 2925-2928.

Lange, B. M., et al. Isoprenoid biosynthesis: The evolution of two ancient and distinct pathways across genomes. *Proceedings of the National Academy of Sciences* 2000, 97, 13172-13177.

Lavinder, J. J., et al. High-Throughput Thermal Scanning: A General, Rapid Dye-Binding Thermal Shift Screen for Protein Engineering. *Journal of the American Chemical. Society* 2009, 131, 3794-3795.

Li, Wenming, Xiaobo Li, Yuqing Duan, Zhirong Deng, and Runling Wang. 1-(2-Hydroxy-3,5-dimethoxyphenyl)-Ethanone. *Acta Crystallographica Section E Structure Reports Online* 2012, E68, o116.

Lüttgen, H., et al. Biosynthesis of terpenoids: YchB protein of *Escherichia coli* phosphorylates the 2-hydroxy group of 4-diphosphocytidyl-2C-methyl-d-erythritol. *Proceedings of the National Academy of Sciences* 2000, 97, 1062-1067.

Martin, R., Risacher, C., Barthel, A., Jäger, A., Schmidt, A. W., Richter, S., Böhl, M., Preller, M., Chinthalapudi, K., Manstein, D. J., Gutzeit, H. O. and Knölker, H.-J. Silver (I)-Catalyzed Route to Pyrroles: Synthesis of Halogenated Pseudilins as Allosteric Inhibitors for Myosin ATPase and X-ray Crystal Structures of the Protein—Inhibitor Complexes. *Eur. J Org. Chem.* 2014, 4487-4505.

Masini, T. and A. K. H. Hirsch. Development of Inhibitors of the 2C-Methyl-d-erythritol 4-Phosphate (MEP) Pathway Enzymes as Potential Anti-Infective Agents. *Journal of Medicinal Chemistry* 2014, 57, 9740-9763.

Miziorko, H. M. Enzymes of the mevalonate pathway of isoprenoid biosynthesis. *Arch Biochem Biophys*, 2011, 505, 131-143.

Niesen, F. H., et al. The use of differential scanning fluorimetry to detect ligand interactions that promote protein stability. *Nat. Protocols* 2007, 2, 2212-2221.

Rajeeva, B., et al. Synthesis and Antimicrobial Activity of Some New 2-Substituted Benzothiazole Derivatives. *E-Journal of Chemistry* 2009, 6, 775-779.

Richard, S. B., et al. Kinetic Analysis of *Escherichia coli* 2-C-Methyl-d-erythritol-4-phosphate Cytidyltransferase, Wild Type and Mutants, Reveals Roles of Active Site Amino Acids. *Biochemistry* 2004, 43, 12189-12197.

Robba, M., D. Maume, and J. C. Lancelot. As-Triazino[4,5-a]indoles. I. Indole Derivatives. *Bulletin De La Societe Chimique De France Pt. 2* 1977, 3, 333-36.

Rohmer, M. The discovery of a mevalonate-independent pathway for isoprenoid biosynthesis in bacteria, algae and higher plants. *Natural Product Reports* 1999, 16, 565-574

Sawhney, S. N., and Asha Gupta. Synthesis of Some 2-(5-substituted 1,3,4-oxadiazol-2-yl)-, 2-(5-substituted 1,3,4-thiadiazol-2-yl)-, and 2-(3-mercapto-4-substituted-4H-1, 2,4-triazol-5-yl)benzimidazoles as Potential Antiinflammatory Agents. *Indian Journal of Chemistry, Section B: Organic Chemistry Including Medicinal Chemistry* 1991, 30B, 407-12.

Topliss, J. G. A manual method for applying the Hansch approach to drug design. *Journal of Medicinal Chemistry* 1977, 20, 463-469.

Topliss, J. G. Utilization of operational schemes for analog synthesis in drug design. *Journal of Medicinal Chemistry* 1972, 15, 1006-1011.

Viegas, A., et al. Saturation-Transfer Difference (STD) NMR: A Simple and Fast Method for Ligand Screening and Characterization of Protein Binding. *Journal of Chemical Education* 2011, 88, 990-994.

Vranova, E., et al. Network analysis of the MVA and MEP pathways for isoprenoid synthesis. *Annu Rev Plant Biol* 2013, 64, 665-700.

Vranova, E., et al. Structure and dynamics of the isoprenoid pathway network. *Mol Plant* 2012, 5, 318-333.

Wiemer, A. J., et al. Isoprenoid metabolism as a therapeutic target in gram-negative pathogens. *Curr Top Med Chem* 2010, 10, 1858-1871.

World Health Organization-Malaria-Factsheet on the World Malaria Report 2013. http://www.whoint/malaria/media/world_malaria_report_2013/en/ (accessed May 4, 2015).

Yamada, N., et al. Synthesis and Bleaching Activity of 1,5-Disubstituted Imidazoles. *Bioscience, Biotechnology, and Biochemistry* 1992, 56, 1943-1948.

Zhao, L., et al. Methylerythritol Phosphate Pathway of Isoprenoid Biosynthesis. *Annual Review of Biochemistry*, 2013, 82, 497-530.

We claim:

1. A method to inhibit bacteria, the method comprising contacting the bacteria with a compound of the formula I

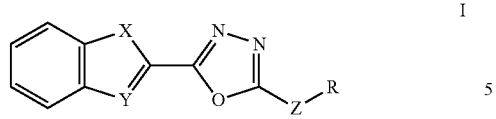

wherein
X is NH or S;
Y is CH or N;
Z is selected from the group consisting of $C_1$-$C_6$ alkylene, $C_2$-$C_6$ alkenylene, and $C_3$-$C_6$ cycloalkylene, or Z is absent; and
R is selected from the group consisting of halogen, —OH, —$NO_2$, $C_2$-$C_6$ alkenyl, —O($C_1$-$C_6$ alkyl), and —O($C_6$-$C_{10}$ aryl), wherein each hydrogen atom in $C_2$-$C_6$ alkenyl, and —O($C_1$-$C_6$ alkyl) is independently optionally substituted by halogen, —OH, or —$NO_2$, and wherein each hydrogen atom in —O($C_6$-$C_{10}$ aryl) is optionally substituted by —OH.

* * * * *

UNITED STATES PATENT AND TRADEMARK OFFICE
CERTIFICATE OF CORRECTION

| | | |
|---|---|---|
| PATENT NO. | : 11,026,426 B2 | Page 1 of 1 |
| APPLICATION NO. | : 15/933608 | |
| DATED | : June 8, 2021 | |
| INVENTOR(S) | : Timothy J. Hagen et al. | |

It is certified that error appears in the above-identified patent and that said Letters Patent is hereby corrected as shown below:

In the Specification

In Column 1, beginning at Line 14, the paragraph should read as follows:
This invention was made with government support under Contract No. 1R15 AI 113653-01 awarded by the National Institutes of Health. The government has certain rights in the invention.

Signed and Sealed this
Twenty-first Day of February, 2023

Katherine Kelly Vidal
*Director of the United States Patent and Trademark Office*